US011510807B2

(12) United States Patent
Grover et al.

(10) Patent No.: US 11,510,807 B2
(45) Date of Patent: *Nov. 29, 2022

(54) SYSTEMS AND METHODS FOR DELIVERING BIOMATERIALS

(71) Applicant: Contraline, Inc., Charlottesville, VA (US)

(72) Inventors: Gregory Grover, Houston, TX (US); Kevin S. Eisenfrats, Charlottesville, VA (US)

(73) Assignee: Contraline, Inc., Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/584,046

(22) Filed: Jan. 25, 2022

(65) Prior Publication Data

US 2022/0142812 A1    May 12, 2022

Related U.S. Application Data

(63) Continuation of application No. 16/681,572, filed on Nov. 12, 2019, now Pat. No. 11,253,391.

(Continued)

(51) Int. Cl.
*A61F 6/00* (2006.01)
*A61M 5/168* (2006.01)
(Continued)

(52) U.S. Cl.
CPC ............ *A61F 6/005* (2013.01); *A61F 6/22* (2013.01); *A61M 5/1408* (2013.01);
(Continued)

(58) Field of Classification Search
CPC .... A61F 6/005; A61F 6/22; A61F 6/24; A61F 6/20; A61F 6/225; A61F 6/206;
(Continued)

(56) References Cited

U.S. PATENT DOCUMENTS

| | | | |
|---|---|---|---|
| 3,223,083 A | 12/1965 | Cobey | |
| 3,716,056 A | 2/1973 | Brodsky et al. | |

(Continued)

FOREIGN PATENT DOCUMENTS

| | | |
|---|---|---|
| CN | 101812194 | 4/2012 |
| CN | 203493942 | 3/2014 |
| CN | 103724638 | 12/2015 |
| EP | 0547530 | 6/1993 |

(Continued)

OTHER PUBLICATIONS

Office Action for U.S. Appl. No. 16/681,572, dated Oct. 4, 2021.

(Continued)

*Primary Examiner* — Ophelia A Hawthorne
(74) *Attorney, Agent, or Firm* — Ambrose, Mills & Lazarow, PLLC

(57) ABSTRACT

Delivery systems and methods for forming and delivering biomaterials from two components are described herein. In particular, apparatus and methods for performing controlled delivery of multicomponent delivery of biomaterials into or onto a body part, such as a body lumen are described. More specifically, in some embodiments, the apparatus and methods are directed towards controlled delivery of micro-volumes of biomaterials into or onto a target location, the micro-volumes being defined as 0.001 mL-1 mL (or 1 μL-1,000 μL) of volume.

20 Claims, 44 Drawing Sheets

Related U.S. Application Data

(60) Provisional application No. 62/760,650, filed on Nov. 13, 2018.

(51) Int. Cl.
  *A61F 6/22* (2006.01)
  *A61M 5/145* (2006.01)
  *A61M 39/10* (2006.01)
  *A61M 5/14* (2006.01)

(52) U.S. Cl.
  CPC ...... *A61M 5/1452* (2013.01); *A61M 5/16827* (2013.01); *A61M 39/10* (2013.01); *A61M 39/105* (2013.01); *A61M 2005/1402* (2013.01); *A61M 2205/10* (2013.01); *A61M 2205/3334* (2013.01)

(58) Field of Classification Search
  CPC .. A61F 6/202; A61F 6/02; A61F 6/204; A61F 6/00; A61F 2230/006; A61F 2/0022; A61F 2/26; A61F 5/04; A61F 5/41; A61F 6/04; A61M 5/1452; A61M 5/16827; A61M 39/105; A61M 2005/1402; A61M 2205/10; A61M 2205/3334
  See application file for complete search history.

(56) References Cited

U.S. PATENT DOCUMENTS

| | | |
|---|---|---|
| 4,044,757 A | 8/1977 | McWhorter et al. |
| 4,269,174 A | 5/1981 | Adair |
| 4,273,109 A | 6/1981 | Enderby |
| 4,804,691 A | 2/1989 | English et al. |
| 4,887,605 A | 12/1989 | Angelsen et al. |
| 4,920,982 A | 5/1990 | Goldstein |
| 4,967,949 A | 11/1990 | Sandhaus |
| 4,978,336 A | 12/1990 | Capozzi et al. |
| 4,979,942 A | 12/1990 | Wolf et al. |
| 5,065,751 A | 11/1991 | Wolf |
| 5,240,997 A | 8/1993 | Yanai et al. |
| 5,248,311 A | 9/1993 | Black et al. |
| 5,258,042 A | 11/1993 | Mehta |
| 5,380,317 A | 1/1995 | Everett et al. |
| 5,383,896 A | 1/1995 | Gershony et al. |
| 5,437,660 A | 8/1995 | Johnson et al. |
| 5,488,075 A | 1/1996 | Guha |
| 5,575,815 A | 11/1996 | Slepian et al. |
| 5,607,419 A | 3/1997 | Amplatz et al. |
| 5,612,052 A | 3/1997 | Shalaby |
| 5,667,767 A | 9/1997 | Greff et al. |
| 5,695,740 A | 12/1997 | Porter |
| 5,702,717 A | 12/1997 | Cha et al. |
| 5,714,159 A | 2/1998 | Shalaby |
| 5,749,968 A | 5/1998 | Melanson et al. |
| 5,797,397 A | 8/1998 | Rosenberg |
| 5,833,682 A | 11/1998 | Amplatz et al. |
| 5,866,554 A | 2/1999 | Shalaby et al. |
| 5,947,893 A | 9/1999 | Agrawal et al. |
| 5,968,018 A | 10/1999 | Freeman et al. |
| 5,989,580 A | 11/1999 | Wallace et al. |
| 6,037,331 A | 3/2000 | Shalaby et al. |
| 6,066,325 A | 5/2000 | Wallace et al. |
| 6,096,052 A | 8/2000 | Callister et al. |
| 6,103,254 A | 8/2000 | Wallace et al. |
| 6,197,940 B1 | 3/2001 | Klinefelter |
| 6,224,893 B1 | 5/2001 | Langer et al. |
| 6,297,337 B1 | 10/2001 | Marchant et al. |
| 6,328,229 B1 | 12/2001 | Duronio et al. |
| 6,378,524 B1 | 4/2002 | Jones |
| 6,379,373 B1 | 4/2002 | Sawhney et al. |
| 6,394,314 B1 | 5/2002 | Sawhney et al. |
| 6,413,539 B1 | 7/2002 | Shalaby |
| 6,432,116 B1 | 8/2002 | Callister et al. |
| 6,454,762 B1 | 9/2002 | Roesler et al. |
| 6,461,325 B1 | 10/2002 | Delmotte et al. |
| 6,461,569 B1 | 10/2002 | Boudreaux |
| 6,464,663 B1 | 10/2002 | Zinger |
| 6,485,426 B2 | 11/2002 | Sandhu |
| 6,514,534 B1 | 2/2003 | Sawhney |
| 6,514,535 B2 | 2/2003 | Marchant |
| 6,531,111 B1 | 3/2003 | Whalen, II et al. |
| 6,610,033 B1 | 8/2003 | Melanson et al. |
| 6,660,247 B1 | 12/2003 | Gutowska et al. |
| 6,703,047 B2 | 3/2004 | Sawhney et al. |
| 6,719,778 B1 | 4/2004 | Tassel et al. |
| 6,723,090 B2 | 4/2004 | Altshuler et al. |
| 6,723,781 B1 | 4/2004 | Frate et al. |
| 6,756,031 B2 | 6/2004 | Evans et al. |
| 6,802,838 B2 | 10/2004 | Loeb et al. |
| 6,852,099 B2 | 2/2005 | Redl et al. |
| 6,858,219 B2 | 2/2005 | Evans et al. |
| 6,957,747 B2 | 10/2005 | Peeler et al. |
| 6,970,587 B1 | 11/2005 | Rogers |
| 7,022,073 B2 | 4/2006 | Fan et al. |
| 7,073,504 B2 | 7/2006 | Callister et al. |
| 7,135,027 B2 | 11/2006 | Delmotte |
| 7,160,931 B2 | 1/2007 | Cheng et al. |
| 7,252,677 B2 | 8/2007 | Burwell et al. |
| 7,347,850 B2 | 3/2008 | Sawhney |
| 7,396,354 B2 | 7/2008 | Rychnovsky et al. |
| 7,398,780 B2 | 7/2008 | Callister et al. |
| 7,641,075 B2 | 1/2010 | Crews |
| 7,694,683 B2 | 4/2010 | Callister et al. |
| 7,754,212 B2 | 7/2010 | Klinefelter |
| 7,789,891 B2 | 9/2010 | Wallace |
| 7,871,637 B2 | 1/2011 | Qian et al. |
| 7,914,514 B2 | 3/2011 | Calderon |
| 7,914,541 B2 | 3/2011 | Sawhney et al. |
| 7,918,863 B2 | 4/2011 | Nguyen et al. |
| 7,975,697 B2 | 7/2011 | Callister et al. |
| 8,048,086 B2 | 11/2011 | Lee-Sepsick et al. |
| 8,048,101 B2 | 11/2011 | Lee-Sepsick et al. |
| 8,052,669 B2 | 11/2011 | Lee-Sepsick et al. |
| 8,113,205 B2 | 2/2012 | Callister et al. |
| 8,123,693 B2 | 2/2012 | Connor et al. |
| 8,137,304 B2 | 3/2012 | Chavez et al. |
| 8,226,680 B2 | 7/2012 | Wallace |
| 8,235,047 B2 | 8/2012 | Swann et al. |
| 8,257,723 B2 | 9/2012 | Noyes |
| 8,303,981 B2 | 11/2012 | Wallace et al. |
| 8,316,853 B2 | 11/2012 | Lee-Sepsick et al. |
| 8,316,854 B2 | 11/2012 | Lee-Sepsick et al. |
| 8,322,341 B2 | 12/2012 | Koeller |
| 8,324,193 B2 | 12/2012 | Lee-Sepsick et al. |
| 8,336,552 B2 | 12/2012 | Lee-Sepsick et al. |
| 8,343,183 B2 | 1/2013 | D'Alessio et al. |
| 8,343,710 B1 | 1/2013 | Anseth et al. |
| 8,353,892 B2 | 1/2013 | Thompson et al. |
| 8,357,378 B2 | 1/2013 | Wallace et al. |
| 8,360,064 B2 | 1/2013 | Swann et al. |
| 8,434,489 B2 | 5/2013 | Gopal et al. |
| 8,440,487 B2 | 5/2013 | Furumura |
| 8,512,729 B2 | 8/2013 | Wallace et al. |
| 8,523,848 B2 | 9/2013 | Fried et al. |
| 8,550,085 B2 | 10/2013 | Callister et al. |
| 8,551,001 B2 | 10/2013 | Connor et al. |
| 8,603,025 B2 | 12/2013 | Pongratz et al. |
| 8,603,080 B1 | 12/2013 | Fried et al. |
| 8,603,511 B2 | 12/2013 | Wallace et al. |
| 8,613,282 B2 | 12/2013 | Nikolchev et al. |
| 8,689,792 B2 | 4/2014 | Jimenez et al. |
| 8,695,606 B2 | 4/2014 | Lee-Sepsick et al. |
| 8,726,906 B2 | 5/2014 | Lee-Sepsick et al. |
| 8,766,853 B2 | 7/2014 | Furumura et al. |
| 8,801,764 B2 | 8/2014 | Suarez et al. |
| 8,933,784 B2 | 1/2015 | Furumura et al. |
| 8,960,501 B2 | 2/2015 | Pappalardo |
| 8,986,730 B2 | 3/2015 | Sawhney et al. |
| 9,034,053 B2 | 5/2015 | Lee-Sepsick et al. |
| 9,155,543 B2 | 10/2015 | Walsh et al. |
| 9,180,196 B2 | 11/2015 | Anseth et al. |
| 9,193,816 B2 | 11/2015 | Jiang et al. |
| 9,220,880 B2 | 12/2015 | Lee-Sepsick et al. |

(56) References Cited

U.S. PATENT DOCUMENTS

| | | | |
|---|---|---|---|
| 9,308,283 B2 | 4/2016 | Campbell et al. | |
| 9,445,795 B2 | 9/2016 | Ohri et al. | |
| 9,463,004 B2 | 10/2016 | Campbell et al. | |
| 9,492,383 B2 | 11/2016 | Gravett et al. | |
| 9,566,365 B2 | 2/2017 | Kaplan et al. | |
| 9,586,005 B2 | 3/2017 | Steffen | |
| 9,707,319 B2 | 7/2017 | Geppert et al. | |
| 9,750,695 B2 | 9/2017 | Richard | |
| 9,861,515 B2 | 1/2018 | DePinto et al. | |
| 10,046,115 B2 | 8/2018 | Bokelman et al. | |
| 10,155,063 B2 | 12/2018 | Herr et al. | |
| 10,576,206 B2 | 3/2020 | Edwards et al. | |
| 10,751,124 B2 | 8/2020 | Eisenfrats et al. | |
| 11,253,391 B2 * | 2/2022 | Grover | A61M 39/10 |
| 2002/0032463 A1 | 3/2002 | Cruise et al. | |
| 2002/0051750 A1 | 5/2002 | Schutt et al. | |
| 2002/0106328 A1 | 8/2002 | Johnson et al. | |
| 2002/0106411 A1 | 8/2002 | Wironen et al. | |
| 2002/0173586 A1 | 11/2002 | Jeong et al. | |
| 2003/0185758 A1 | 10/2003 | Evans et al. | |
| 2003/0199865 A1 | 10/2003 | Knudson et al. | |
| 2003/0206864 A1 | 11/2003 | Mangin | |
| 2004/0013292 A1 | 1/2004 | Raunig | |
| 2004/0062808 A1 | 4/2004 | Langrana et al. | |
| 2004/0087930 A1 | 5/2004 | Whalen et al. | |
| 2004/0240715 A1 | 12/2004 | Wicker et al. | |
| 2005/0045183 A1 | 3/2005 | Callister et al. | |
| 2005/0142162 A1 | 6/2005 | Hunter et al. | |
| 2005/0147599 A1 | 7/2005 | Hunter et al. | |
| 2005/0149117 A1 | 7/2005 | Khosravi et al. | |
| 2005/0192616 A1 | 9/2005 | Callister et al. | |
| 2005/0266086 A1 | 12/2005 | Sawhney | |
| 2005/0283098 A1 | 12/2005 | Conston et al. | |
| 2005/0288481 A1 | 12/2005 | DesNoyer et al. | |
| 2006/0121087 A1 | 6/2006 | Williams et al. | |
| 2006/0222596 A1 | 10/2006 | Askari et al. | |
| 2006/0241452 A1 | 10/2006 | Cerofolini | |
| 2007/0016128 A1 | 1/2007 | Keller | |
| 2007/0060906 A1 | 3/2007 | Wu | |
| 2007/0163601 A1 | 7/2007 | Pollock et al. | |
| 2007/0197954 A1 | 8/2007 | Keenan | |
| 2007/0231366 A1 | 10/2007 | Sawhney et al. | |
| 2008/0039890 A1 | 2/2008 | Matson et al. | |
| 2008/0045865 A1 | 2/2008 | Kislev | |
| 2008/0071269 A1 | 3/2008 | Hilario et al. | |
| 2008/0103564 A1 | 5/2008 | Burkinshaw et al. | |
| 2008/0154345 A1 | 6/2008 | Taylor | |
| 2008/0308110 A1 | 12/2008 | Callister et al. | |
| 2009/0024155 A1 | 1/2009 | Lee-Sepsick et al. | |
| 2009/0048588 A1 | 2/2009 | Peng et al. | |
| 2009/0053276 A1 | 2/2009 | Richard | |
| 2009/0076459 A1 | 3/2009 | Goldberg | |
| 2009/0127288 A1 | 5/2009 | Keller | |
| 2009/0274678 A1 | 11/2009 | Calabro et al. | |
| 2009/0277457 A1 | 11/2009 | Hoey et al. | |
| 2010/0003297 A1 | 1/2010 | Tobias et al. | |
| 2010/0006339 A1 | 1/2010 | Desai | |
| 2010/0063392 A1 | 3/2010 | Nishina et al. | |
| 2010/0068153 A1 | 3/2010 | Bangera et al. | |
| 2010/0089406 A1 | 4/2010 | Kachiguina | |
| 2010/0158813 A1 | 6/2010 | Paradossi et al. | |
| 2010/0272672 A1 | 10/2010 | Kita et al. | |
| 2010/0318035 A1 | 12/2010 | Edwards et al. | |
| 2011/0021970 A1 | 1/2011 | Vo-Dinh et al. | |
| 2011/0065809 A1 | 3/2011 | Benz et al. | |
| 2011/0125185 A1 | 5/2011 | Stopek et al. | |
| 2011/0137150 A1 | 6/2011 | Connor et al. | |
| 2011/0165114 A1 | 7/2011 | McCoy et al. | |
| 2011/0245866 A1 | 10/2011 | Cassingham et al. | |
| 2012/0014978 A1 | 1/2012 | Hafner et al. | |
| 2012/0149781 A1 | 6/2012 | Lee et al. | |
| 2012/0165804 A1 | 6/2012 | Newell et al. | |
| 2012/0192872 A1 | 8/2012 | Rudakov et al. | |
| 2012/0226226 A1 | 9/2012 | Edwards et al. | |
| 2012/0295214 A1 | 11/2012 | Wang et al. | |
| 2013/0018314 A1 | 1/2013 | Teague et al. | |
| 2013/0131632 A1 | 5/2013 | Mudd et al. | |
| 2013/0220335 A1 | 8/2013 | Lee-Sepsick et al. | |
| 2013/0230496 A1 | 9/2013 | Mohapatra et al. | |
| 2013/0244975 A1 | 9/2013 | Baldwin et al. | |
| 2013/0245604 A1 | 9/2013 | Kouyoumjian et al. | |
| 2013/0331770 A1 | 12/2013 | Kirk et al. | |
| 2013/0331771 A1 | 12/2013 | Kirk et al. | |
| 2014/0046182 A1 | 2/2014 | Connor et al. | |
| 2014/0114261 A1 | 4/2014 | Geppert et al. | |
| 2014/0121699 A1 | 5/2014 | Anderson et al. | |
| 2014/0128497 A1 | 5/2014 | Ladet et al. | |
| 2014/0256831 A1 | 9/2014 | Ito et al. | |
| 2014/0261446 A1 | 9/2014 | Sjoquist et al. | |
| 2014/0276384 A1 | 9/2014 | Schwab et al. | |
| 2015/0045729 A1 | 2/2015 | Denzer et al. | |
| 2015/0068531 A1 | 3/2015 | Lee-Sepsick et al. | |
| 2015/0136144 A1 | 5/2015 | DePinto et al. | |
| 2015/0196684 A1 | 7/2015 | Guillen et al. | |
| 2015/0231246 A1 | 8/2015 | Tae et al. | |
| 2016/0024326 A1 | 1/2016 | Khan et al. | |
| 2016/0114046 A1 | 4/2016 | Brudno et al. | |
| 2016/0151535 A1 | 6/2016 | Hoare et al. | |
| 2016/0153999 A1 | 6/2016 | Tibbitt et al. | |
| 2016/0193392 A1 | 7/2016 | Askari et al. | |
| 2016/0317621 A1 | 11/2016 | Bright | |
| 2017/0014569 A1 | 1/2017 | Flanagan et al. | |
| 2017/0130194 A1 | 5/2017 | Lee et al. | |
| 2017/0136143 A1 | 5/2017 | Herr et al. | |
| 2017/0136144 A1 | 5/2017 | Herr et al. | |
| 2017/0189581 A1 | 7/2017 | Desai et al. | |
| 2017/0296749 A1 | 10/2017 | Porcher | |
| 2018/0028715 A1 | 2/2018 | Eisenfrats | |
| 2018/0092769 A1 | 4/2018 | DePinto et al. | |
| 2018/0185096 A1 | 7/2018 | Eisenfrats et al. | |
| 2018/0369481 A1 | 12/2018 | Pedersen et al. | |
| 2018/0369482 A1 | 12/2018 | Pedersen et al. | |
| 2018/0369483 A1 | 12/2018 | Pedersen et al. | |
| 2019/0009029 A1 | 1/2019 | Fabricus et al. | |
| 2019/0038454 A1 | 2/2019 | Eisenfrats et al. | |
| 2019/0053790 A1 | 2/2019 | Grover et al. | |
| 2019/0060513 A1 | 2/2019 | Herr et al. | |
| 2019/0224419 A1 | 7/2019 | Pedersen et al. | |
| 2020/0146876 A1 | 5/2020 | Grover et al. | |
| 2020/0147301 A1 | 5/2020 | Grover et al. | |
| 2020/0237388 A1 | 7/2020 | Eisenfrats et al. | |
| 2020/0352649 A1 | 11/2020 | Eisenfrats et al. | |
| 2020/0384207 A1 | 12/2020 | Egesborg et al. | |

FOREIGN PATENT DOCUMENTS

| | | |
|---|---|---|
| EP | 2233160 | 9/2010 |
| EP | 3275469 | 1/2018 |
| WO | WO2008115694 | 9/2008 |
| WO | WO2009137446 | 11/2009 |
| WO | WO2009148405 | 12/2009 |
| WO | WO2012112417 | 8/2012 |
| WO | WO2015168090 | 11/2015 |
| WO | WO2016094535 | 6/2016 |
| WO | WO2016154288 | 9/2016 |
| WO | WO2016164828 | 10/2016 |
| WO | WO2017044983 | 3/2017 |
| WO | WO2017083753 | 5/2017 |
| WO | WO2017114908 | 7/2017 |
| WO | WO2017152036 | 9/2017 |
| WO | WO2017174071 | 10/2017 |
| WO | WO2018104537 | 6/2018 |
| WO | WO2018129369 | 7/2018 |
| WO | WO2018144481 | 8/2018 |
| WO | WO2019070632 | 4/2019 |
| WO | WO2020102234 | 5/2020 |
| WO | WO2021035217 | 2/2021 |

OTHER PUBLICATIONS

Office Action for U.S. Appl. No. 16/681,577, dated Nov. 9, 2021.
PCT/US19/60986 International Search Report and Written Opinion dated Apr. 2, 2020.

(56) References Cited

OTHER PUBLICATIONS

International Search Report and Written Opinion for PCT/US2021/032235, dated Sep. 28, 2021.
Abbe, Carmen R. et al. "Assessing safety in hormonal male contraception: a critical appraisal of adverse events reported in a male contraceptive trial," BMJ Sex. Reprod. Health, vol. 46, No. 2, Apr. 2020, pp. 139-146, HHS Public Access, Arthor Manuscript, 15 pages.
Abdala, Nitamar et al., "Use of Ethylene Vinyl Alcohol Copolymer for Tubal Sterilization by Selective Cathelerization in Rabbits," Journal of Vascular and Interventional Radiology, vol. 12(8), Aug. 2001, pp. 979-984.
Bank, Alan J., et al., "Contribution of Collagen, Elastin, and Smooth Muscle to In Vivo Human Brachial Artery Wall Stress and Elastic Modulus," Circulation, 1996;94:3263-3270, Originally published Dec. 15, 1996, 17 pgs.
Bearak, Jonathan et al. "Global, regional, and subregional trends in unintended pregnancy and its outcomes from 1990 to 2014: estimates from a Bayesian hierarchical model," Lancet Glob. Health, vol. 6, Apr. 2018, pp. e380-e389.
Behre, Hermann et al. "Efficacy and Safety of an Injectable Combination Hormonal Contraceptive for Men," J. Clin. Endocrinol. Metab. vol. 101, No. 12 Dec. 2016, pp. 4779-4788.
Bustamante-Forest, Rosa et al. "Changing men's involvement in reproductive health and family planning," Nurs. Clin. North Am. 39, 301-318 (2004).
Calliada, Fabrizio, et al., "Ultrasound contrast agents: basic principles", European Journal of Radiology 27 (1998) pp. S157-S160.
Chaki, S.P. et al., "A short-term evaluation of semen and accessory sex gland function in phase III trial subjects receiving intravasal contraceptive RISUG," Contraception, vol. 67(1), 2003, pp. 73-78.
Chao, Jing H. et al. "The current state of male hormonal contraception," Pharmacology & Therapeutics, Accepted Manuscript, vol. 163, Jul. 2016, (42 pgs.).
Clenny T.L. et al., "Vasectomy Techniques," Am Fam Physician, vol. 60(1), Jul. 1, 1999, 9 pgs.
Colagross-Schouten, Angela et al. "The contraceptive efficacy of intravas injection of Vasalgel™ for adult male rhesus monkeys," Basic and Clinical Andrology, 27:4 (2017), 7 pages.
Cosgrove, David "Ultrasound contrast agents: An overview," European Journal of Radiology, vol. 60, Issue 3, pp. 324-330.
Grover, Gregory N. et al., "Biocompatible Hydrogels by Oxime Click Chemistry," Biomacromolecules, vol. 13, No. 10, Oct. 8, 2012, pp. 1-10.
Guha, S. K. et al. "Phase I clinical trial of an injectable contraceptive for the male," Contraception vol. 48, (1993) pp. 367-375.
Guha, Sujoy K. et al., "Phase II Clinical Trial of a Vas Deferens Injectable Contraceptive for the Male," Contraception, vol. 56, 1997, pp. 245-250.
Guha, Sujoy K. "Biophysical mechanism-mediated time-dependent effect on sperm of human and monkey vas implanted polyelectrolyte contraceptive," Asian J. Androl. 9(2), (2007) pp. 221-227.
Guimaraes, C. F. et al. "The stiffness of living tissues and its implications for tissue engineering," Nature Reviews, Materials 5, 2020, 20 pgs.
Hafez, ES, et al. "Atlas of Human Reproduction: By Scanning Electron Microscopy", 1982, MTP Press, Hingham, MA, Part 1-1 (separated into 4 parts for Filing), 85 pgs.
Hafez, ES, et al. "Atlas of Human Reproduction: By Scanning Electron Microscopy", 1982, MTP Press, Hingham, MA, Part 1-2 (separated into 4 parts for Filing), 85 pgs.
Hafez, ES, et al. "Atlas of Human Reproduction: By Scanning Electron Microscopy", 1982, MTP Press, Hingham, MA, Part 2-1 (separated into 4 parts for Filing), 66 pgs.
Hafez, ES, et al. "Atlas of Human Reproduction: By Scanning Electron Microscopy", 1982, MTP Press, Hingham, MA, Part 2-2 (separated into 4 parts for Filing), 101 pgs.
Hashemi, Ehsan et al., "Cyto and genotoxicities of graphene oxide and reduced graphene oxide sheets on spermatozoa," RSC Advances, 4(52), 2014, pp. 27213-27223.
Heinemann, Klaas et al. "Attitudes toward male fertility control: results of a multinational survey on four continents," Human Reproduction vol. 20, No. 2, (2005), pp. 549-556.
International Standard "Biological evaluation of medical devices. Part 5: Tests for in vitro cytotoxicity." ISO 10993-5, Third edition Jun. 1, 2009, 42 pgs.
Jha, R.K. et al., "Smart RISUG: A potential new contraceptive and its magnetic field-mediated sperm interaction," International Journal of Nanomedicine, vol. 4, 2009, pp. 55-64.
Kihara, K. et al. "A New Method to Generate Canine Seminal Emission and Its Application to Men: Direct Electrical Stimulation of the Vas Deferen,". Journal of Andrology, vol. 15, No. 5, Sep./Oct. 1994, pp. 479-483.
Khilwani, Barkha et al. "RISUG® as a male contraceptive: journey from bench to bedside," Basic and Clinical Andrology, 30:2, (2020), 12 pages.
Kloxin, April et al., "Photodegradable hydrogels for dynamic tuning of physical and chemical properties," Science, vol. 324, Apr. 3, 2009, pp. 59-63.
Koul, V. et al., "Reversibility With Sodium Bicarbonate of Styrene Maleic Anhydride, an Intravasal Injectable Contraceptive, in Male Rats," Contraception vol. 58(4), 1998, pp. 227-231.
Lahiri, Debrupa et al., "Graphene nanoplatelet-induced strengthening of ultrahigh molecular weight polyethylene and biocompatibility in vitro," ACS Applied Materials & Interfaces, vol. 4, 2012, pp. 2234-2241.
Lee, Wong Cheng et al., "Origin of enhanced stem cell growth and differentiation on graphene and graphene oxide," American Chemical Society, ACS Nano, vol. 5, No. 9, 2011, pp. 7334-7341.
Leocadio, D.E. et al., "Anatomical and histological equivalence of the human, canine, and bull vas deferens" The Canadian Journal of Urology, 18(3), Jun. 1, 2011, pp. 5699-5704.
Li, Jianyu et al. "Designing hydrogels for controlled drug delivery," Nat. Rev. Mater. vol. 1(12) pp. 1-17 (2016), Arthor Manuscript, HHS Public Access, 38 pages.
Li, Shunqiang et al., "The No-Scalpel Vasectomy," The Journal of Urology, vol. 145, Issue 2, Feb. 1991, pp. 341-344.
Lipshultz, Larry I. et al. "Techniques for Vasectomy Reversal," Urol. Clin. North Am. 36, 2009, pp. 375-382.
Liu, X. et al., "The Relationship Between the Vas Volume and the Anatomic Size of the Vas Deferens", Contraception, vol. 56{6}, 1997, pp. 391-394.
Lohiya, N.K. et al., "Preclinical evaluation for noninvasive reversal following long-term vas occlusion with styrene maleic anhydride in langur monkeys," Contraception, vol. 71(3), 2005, pp. 214-226.
Lohiya, N.K. et al., "RISUG: An intravasal injectable male contraceptive", Indian J Med Res 140 (Supplement), 2014, pp. 63-72.
Marks, Sheldon H. F., "Chapter 3—Predicting Reversal Success," pp. 9-35, Excerpt from *Manual of Vasovasostomy and Vasoepididymostomy*, (ed. Marks, S. H. F.) (Springer International Publishing, 2019). doi:10.1007/978-3-030-00455-2_3, 31 pages.
Mayans, David et al., "Neuromuscular ultrasonography: Quantifying muscle and nerve measurements," Phys. Med. Rehabil. Clin. N. Am. vol. 23(1), 2011, pp. 1-19.
Mckay, Craig S., et al., "Click Chemistry in Complex Mixtures: Bioorthogonal Bioconjugation," Chem Biol., vol. 21(9) Sep. 18, 2014, pp. 1-51.
Mehrali, Mehdi et al., "Mechanical and in vitro biological performance of graphene nanoplatelets reinforced calcium silicate composite," PLOS One, vol. 9, Issue 9, Sep. 2014, pp. 1-14.
Middleton, W.D. et al., "High-Resolution Sonography of the Normal Extrapelvic Vas Deferens," J Ultrasound Med., vol. 28, 2009, pp. 839-846.
Mossman, J. A., et al., "Variation in mean human sperm length is linked with semen characteristics," Human Reproduction, vol. 28, No. 1, Oct. 28, 2012, pp. 22-32.
Naahidi, Sheva et al. "Biocompatibility of hydrogel-based scaffolds for tissue engineering applications," Biotechnology Advances, vol. 35, (2017) pp. 530-544.
Naughton, C. K., et al., "The Use of URYX for Reversible Vasectomy in a Rabbit Model," Journal of Andrology, vol. 25, No. 4, Jul./Aug. 2004, pp. 545-553.

(56) References Cited

OTHER PUBLICATIONS

Noble, J. Alison et al., "Ultrasound image segmentation: a survey," IEEE Trans Med Imaging, vol. 25, No. 8, Aug. 2006 pp. 987-1010.
Norouzi, M. et al., "Injectable hydrogel-based drug delivery systems for local cancer therapy," Drug Discovery Today, vol. 21, No. 11, Nov. 2016, pp. 1835-1849.
WHO Laboratory Manual for the Examination of Human Semen and Sperm-Cervical Mucus Interaction. (Cambridge University Press, 1999).
Paefgen, Vera et al., "Evolution of contrast agents for ultrasound imaging and ultrasound-mediated drug delivery," Frontiers in Pharmacology, vol. 6, Article 197, Sep. 2015 pp. 1-16.
Rubinstein, Michael et al. "Polymer Physics," Oxford University Press, Jun. 26, 2003, 458 pgs.
Reddy, Neena M., et al., "Vasectomy-Related Changes on Sonographic Examination of the Scrotum," Journal of Clinical Ultrasound, vol. 32, 2004, pp. 394-398.
Robinette, W.B. "Ultrasound Contrast Agents", Journal of Diagnostic Medical Sonography, vol. 13, Supplement, Sep./Oct. 1997, pp. 29S-34S.
Roy, S. et al., "Polyelectrolyte polymer properties in relation to male contraceptive RISUG® action," Colloids and Surfaces B: Biointerfaces vol. 69, 2009, pp. 77-84.
RP Photonics Encyclopedia, "Silica Fibers" <online: https://www.rp-photonics.com/silica_fibers.html> at least as early as Oct. 2, 2017, 3 pgs.
Sadtler, Kaitlyn et al. "Design, clinical translation and immunological response of biomaterials in regenerative medicine," Nature Reviews Materials, vol. 1, Jul. 2016, pp. 1-17.
Sato, Kenji et al., "Spinal cord segments controlling the canine vas deferens and differentiation of the primate sympathetic pathways to the vas deferens," Microscopy. Research and Technique, vol. 42, (1998) pp. 390-397.
Shen, Z. L. et al., "Viscoelastic Properties of Isolated Collagen Fibrils," Biophysical Journal, vol. 100, Jun. 2011, pp. 3008-3015.
Sheynkin, Y. R. "History of Vasectomy." Urol. Clin. North Am. vol. 36, 2009, pp. 285-294.
Schmidt, S.S. et al. "Anatomical Sizes of the Human Vas Deferens After Vasectomy," Fertility and Sterility, vol. 27, No. 3, Mar. 1976, pp. 271-274.
Sigma-Aldrich "Safety Data Sheet" Version 4.2, for Product name: "Poly(vinyl alcohol-co-ethylene)", Product No. 414093, Revision Date: Jun. 25, 2014. Print Date: Mar. 27, 2017, 6 pgs.
Sigma-Aldrich "Syringe Needle Gauge Chart," <online: http://www.sigmaaldrich.com/chemistry/stockroom-reagents/learning-center/technicallibrary/needle-gauge-chart.html>, at least as early as Oct. 2, 2017, 2 pgs.
Singh, Sunilk et al., "Amine-Modified Graphene: Thrombo-Protective Safer Alternative to Graphene Oxide for Biomedical Applications," ACS NANO, vol. 6, No. 3, Jan. 1, 2012, pp. 2731-2740.
Soebadi, D. M. et al., "Intravasal injection of formed-in-place medical grade silicone for vas occlusion", International Journal of Andrology, vol. 18, Suppl. 1, 1995, pp. 45-52.
Staruch, Robert M.T. et al., "Injectable Pore-Forming Hydrogel Scaffolds for Complex Wound Tissue Engineering: Designing and Controlling Their Porosity and Mechanical Properties," Tissue Engineering, Part B, vol. 23, No. 3, Nov. 3, 2017, 16 pgs.
Stockton, D.M. et al. "No scalpel vasectomy: a technique for family physicians," Am Fam Physician, vol. 46, No. 4, Oct. 1992, 18 pgs.
Szabo, T.L. et al., "Ultrasound Transducer Selection in Clinical Imaging Practice," Journal of Ultrasound in Medicine, vol. 32(4), 2013, pp. 573-582.
Tan, H. et al. "Injectable, Biodegradable Hydrogels for Tissue Engineering Applications," Materials 2010, vol. 3, pp. 1746-1767.
Trussell, James "Contraceptive failure in the United States," Contraception vol. 83, No. 5, 397-404, May 2011, 14 pages.
Waller, D. et al., "Azoospermia in rabbits following an intravas injection of Vasalgel," Basic and Clinical Andrology, vol. 26:6, 2016, pp. 1-8.
VenaSeal™ Closure System, Product Code: VS-402 <online: https://www.accessdata.fda.gov/cdrh_docs/pdf14/p140018c.pdf> PT-11348-01 Rev D, Feb. 2015, 24 pages.
Waller, D. et al. "Reversibility of Vasalgel™ male contraceptive in a rabbit model," Basic and Clinical Andrology, vol. 27:8 (2017), 9 pages.
World Standards, "Plug, socket & voltage by country," <online: http://www.worldstandards.eu/electricity/plug-voltage-by-counlry/>, at least as early as Oct. 2, 2017, 16 pgs.
Zambon, J.V. et al., "Efficacy of percutaneous vas occlusion compared with conventional vasectomy", BJU International, vol. 86, 2000, pp. 699-706.
Zhang, Lu et al., "High strength graphene oxide/polyvinyl alcohol composite hydrogels," Journal of Materials Chemistry, vol. 21, 2011, pp. 10399-10406.
Zhao, Sheng-cai et al. "Intravasal injection of formed-in-place silcone rubber as a method of vas occlusion," International Journal of Andrology, vol. 15, Issue 6, 1992, pp. 460-464.
Zhao, Sheng-cai, "Vas Deferens Occlusion by Percutaneous Injection of Polyurethane Elastomer Plugs: Clinical Experience and Reversibility," Contraception, vol. 41(5), May 1990, pp. 453-459.
Zhou, Joe et al. "Optical Fiber Tips and Their Applications," Polymicro Technologies, <online: https://www.molex.com/mx_upload/superfamily/polymicro/pdfs/Optical_Fiber_Tips_and_Their_Applications_Nov_2007.pdf>, Nov. 2007, 5 pgs.
Hogan, et al., "Needle-free delivery of macromolecules through the skin using controllable jet injectors," Expert Opin Drug Deliv. 2015;12(10): pp. 1637-1648.
Ahmed, Enas M., "Hydrogel: Preparation, characterization, and applications: A review," Journal of Advanced Research, vol. 6, Issue 2, 2015, pp. 105-121.
Akbari et al. "Large-area graphene-based nanofiltration membranes by shear alignment of discotic nematic liquid crystals of graphene oxide," Nature Communications, published Mar. 7, 2016 (pp. 1-12).
Akram, Farhan, et al. "Segmentation of Regions of Interest Using Active Contours with SPF Function," Hindawi Publishing Corp., Computational Mathematical Methods in Medicine, vol. 2015; Article ID 710326, 15 pgs.
An, Lu, et al., "Paramagnetic hollow silica nanospheres for in vivo targeted ultrasound and magnetic resonance imaging," Biomaterials, vol. 35, Issue 20, 2014, pp. 5381-5392.
Amory, John K. "Male contraception," Fertility and Sterility, vol. 106, No. 6, Nov. 2016, pp. 1303-1309.
Amory, John K. "Development of Novel Male Contraceptives," Clin. Transl. Sci. 13 (2020), pp. 228-237.
Appel et al. "Self-assembled hydrogels utilizing polymer-nanoparticle interactions," Nature Communications, vol. 6, No. 6295, Feb. 19, 2015, [retrieved on Aug. 24, 2021]. Retrieved from the inernet <URL: https://www.nature.com/articles/ncomms7295.pdf?origin+ppub> pp. 1-9.
Avery, R. K. et al. "An injectable shear-thinning biomaterial for endovascular embolization," Science Translation Medicine, vol. 8, 365ra156 (2016) Nov. 16, 2016 (13 pgs.).
Bakaic, Emilia et al. "Injectable hydrogels based on poly(ethylene glycol) and derivatives as functional biomaterials" RSC Adv 5, 35469-35486 (2015), RSC Advances, Accepted Manuscript, <online: https://pubs.rsc.org/en/content/getauthorversionpdf/C4RA13581D>, 51 pages.
Daniels, Kimberly "Unmarried Men's Contraceptive Use at Recent Sexual Intercourse: United States, 2011-2015," Products, NCHS Data Brief, No. 284 <https://www.cdc.gov/nchs/products/databriefs/db284.htm> Aug. 2017, 8 pages.
Dressaire, Emilie, et al. "Interfacial Polygonal Nanopatterning of Stable Microbubbles," Science, vol. 320, Issue 5880, May 30, 2008, pp. 1198-1201.
El-Sherif, Dalia M., et al., "Development of a novel method for synthesis of a polymeric ultrasound contrast agent," Journal of Biomedical Materials Research Part A, (2003) 66A(2), 347-355.
Fan, Hailong et al., "Fabrication, mechanical properties, and biocompatibility of graphene-reinforced chitosan composites," Biomacromolecules, 11(9), 2010, pp. 2345-2351.

(56) References Cited

OTHER PUBLICATIONS

Flickinger, Charles J., "Alterations in the fine structure of the rat epididymis after vasectomy." The Anatomical Record, 173(3): 1972, pp. 377-299.
Flickinger, Charles J. et al., "The influence of vasovasostomy on testicular alterations after vasectomy in lewis rats," The Anatomical Record, 217(2), 1987, pp. 137-145.
Flickinger, Charles J., "Ultrastructure of the rat testis after vasectomy," The Anatomical Record, 174(4), 1972, pp. 477-493.
Fulton, David A., "Click chemistry gets reversible" Nature Chemistry, vol. 8, Oct. 2016, pp. 899-900.
Garmiak, R. et al., "Echocardiography of the aortic root," Investigative Radiology, vol. 3, Sep.-Oct. 1968, pp. 356-366.
Extended Search Report for European Application No. 19883448.3, dated Jul. 20, 2022.

\* cited by examiner

SYSTEMS AND METHODS FOR DELIVERING BIOMATERIALS

CROSS-REFERENCE TO RELATED APPLICATIONS

This application is a continuation of U.S. application Ser. No. 16/681,572, entitled "Systems and Methods for Delivering Biomaterials" filed Nov. 12, 2019, which claims benefit of priority to U.S. Provisional Application No. 62/760,650 entitled "Methods and Apparatus for Automated, Microvolume Delivery of Biomaterials," filed Nov. 13, 2018, all of which are incorporated herein by reference in their entirety.

BACKGROUND

The embodiments described herein relate generally to delivery devices and method of delivering biomaterials, and more particularly to controlled formation and delivery of a hydrogel to a body lumen.

Biomaterials are natural or synthetic materials (such as polymers) that are suitable for introduction into living tissues as a therapeutic (to treat, augment, repair, modify, or replace a tissue function of the body) or as a diagnostic. Biomaterials such as hydrogel implants have been shown to be useful for embolization, drug delivery, sealing, filling, and occlusion purposes. Hydrogels are highly hydrated polymer chains or networks that are able to absorb significant volumes of water and can have tunable mechanical properties. Biomaterials are often injectable, such as through a needle and/or catheter into the body. When injected, the material may gel or cross-link to form the implant. Many known systems, however, deliver multiple components into the body that are then cross-linked within the body after delivery. As such, the formation of the delivered hydrogel can be dependent on the in vivo conditions. Such known methods can therefore expose the patient to both the underlying components (i.e., the monomers or macromers that form the delivered hydrogel) and the delivered hydrogel itself. Such known methods may also require additional stimulation after delivery into the body to facilitate formation of the hydrogel. Such additional steps can result in longer procedures and increased variability (i.e., patient-to-patient) for the procedure.

Some known systems and methods include injecting and/or implanting a biomaterial product (e.g., a hydrogel) into a small area such as the lumen of a vessel or duct. For example, in some applications, the biomaterial will form an implant that acts as an occlusion or embolization of a lumen. The occlusion can be used for providing contraception to a subject by occluding the vas deferens, fallopian tube(s), or uterus. Such occlusions can also be used to occlude any other body part, such as ducts, tissues, interstitial spaces, or organs such as for drug delivery, spacing, sealing, embolizing, or bulking purposes. Known delivery systems, however, do not provide the desired safety, accuracy, precision, and/or repeatability, particularly when micro-volumes are involved. For example, some known delivery systems and methods are specifically designed to produce a spray (e.g., for wound healing, etc.). Because precise control over the total amount delivered, timing of the delivery, rate of delivery and/or delivery force is not often a significant concern for such applications. Such known systems are not suitable for applications where delivery of a small, precise amount to a specific location is desired.

Some known systems include a manual delivery device, such as a syringe that is operated by hand to deliver the components. Such manual systems, however, can often result in high variability. For example, the manual force applied by a physician on a hand delivery device can vary from procedure-to-procedure, and those variations are further magnified when considering different physicians performing the delivery procedure on different patients under different operating conditions. The variations in manual force applied on known hand delivery devices may drastically impact the total delivery amount administered to a patient and/or to a specific target area, particularly when the desired amount of compositions is very small (e.g., 0.001 mL to 1 mL). Insufficient delivery of compositions may result in the target area not being properly occluded, embolized, or sealed, which may result in a failed operation. On the other hand, excess delivery of compositions may lead to undesired occlusion, embolization, or sealing of non-target areas, and may be problematic if the non-target areas are sensitive to the compositions or need to remain free from occlusion, embolization, or sealing. Excess delivery of composition may also result in delivery of a final amount greater than the capacity of the target area, resulting in damage. For example, if the volume of the compositions delivered exceeds a capacity of a target vessel, the target vessel may rupture or the tissue may experience a histological response.

Some known delivery systems include an electromechanical delivery mechanism, and therefore do not rely on the practitioner to generate the delivery forces and control the timing and delivery process. For example, high-pressure jet injectors have been used to deliver high-viscous materials such as liquids and powders into the body for drug delivery purposes (see Nora C Hogan, Andrew J Taberner, Lynette A Jones & Ian W Hunter (2015), Needle-free delivery of macromolecules through the skin using controllable jet injectors, Expert Opinion on Drug Delivery, 12:10, 1637-1648). However, these devices are usually only applicable for injections into the epidermis and do not have a needle or catheter attachment to inject liquids or fluids into other confined areas of the body. Furthermore, they are incapable of injecting already-formed gelled materials.

Moreover, such known electronic systems do not include desired control over the velocity, flow rate, and/or force with which the compositions are delivered. Known systems that use an energy storage device (e.g., spring, electromechanical device, etc.) are designed for high volume delivery (e.g., greater than 1 mL) and may also deliver the product at a force that causes damage to target tissue. For example, a high rate delivery or large delivery force may scar or tear the target tissue; the overall safety and efficacy of the product is thus impacted. Such known systems may also deliver the underlying components too quickly such that the resulting biomaterial product to be delivered is not formed in the delivery system, but rather within or on the body tissue.

Known systems and methods of delivery also do not contemplate using a single cartridge for two distinct delivery operations, such as may be the case for procedures associated with symmetrical portions of the anatomy (i.e., where the procedure includes delivery to two target locations). For example, procedures in the reproductive health or reconstructive/plastic surgery may require delivery or implantation of biomaterials to two similar, contralateral, or related locations. Many known systems for delivering biomaterials are one-time use devices or cartridges and are not suitable for executing a precise and controlled delivery of a second micro-volume of a delivered biomaterial implant from the same cartridge.

Many known delivery systems and methods include a "priming" operation to prepare the components for delivery by removing dead volume, expelling undesirable air, and the like. Many known systems and methods include performing such priming operations with the delivery member (e.g., a needle) attached to the delivery device to remove excess air or fluid from the system before delivery. Such known methods, however, are not applicable when the components are formulated to be reacted within the delivery member in a short time period during delivery (i.e., to ensure that the delivered biomaterial product is formed upon being delivered). For example, conventional methods of priming may result in undesirable reactions that clog or otherwise compromise the delivery member prior to the actual delivery step. Such known methods and devices also do not support or contemplate procedures that perform a second priming function where two distinct delivery operations using a single cartridge is desired, as described above.

Moreover, such known systems and methods of priming do not accommodate methods for delivering a priming fluid into certain target locations immediately prior to delivery of the biomaterial product. Specifically, because known methods of priming are often aimed at eliminating air or other fluids, they do not allow for delivery of a priming fluid. Delivery of a priming fluid with a different echogenicity than the biomaterial can improve monitoring and tracking of the biomaterial during an operation. The priming fluid can also include other properties to prepare (e.g., pressurize, lubricate, cleanse, sterilize, assist in cross-linking) a target site for the delivery of the biomaterials.

Thus, a need exists for devices and methods for delivering biomaterials for medical procedures where a controlled rate and volume of the biomaterials is desired. More specifically, a need exists for devices and methods for controlled delivery of a formed hydrogel to a target site of a body where a controlled micro-volume is desired (e.g., 0.001 mL to 1 mL, or 1 µL-1,000 µL of volume). A need also exists to control the rate of delivery and total delivered amount of hydrogel to the target site in order to prevent or minimize damage to the target site and to ensure the amount delivered is safe and effective for occluding or embolizing the target site. A need exists for devices and methods for applying a controlled automated or semi-automated delivery force to replace inconsistent manual forces currently applied on hand delivery devices. A need further exists for devices and methods that support two distinct delivery operations in a single procedure from a single cartridge of components forming the hydrogel. A need also exists for delivery of a priming fluid prior to delivery of the formed hydrogel.

SUMMARY

Delivery devices for forming and delivering biomaterials from two components are described herein. In particular, apparatus and methods for performing controlled delivery of biomaterials into or onto a body part, such as a body lumen are described. More specifically, in some embodiments, the apparatus and methods are directed towards controlled delivery of micro-volumes, defined as 0.001 mL-1 mL (or 1 µL-1,000 µL) of volume (mL and cc are used interchangeably). However, one skilled in the art would appreciate that the apparatus and methods may also be used to perform controlled delivery of volumes greater than 1,000 µL.

In some embodiments, an apparatus includes a housing and a drive assembly. The housing is configured to receive at least a portion of a container assembly. The container assembly includes a first container containing a first component, a second container containing a second component, a first plunger, and a second plunger. The first and second containers are configured to be coupled to a connector. The drive assembly is configured to couple to the container assembly. The drive assembly is configured to move the first plunger within the first container to convey a portion of the first component from the first container and to move the second plunger within the second container to convey a portion of the second component from the second container. The drive assembly is configured to move the first plunger and the second plunger simultaneously for a time period to dispense the portion of the first component and the portion of the second component from the connector at an exit velocity within a predetermined velocity range during the time period.

In some embodiments, an apparatus includes a housing, a drive assembly, and an electronic control system. The housing is configured to receive at least a portion of a container assembly. The container assembly is configured to couple to a connector. The container assembly contains a first component and a second component, the first component being separate from the second component within the container assembly. The first component is formulated to be cross-linked with the second component to form a hydrogel. The drive assembly includes an electromechanical driver and a drive member. The electromechanical driver is configured to produce a drive force to move the drive member. The drive member is configured to engage the container assembly such that movement of the drive member causes a portion of the first component and a portion of the second component to be conveyed from the container assembly to the connector. The electronic control system includes a sensor and a drive module. The sensor is configured to produce a feedback signal associated with at least one of a position of the drive member, a velocity of the drive member, an acceleration of the drive member, or the drive force. The drive module is implemented in at least one of a memory or a processing device of the electronic control system. The drive module is configured to receive the feedback signal and produce, based on the feedback signal, a drive signal to maintain the drive force below a drive force threshold.

In some embodiments, an apparatus includes a housing, a drive assembly, and an electronic control system. The housing is configured to receive at least a portion of a container assembly. The container assembly is configured to be coupled to a connector. The container assembly contains a first component and a second component, the first component being separate from the second component within the container assembly. The first component is formulated to crosslink with the second component to form a hydrogel. The drive assembly includes an electromechanical driver and a drive member. The electromechanical driver is configured to produce a drive force to move the drive member. The drive member is configured to be operatively coupled to the container assembly such that movement of the drive member causes a portion of the first component and a portion of the second component to be conveyed from the container assembly to the connector. The electronic control system includes a sensor and a drive module. The sensor is configured to produce a feedback signal associated with at least one of a position of the drive member, a velocity of the drive member, an acceleration of the drive member, or the drive force. The drive module is implemented in at least one of a memory or a processing device of the electronic control system. The drive module is configured to receive the feedback signal and produce, based on the feedback signal, a drive signal to maintain the velocity of the drive member within a predetermined velocity range.

In some embodiments, an apparatus includes a housing, a drive assembly, and an electronic control system. The housing is configured to receive at least a portion of a container assembly. The container assembly includes a first container containing a first component and a second container containing a second component. The first container and the second container are configured to couple to a connector. The drive assembly includes a driver and a drive member. The driver is configured to produce a drive force to move the drive member. The drive member is configured to be operatively coupled to a first plunger and a second plunger such that movement of the drive member causes the first plunger to move within the first container to convey a portion of the first component from the first container and the second plunger to move within the second container to convey a portion of the second component from the second container. The electronic control system is within the housing. The electronic control system includes a first user input, a second user input, and a drive module. The drive module is implemented in at least one of a memory or a processing device of the electronic control system. The drive module is configured to produce a prime signal to cause the drive member to move a prime distance when the first user input is actuated. The drive module is configured to produce an injection signal to cause the drive member to move an injection distance when the second user input is actuated. The injection distance is associated with a predetermined delivered volume of the first component and the second component.

In some embodiments, an apparatus includes a first syringe assembly, a second syringe assembly, and a cartridge. The first syringe assembly includes a first syringe body and a first plunger movably disposed within the first syringe body. The first syringe body includes a first flange. The second syringe assembly includes a second syringe body and a second plunger movably disposed within the second syringe body. The second syringe body includes a second flange. The cartridge is configured to be removably coupled to a delivery device. The delivery device includes a drive assembly configured to move the first plunger within the first syringe body to convey a first component from the first syringe body and to move the second plunger within the second syringe body to convey a portion of the second component from the second syringe body. The cartridge defines a flange slot and includes a first retainer, a second retainer, and an engagement portion. The first retainer is configured to retain the first syringe body to the cartridge. The second retainer is configured to retain the second syringe to the cartridge. The flange slot is configured to receive the first flange and the second flange. The engagement portion is configured to engage a retainer of the delivery device to couple the cartridge to the delivery device in a fixed position relative to a home position associated with the drive assembly.

In some embodiments, a method of delivering a composition includes coupling an inlet of a connector to a container assembly. The container assembly includes a first component and a second component separate from the first component. The method includes priming the connector by conveying a first portion of the first component from the container assembly to a first outlet of the connector and conveying a first portion of the second component from the container assembly to a second outlet of the connector. The method includes coupling, after the priming, a delivery member to the connector to place the first outlet of the connector and the second outlet of the connector in fluid communication with a mixing volume defined by the delivery member. The method includes conveying, after the coupling the delivery member, a second portion of the first component and a second portion of the second component into the mixing volume. The second portion of the first component crosslinks with the second portion of the second component to form a hydrogel within the delivery member. The method includes conveying the hydrogel out of the delivery member via an outlet portion of the delivery member.

In some embodiments, a method of delivering a composition includes coupling a container assembly to a delivery device. The container assembly includes a first component and a second component separate from the first component. The delivery device includes a drive assembly. The method includes inserting a first delivery member into a first body lumen. The method includes coupling, after the inserting the first delivery member, the first delivery member to the container assembly. The method includes actuating the delivery device to cause the drive assembly to produce a first drive force to convey a first portion of the first component and a first portion of the second component from the container assembly and through the first delivery member. The first component crosslinks with the second component to form a first hydrogel within the first delivery member, and the first hydrogel is conveyed into the first body lumen. The method includes decoupling, after the actuating, the first delivery member from the container assembly. The method includes inserting a second delivery member into a second body lumen. The method includes coupling, after the inserting the second delivery member, the second delivery member to the container assembly. The method includes actuating the delivery device to cause the drive assembly to produce a second drive force to convey a second portion of the first component and a second portion of the second component from the container assembly and through the second delivery member. The first component crosslinks with the second component to form a second hydrogel within the second delivery member, and the second hydrogel being conveyed into the second body lumen.

In some embodiments, a method of delivering a composition to a body lumen within a body includes inserting an outlet portion of a delivery member into the body lumen. A coupling portion of the delivery member is outside of the body. The method includes coupling, after the inserting, a container assembly to the coupling portion of the delivery member. The container assembly includes a first component and a second component. The coupling is performed such that a bolus of air is retained within at least a portion of the delivery member. The method includes conveying the first component and the second component into the delivery member. The first component crosslinks with the second component to form a hydrogel within the delivery member. The conveying the first component and the second component into the delivery member causes the bolus of air to be delivered into the body lumen via the outlet portion of the delivery member. The method includes conveying, after the conveying the first component and the second component into the delivery member, the hydrogel into the body lumen via the outlet portion of the delivery member.

In some embodiments, a method of delivering a composition include conveying a first component stored in a first chamber of a container assembly to a first inlet of a connector coupled to the container assembly. The method includes conveying a second component stored in a second chamber of the container assembly to a second inlet portion of the connector. The method includes conveying the first component and the second component through an outlet portion the connector, into a mixing volume of a delivery member, and through the delivery member. The delivery member is removably coupled to the connector. The first component crosslinks with the second component to form a hydrogel within the delivery member such that the conveying the first component and the second component through the outlet portion causes the hydrogel to be conveyed out of an exit opening of the delivery member.

The description below and the accompanying figures will provide greater details on the various systems, methods and devices for delivering biomaterials.

DETAILED DESCRIPTION

Figure 1:
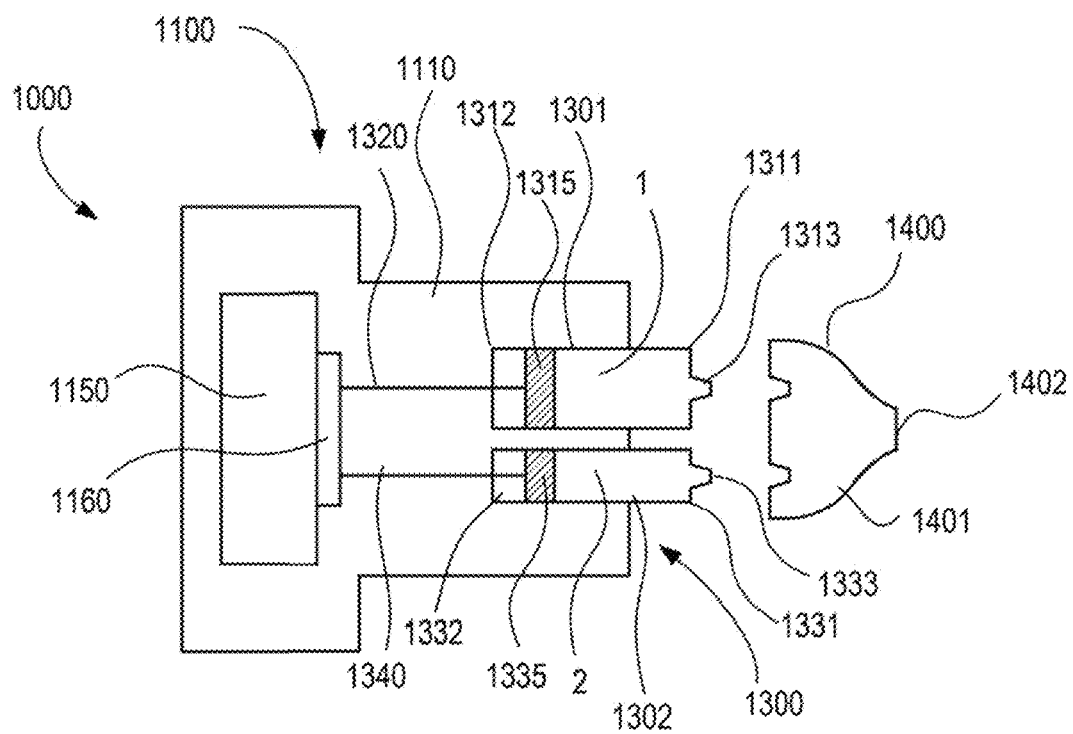
FIGS. 1 and 2 are schematic illustrations of a portion of a delivery system according to an embodiment.

In some embodiments, an apparatus includes a housing and a drive assembly. The housing is configured to receive at least a portion of a container assembly. The container assembly includes a first container containing a first component, a second container containing a second component, a first plunger, and a second plunger. The first and second containers are configured to be coupled to a connector. The drive assembly is configured to couple to the container assembly. The drive assembly is configured to move the first plunger within the first container to convey a portion of the first component from the first container and to move the second plunger within the second container to convey a portion of the second component from the second container. The drive assembly is configured to move the first plunger and the second plunger simultaneously for a time period to dispense the portion of the first component and the portion of the second component from the connector at an exit velocity within a predetermined velocity range during the time period.

In some embodiments, the predetermined velocity range is bounded by an upper velocity threshold and a lower velocity threshold. In some embodiments, the upper velocity threshold and the lower velocity threshold are such that a delivered volume of the portion of the first component and the portion of the second component is within a delivered volume range. In some embodiments, the delivered range is between about 5 microliters and about 1000 microliters. In some embodiments, lower velocity threshold is above zero.

In some embodiments, the drive assembly includes an electromechanical driver, a drive member, and an electronic control system. The drive member is configured to engage with the plunger assembly, and movement of the drive member is configured to move the first plunger and the second plunger. The electromechanical driver is configured to produce a drive force to move the drive member. The electronic control system is configured to control a drive member velocity to maintain the exit velocity within the predetermined velocity range during the time period.

In some embodiments, the electronic control system includes a sensor and a drive module. The sensor is configured to produce a feedback signal associated with at least one of a position of the drive member, a velocity of the drive member, an acceleration of the drive member, or a drive force applied via the drive member. The drive module is implemented in at least one of a memory or a processing device of the electronic control system. The drive module is configured to receive the feedback signal and produce, based on the feedback signal, a drive signal that adjusts a power applied to the electromechanical driver. In some embodiments, electronic control system is configured to maintain the drive force applied by the drive member on the plunger assembly below a force threshold. In some embodiments, the drive module is configured to produce an error signal when the power applied to the electromechanical driver exceeds a power threshold. In some embodiments, the force threshold is between about 0.1 Newtons and about 45 Newtons.

In some embodiments, the drive assembly includes at least one of a linear motor drive system, a screw drive system, a magnetic linear drive system, a rack and pinion drive system, or a pneumatic drive system. In some embodiments, the drive assembly includes an anti-backlash mechanism. The anti-backlash mechanism includes one or more of an anti-backlash gear, a selectively engageable spring mechanism, a damper mechanism, or a ratchet mechanism.

In some embodiments, the container assembly includes a cartridge including an engagement portion. The cartridge is configured to couple to the first container and the second container. The housing includes a container portion configured to receive the cartridge. The container portion includes a retainer configured to engage the engagement portion of the cartridge to removably retain the cartridge and the container assembly within the container portion of the housing in a fixed position relative to a home position associated with the drive assembly. In some embodiments, the engagement portion of the cartridge is a first engagement portion. The cartridge including a second engagement portion and the retainer of the container portion is a first retainer. The container portion includes a second retainer configured to engage the second engagement portion of the cartridge to inhibit movement of the container assembly relative to the housing in at least two directions. In some embodiments, at least one of the first retainer, the first engagement portion, the second retainer, or the second engagement portion is configured to deform to allow the cartridge to be removed from the container portion of the housing. In some embodiments, the container portion of the housing defines a container volume within which the cartridge is received. The apparatus further includes a cover. The cover is configured to move relative to the housing between a first position and a second position. The container volume is covered when the cover is in the first position, and the container volume is exposed when the cover is in the second position.

In some embodiments, the first component and the second component are each water soluble components. In some embodiments, the first component and the second component are capable of crosslinking to form the hydrogel. In some embodiments, the hydrogel formed by crosslinking the first component and the second component is at least 90 percent water. In some embodiments, the first component is characterized by having a first viscosity. The second component is characterized by a second viscosity, and the second viscosity is within 25 percent of the first viscosity. In some embodiments, the hydrogel formed by crosslinking the first component and the second component has a gelation time of less than 5 minutes.

In some embodiments, an apparatus includes a housing, a drive assembly, and an electronic control system. The housing is configured to receive at least a portion of a container assembly. The container assembly is configured to couple to a connector. The container assembly contains a first component and a second component, the first component being separate from the second component within the container assembly. The first component is formulated to be crosslinked with the second component to form a hydrogel. The drive assembly includes an electromechanical driver and a drive member. The electromechanical driver is configured to produce a drive force to move the drive member. The drive member is configured to engage the container assembly such that movement of the drive member causes a portion of the first component and a portion of the second component to be conveyed from the container assembly to the connector. The electronic control system includes a sensor and a drive module. The sensor is configured to produce a feedback signal associated with at least one of a position of the drive member, a velocity of the drive member, an acceleration of the drive member, or the drive force. The drive module is implemented in at least one of a memory or a processing device of the electronic control system. The drive module is configured to receive the feedback signal and produce, based on the feedback signal, a drive signal to maintain the drive force below a drive force threshold.

In some embodiments, the container assembly includes at least one container containing at least one of the first component or the second component. The container includes an elastomeric member to seal the first component or the second component within the container. The drive member is configured to move the elastomeric member within the container to convey at least one of the portion of the first component or the portion of the second component to the connector. The electromechanical driver is configured to produce a breakaway force for a first time period to initiate movement of the elastomeric member within the container. The drive force is produced for a second time period after the first time period. In some embodiments, the drive module is configured to produce, based on the feedback signal, the drive signal to maintain the breakaway force below a breakaway force threshold and the drive force below the drive force threshold. In some embodiments, the drive module is configured to produce the drive signal to maintain the velocity of the drive member within a predetermined velocity range during the second time period. In some embodiments, the drive module is configured to produce a completion signal to remove power applied to the electromechanical driver.

In some embodiments, the drive module is configured to produce an error signal when the drive force exceeds the drive force threshold. In some embodiments, the electronic control system includes an output device. The error signal causes the output device to produce at least one of a visual, audible, or tactile output. Additionally, the error signal causes a reduction in power applied to the electromechanical driver.

In some embodiments, the drive force threshold is between about 7 Newtons and about 12 Newtons. In some embodiments, the sensor is configured to measure at least one of a current or a voltage supplied to the electromechanical driver. The drive module is configured to determine the drive force based on the current or the voltage supplied to the electromechanical driver. The drive module is configured to produce the drive signal to adjust the current or the voltage.

In some embodiments, the sensor is a first sensor, the feedback signal is a first feedback signal, and the drive force threshold is a first drive force threshold. The electronic control system includes a second sensor configured to produce a second feedback signal indicating whether the connector is coupled to the container assembly. The drive module is configured to produce the drive signal to maintain the drive force below the first drive force threshold when the second feedback signal indicates that the connector is not coupled to the container assembly and below a second drive force threshold when the second feedback signal indicates that the connector is coupled to the container assembly. In some embodiments, the apparatus includes the connector. The connector is any one of an adapter, a y-connector, or a connector of a delivery member.

In some embodiments, an apparatus includes a housing, a drive assembly, and an electronic control system. The housing is configured to receive at least a portion of a container assembly. The container assembly is configured to be coupled to a connector. The container assembly contains a first component and a second component, the first component being separate from the second component within the container assembly. The first component is formulated to crosslink with the second component to form a hydrogel. The drive assembly includes an electromechanical driver and a drive member. The electromechanical driver is configured to produce a drive force to move the drive member. The drive member is configured to be operatively coupled to the container assembly such that movement of the drive member causes a portion of the first component and a portion of the second component to be conveyed from the container assembly to the connector. The electronic control system includes a sensor and a drive module. The sensor is configured to produce a feedback signal associated with at least one of a position of the drive member, a velocity of the drive member, an acceleration of the drive member, or the drive force. The drive module is implemented in at least one of a memory or a processing device of the electronic control system. The drive module is configured to receive the feedback signal and produce, based on the feedback signal, a drive signal to maintain the velocity of the drive member within a predetermined velocity range. In some embodiments, the drive module is configured to produce the drive signal to adjust one of a current or a voltage supplied to the electromechanical driver.

In some embodiments, an apparatus includes a housing, a drive assembly, and an electronic control system. The housing is configured to receive at least a portion of a container assembly. The container assembly includes a first container containing a first component and a second container containing a second component. The first container and the second container are configured to couple to a connector. The drive assembly includes a driver and a drive member. The driver is configured to produce a drive force to move the drive member. The drive member is configured to be operatively coupled to a first plunger and a second plunger such that movement of the drive member causes the first plunger to move within the first container to convey a portion of the first component from the first container and the second plunger to move within the second container to convey a portion of the second component from the second container. The electronic control system is within the housing. The electronic control system includes a first user input, a second user input, and a drive module. The drive module is implemented in at least one of a memory or a processing device of the electronic control system. The drive module is configured to produce a prime signal to cause the drive member to move a prime distance when the first user input is actuated. The drive module is configured to produce an injection signal to cause the drive member to move an injection distance when the second user input is actuated. The injection distance is associated with a predetermined delivered volume of the first component and the second component.

In some embodiments, the electronic control system includes an output device. The drive module is configured to produce an error signal on the condition that the second user input is actuated without the first user input having been actuated. The error signal causes the output device to produce any one of a visual, audible, or tactile output. In some embodiments, the error signal disables the injection signal.

In some embodiments, the electronic control system includes a sensor and an output device. The sensor is configured to produce a feedback signal indicating whether the connector is coupled to the container assembly. The drive module is configured to produce an error signal when the feedback signal indicates that the connector is not coupled to the container assembly. The error signal causes the output device to produce any one of a visual, audible, or tactile output. In some embodiments, the error signal disables at least one of the prime signal or the injection signal.

In some embodiments, the prime signal is a first prime signal and the prime distance is a first prime distance. The drive module is configured to produce the first prime signal to cause the drive member to move the first prime distance when the first user input is actuated at a first time. The drive module configured to produce a second prime signal to cause the drive member to move a second prime distance when the first user input is actuated at a second time, the second prime distance being different from the first prime distance.

In some embodiments, the electronic control system includes a sensor configured to produce a feedback signal associated with at least one of a position of the drive member, a velocity of the drive member, an acceleration of the drive member, or the drive force. The drive module is configured to receive the feedback signal and adjust, based on the feedback signal, the injection signal to maintain the velocity of the drive member within a predetermined velocity range.

In some embodiments, the electronic control system includes a sensor configured to produce a feedback signal associated with at least one of a position of the drive member, a velocity of the drive member, an acceleration of the drive member, or the drive force. The drive module is configured to receive the feedback signal and adjust, based on the feedback signal, the injection signal to maintain the drive force below a drive force threshold.

In some embodiments, an apparatus includes a first syringe assembly, a second syringe assembly, and a cartridge. The first syringe assembly includes a first syringe body and a first plunger movably disposed within the first syringe body. The first syringe body includes a first flange. The second syringe assembly includes a second syringe body and a second plunger movably disposed within the second syringe body. The second syringe body includes a second flange. The cartridge is configured to be removably coupled to a delivery device. The delivery device includes a drive assembly configured to move the first plunger within the first syringe body to convey a first component from the first syringe body and to move the second plunger within the second syringe body to convey a portion of the second component from the second syringe body. The cartridge defines a flange slot and includes a first retainer, a second retainer, and an engagement portion. The first retainer is configured to retain the first syringe body to the cartridge. The second retainer is configured to retain the second syringe to the cartridge. The flange slot is configured to receive the first flange and the second flange. The engagement portion is configured to engage a retainer of the delivery device to couple the cartridge to the delivery device in a fixed position relative to a home position associated with the drive assembly.

In some embodiments, the retainer of the delivery device is a first retainer and the engagement portion of the cartridge is a first engagement portion. The cartridge includes a second engagement portion configured to engage a second retainer of the delivery device to inhibit movement of the cartridge relative to the delivery device. In some embodiments, the apparatus further includes a plunger link configured to be coupled to an end of the first plunger and an end of the second plunger. The plunger link includes a contact surface against which the drive assembly of the delivery device exerts a drive force to move the first plunger within the first syringe body and the second plunger within the second syringe body. In some embodiments, the apparatus further includes a connector having a first inlet, a second inlet, and an outlet. The first inlet is configured to couple to a tip of the first syringe body. The second inlet is configured to couple to a tip of the second syringe body. The outlet of the connector is configured to be removably coupled to a delivery member.

In some embodiments, a method of delivering a composition includes coupling an inlet of a connector to a container assembly. The container assembly includes a first component and a second component separate from the first component. The method includes priming the connector by conveying a first portion of the first component from the container assembly to a first outlet of the connector and conveying a first portion of the second component from the container assembly to a second outlet of the connector. The method includes coupling, after the priming, a delivery member to the connector to place the first outlet of the connector and the second outlet of the connector in fluid communication with a mixing volume defined by the delivery member. The method includes conveying, after the coupling the delivery member, a second portion of the first component and a second portion of the second component into the mixing volume. The second portion of the first component crosslinks with the second portion of the second component to form a hydrogel within the delivery member. The method includes conveying the hydrogel out of the delivery member via an outlet portion of the delivery member.

In some embodiments, the container assembly includes a first container containing the first component and a second container containing the second component, the second container separate from the first container. The coupling the inlet of the connector to the container assembly includes connecting a first inlet of the connector to the first container and a second inlet of the connector to the second container.

In some embodiments, the delivery member is a first delivery member and the hydrogel is a first hydrogel. The method includes removing the first delivery member from the connector. The method includes priming the connector, after removing the first delivery member, by conveying a third portion of the first component to the first outlet of the connector and conveying a third portion of the second component to the second outlet of the connector. The method includes coupling a second delivery member to the connector to place the first outlet and the second outlet in fluid communication with a second mixing volume defined by the second delivery member. The method includes conveying a fourth portion of the first component and a fourth portion of the second component to the second mixing volume, the fourth portion of the first component crosslinking with the fourth portion of the second component to form a hydrogel in the second mixing volume. In some embodiments, the delivery member is any one of a catheter, needle, or over-the-needle catheter.

In some embodiments, the method includes conveying the second hydrogel out of the second delivery member via an outlet portion of the second delivery member. In some embodiments, the conveying of the first hydrogel out of the first delivery member includes conveying the hydrogel to a first body lumen. The conveying of the second hydrogel out of the second delivery member includes conveying the hydrogel to a second body lumen, the second body lumen being different from the first body lumen.

In some embodiments, the conveying of the hydrogel out of the delivery member includes conveying the hydrogel to a body lumen. In some embodiments, the body lumen is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space. In some embodiments, the hydrogel conveyed to the body lumen at least partially occludes the body lumen. In some embodiments, the conveying the hydrogel out of the delivery member is performed in less than 30 seconds. In some embodiments, the conveying the hydrogel out of the delivery member includes conveying between about 50 microliters and about 200 microliters in between about 5 seconds and about 20 seconds.

In some embodiments, the conveying of the second portion of the first component and the second portion of the second component to the mixing volume of the delivery member includes conveying equal parts of the second portion of the first component and the second portion of the second component.

In some embodiment, the conveying of the second portion of the first component and the second portion of the second component to the mixing volume of the delivery member is performed by an electromechanical driver of a drive assembly of a delivery device. In some embodiments, the delivery device includes an electronic control system. The conveying the hydrogel out of the delivery member includes producing via the electronic control system a drive signal that controls the electromechanical driver to maintain an exit force of the hydrogel being conveyed out of the delivery member below an exit force threshold. In some embodiments, the delivery device includes an electronic control system. The conveying of the hydrogel out of the delivery member is performed over a time period to produce a delivered volume of the hydrogel. The conveying of the second portion of the first component and the second portion of the second component into the mixing volume and the conveying the hydrogel out of the delivery member includes producing via the electronic control system a drive signal that controls the electromechanical driver to maintain a velocity of the hydrogel within the delivery member within a predetermined velocity range during the time period. In some embodiments, the priming of the connector includes energizing the electromechanical driver to actuate a plunger assembly coupled to the container assembly.

In some embodiments, the coupling of the delivery member is performed such that a bolus of air is within the mixing volume. The conveying of the hydrogel out of the delivery member includes conveying the hydrogel to a body lumen. The conveying of the second portion of the first component and the second portion of the second component into the mixing volume causes the bolus of air to be delivered into the body lumen before the hydrogel is conveyed to the body lumen. In some embodiments, the coupling of the delivery member is performed such that a bolus of air is within the mixing volume. The conveying of the hydrogel out of the delivery member includes conveying the hydrogel to a body lumen. The conveying of the second portion of the first component and the second portion of the second component into the mixing volume causes the bolus of air to be delivered into the body lumen before the hydrogel is conveyed to the body lumen. In some embodiments, the coupling of the delivery member is performed such that a bolus of air is within the mixing volume. The conveying of the hydrogel out of the delivery member includes conveying the hydrogel to a body lumen. The conveying of the second portion of the first component and the second portion of the second component into the mixing volume causes the bolus of air to be delivered into the body lumen before the hydrogel is conveyed to the body lumen. In some embodiments, the second portion of the first component crosslinks with the second portion of the second component to form the hydrogel in less than 60 seconds.

In some embodiments, a method of delivering a composition includes coupling a container assembly to a delivery device. The container assembly includes a first component and a second component separate from the first component. The delivery device includes a drive assembly. The method includes inserting a first delivery member into a first body lumen. The method includes coupling, after the inserting the first delivery member, the first delivery member to the container assembly. The method includes actuating the delivery device to cause the drive assembly to produce a first drive force to convey a first portion of the first component and a first portion of the second component from the container assembly and through the first delivery member. The first component crosslinks with the second component to form a first hydrogel within the first delivery member, and the first hydrogel is conveyed into the first body lumen. The method includes decoupling, after the actuating, the first delivery member from the container assembly. The method includes inserting a second delivery member into a second body lumen. The method includes coupling, after the inserting the second delivery member, the second delivery member to the container assembly. The method includes actuating the delivery device to cause the drive assembly to produce a second drive force to convey a second portion of the first component and a second portion of the second component from the container assembly and through the second delivery member. The first component crosslinks with the second component to form a second hydrogel within the second delivery member, and the second hydrogel being conveyed into the second body lumen.

In some embodiments, a method of delivering a composition to a body lumen within a body includes inserting an outlet portion of a delivery member into the body lumen. A coupling portion of the delivery member is outside of the body. The method includes coupling, after the inserting, a container assembly to the coupling portion of the delivery member. The container assembly includes a first component and a second component. The coupling is performed such that a bolus of air is retained within at least a portion of the delivery member. The method includes conveying the first component and the second component into the delivery member. The first component crosslinks with the second component to form a hydrogel within the delivery member. The conveying the first component and the second component into the delivery member causes the bolus of air to be delivered into the body lumen via the outlet portion of the delivery member. The method includes conveying, after the conveying the first component and the second component into the delivery member, the hydrogel into the body lumen via the outlet portion of the delivery member.

In some embodiments, the bolus of air has a selected volume sufficient to dilate the body lumen before the hydrogel is conveyed into the body lumen. In some embodiments, the selected volume is between 0.1 mL and 10 mL.

In some embodiments, the hydrogel is echogenic and the method includes identifying the bolus of air via an image of the body lumen, such as by ultrasound. In some embodiments, the body lumen is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space.

In some embodiments, the conveying of the first component and the second component to the delivery member is performed by an electromechanical driver of a drive assembly of a delivery device. In some embodiments, the delivery device includes an electronic control system. The conveying the hydrogel into the body lumen includes producing via the electronic control system a drive signal that controls the electromechanical driver to maintain an exit force of the hydrogel being conveyed out of the delivery member below an exit force threshold. In some embodiments, the delivery device includes an electronic control system. The conveying of the hydrogel into the body lumen is performed over a time period to produce a delivered volume of the hydrogel. The conveying of the first component and the second component into the delivery member and the conveying the hydrogel into the body lumen includes producing, via the electronic control system, a drive signal that controls the electromechanical driver to maintain a velocity of the hydrogel within the delivery member within a predetermined velocity range during the time period.

In some embodiments, the method includes priming, prior to the coupling of the container assembly to the coupling portion of the delivery member, an outlet portion of the container assembly by conveying a portion of the first component from the container assembly to a first outlet of the container assembly and by conveying a portion the second component from the container assembly container to a second outlet of the container assembly.

In some embodiments, a method of delivering a composition include conveying a first component stored in a first chamber of a container assembly to a first inlet of a connector coupled to the container assembly. The method includes conveying a second component stored in a second chamber of the container assembly to a second inlet portion of the connector. The method includes conveying the first component and the second component through an outlet portion the connector, into a mixing volume of a delivery member, and through the delivery member. The delivery member is removably coupled to the connector. The first component crosslinks with the second component to form a hydrogel within the delivery member such that the conveying the first component and the second component through the outlet portion causes the hydrogel to be conveyed out of an exit opening of the delivery member.

In some embodiments, the hydrogel is conveyed out of the exit opening of the delivery member into a body lumen to at least partially occlude the body lumen. In some embodiments, the body lumen is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space.

In some embodiments, the conveying of the first component and the second component to the mixing volume includes conveying equal parts of the first component and the second component.

In some embodiments, the first component and the second component are formulated such that the hydrogel has a gelation time. The conveying of the first component and the second component through the outlet portion, into the mixing volume, and through the delivery member is performed within a flow rate range that is based on the gelation time such that the hydrogel is fully formed within the delivery member before being conveyed out of the exit opening. In some embodiments, the conveying of the first component and the second component through the outlet portion, into the mixing volume, and through the delivery member is performed by an electromechanical driver of a drive assembly of a delivery device. The delivery device includes an electronic control system. The conveying of the first component and the second component through the outlet portion, into the mixing volume, and through the delivery member includes producing via the electronic control system a drive signal that controls the electromechanical driver to maintain a velocity of the hydrogel within the delivery member within a predetermined velocity range. In some embodiments, the conveying of the first component and the second component through the outlet portion, into the mixing volume, and through the delivery member is performed over a time period to produce a delivered volume of the hydrogel.

In some embodiments, the first component is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole.

In some embodiments, an injection device includes a device body, one or more syringes, a controller, and one or more input devices. The device body includes a shaft, a handle, and an injection trigger. Each of the one or more syringes includes a plunger in operable connection with one or more actuator disposed within the device body. The controller is in operable connection with the actuator. The one or more input devices are in operable connection with the controller, and the input devices are capable of priming or injecting fluid inside the one or more syringes.

In some embodiments, the one or more input devices are disposed on an outer portion of the device body. In some embodiments, the one or more syringes, actuator, and controller are disposed within the device body. The one or more syringes includes two syringes in operable connection with the one or more actuator. In some embodiments, one or more or each plunger is in operable connection with the actuator by way of a piston.

In some embodiments, the injection device includes a connector connected to the one or more syringes. The connector is a Y-connector connected to the two syringes. The one or more syringes, actuator, and controller are disposed within the shaft. In some embodiments, the injection device includes a power supply. In some embodiments, the injection device includes a needle hub disposed at the end of the connector. The injection device includes a mixing chamber, optionally disposed between the connector and the needle hub.

In some embodiments, the actuator is a stepper motor or a torque motor. The injection device is capable of injecting micro-volumes in the range of 1 µL-1000 µL. The injection device includes a pressure-sensitive sensor in operable connection with the controller and capable of being activated by the trigger. The pressure-sensitive sensor is capable of activating the controller to send a signal to the actuator to drive the piston. In some embodiments, the controller comprises a processor and a memory. The memory comprises a set of computer-readable instructions capable of controlling the rate, acceleration, force, and/or time period that the actuator drives the piston. In some embodiments, the rate, acceleration, force, and/or time period that the actuator drives the piston are programmable. In some embodiments, the injection device includes a user interface capable of programming the injection device, such as the rate, force, and/or time period that the actuator drives the piston.

In some embodiments, the injection device is capable of adding a solvent to a solid in a container to dissolve the solid prior to any injection steps. The injection device is capable of degassing liquids. The injection device is capable of delivering different volumes in states such as gases, liquids, gels, and solids like powders or particulates. The injection device is capable of securing and changing out needles/catheters from the tip. In some embodiments, the injection device is capable of mixing multiple substances within a single container and delivering multiple volumes from the container to a target location.

The term "about" when used in connection with a referenced numeric indication means the referenced numeric indication plus or minus up to 10% of that referenced numeric indication. For example, "about 100" means from 90 to 110.

The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range.

As used herein, the term "biomaterial component" (also referred to as "component") includes any substance that is used in connection with any of the systems or delivery devices described herein to form a delivered biomaterial product. For example, a component can include a small molecule, catalyst, peptide, protein, enzyme, nucleotide (or derivatives of), short chains of nucleotides (or derivatives of), long chains of nucleotides (or derivatives of), monosaccharides (or derivatives of), disaccharides (or derivatives of), trisaccharides (or derivatives of), oligo saccharides (or derivatives of), polysaccharides (or derivatives of), monomer, oligomer, macromer, or polymer that can be cross-linked with another component to form a delivered product (e.g., hydrogel). A component can include a mixture or solution of one or more constituents (e.g., a polymer and a solvent). A component can include such constituents regardless of their state of matter (e.g., solid, liquid or gas). A component can include both active constituents and inert constituents. For example, in some embodiments, a component can include certain polymers that can form a delivered product, as well as a medicament or other active ingredient. By way of another example, in some embodiments a component can include drugs, including but not limited to, small molecule drugs and biologics. In other embodiments, a component can include certain constituents to impart desired properties to the delivered product, including constituents that facilitate the delivered product being echogenic, radiopaque, radiolucent, or the like.

The term "biomaterial product," "delivered biomaterial product," or "delivered product" includes any substance that is delivered by any of the systems or delivery devices described herein. For example, a delivered product can a biomaterial that is formed from multiple biomaterial components and delivered with any of the delivery systems described herein and then delivered to target locations. Thus, a delivered product can be the implant or structure that is formed with the system by multiple biomaterial components that react together or assemble into higher order structures via covalent and/or non-covalent bonds, and that is delivered by the system. In certain situations, the biomaterial can be delivered by the system in a fully formed state to a target location. Although a delivered product can be considered fully formed (i.e., the chemical reactions between the biomaterial components are completed), it can still undergo certain changes (e.g., in vivo changes) after delivery. For example, a delivered biomaterial product can continue to absorb water and/or swell and/or can expel impurities. In some embodiments, a delivered biomaterial product can be a hydrogel that is formed by crosslinking of two or more biomaterial components. The term "hydrogel" can refer to any water-swollen (majority, >50%, of material mass is water), and cross-linked polymeric network produced by the reaction of one or more components (e.g., polymers, monomers) and/or a polymeric material that exhibits the ability to swell and retain a significant fraction of water within its structure, but will not dissolve in water.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method)

Figure 2:
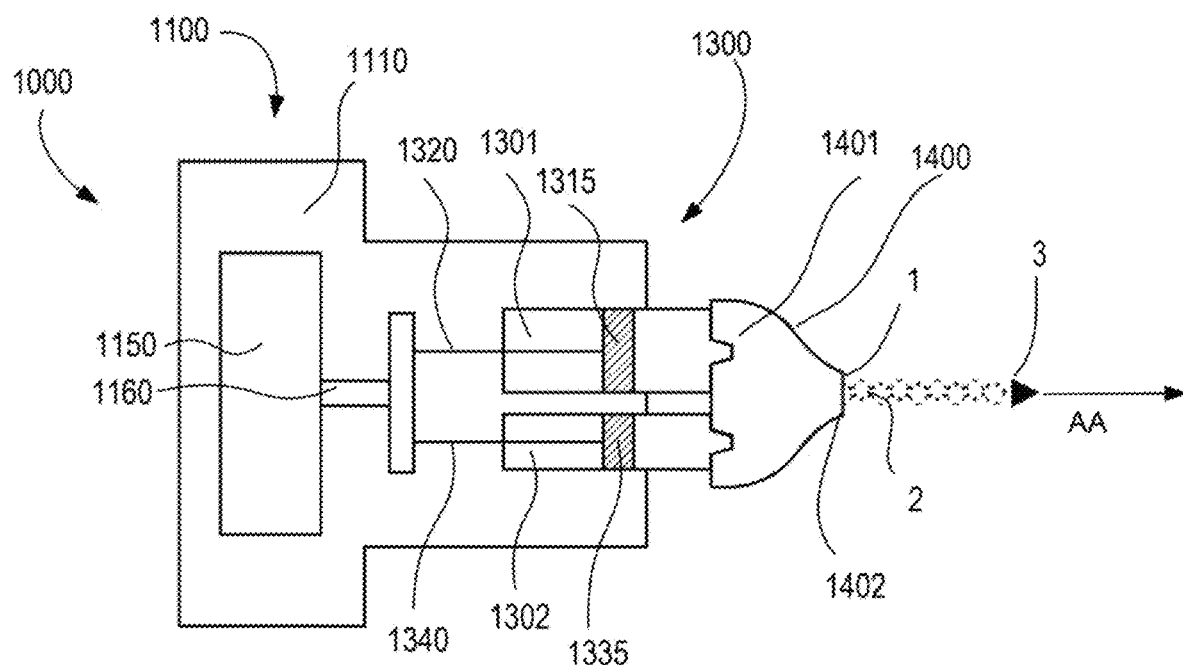
Figure 3:
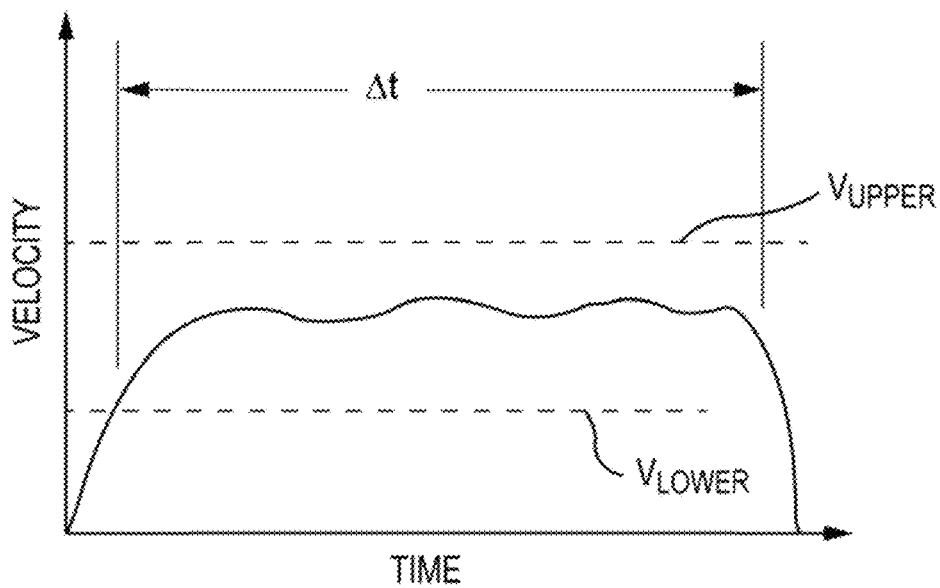
FIGS. 3 and 4 are plots showing sample velocity profiles of the biomaterial components during use of the delivery system of FIG. 2.
Figure 4:
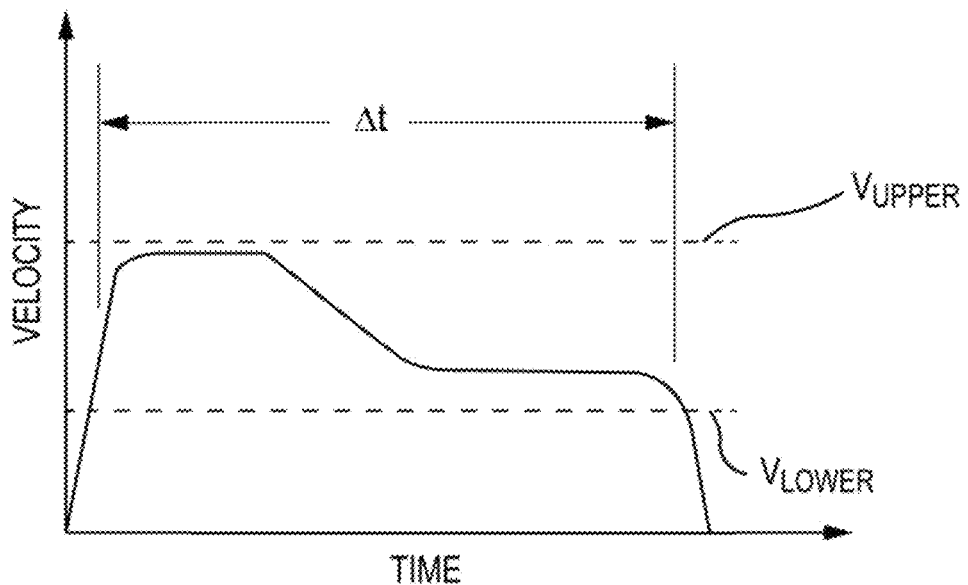
Figure 5:
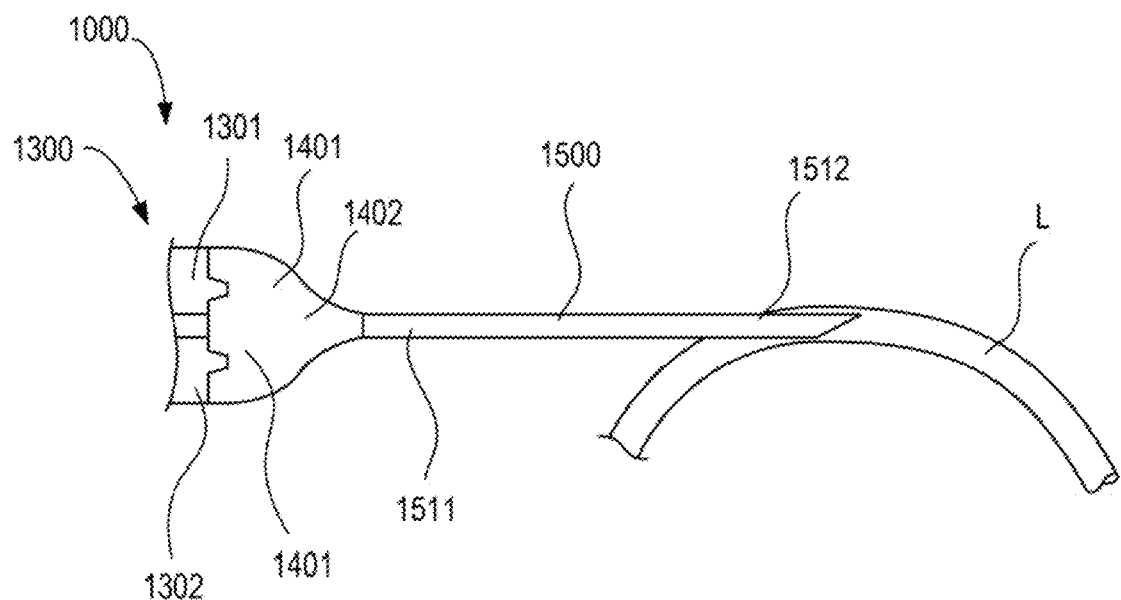
FIG. 5 is schematic illustration of a portion of the delivery system shown in FIGS. 1 and 2 inserted into a body lumen according to an embodiment.
Figure 6:
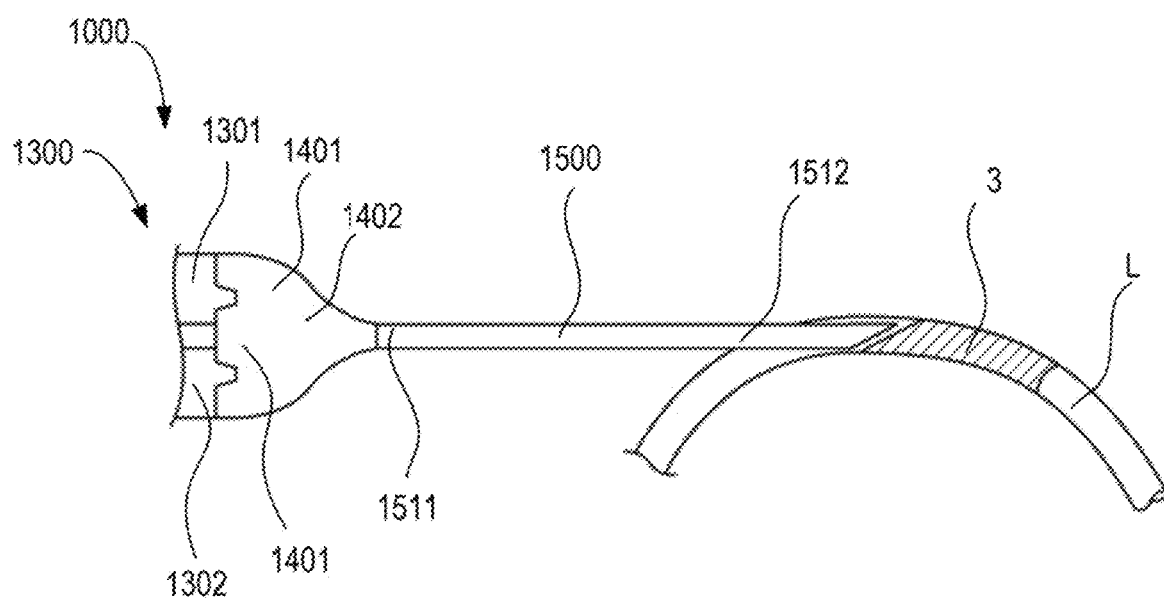
FIG. 6 is a schematic illustration of the delivery system of FIG. 5 delivering biomaterial components to the body lumen.
Figure 7:
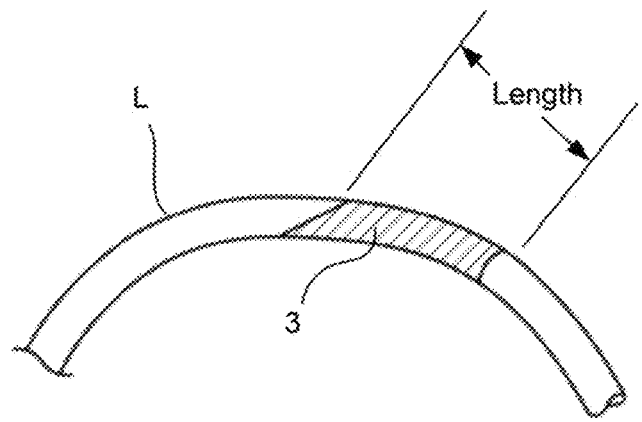
FIG. 7 is a schematic illustration of the biomaterial components placed within the body lumen after the delivery system of FIG. 5 has been withdrawn from the body lumen.

FIGS. 1 and 2 are schematic illustrations of a portion of a system 1000 (also referred to as a delivery system) according to an embodiment. As described herein, the system 1000 is configured to convey and combine multiple biomaterial components that form a biomaterial product that is delivered to a target location. FIGS. 3 and 4 are plots showing sample velocity profiles of the biomaterial components during use of the system 1000 and FIGS. 5-7 show the system 1000 being used to deliver a biomaterial product 3 (also referred to as the product) to a target location (specifically, within a body lumen L). The system 1000 includes a delivery device 1100, a container assembly 1300, a connector 1400, and a delivery member 1500 (see FIGS. 5 and 6).

The delivery device 1100 includes a housing 1110 and a drive assembly 1150. The housing 1110 is configured to receive at least a portion of the container assembly 1300. The housing 1110 can also contain the drive assembly 1150. The housing 1110 can be made from any suitable material or materials and can provide any suitable structural components to receive and/or retain the portion of the container assembly 1300 and perform any of the functions described herein. For example, in some embodiments, the housing 1110 can be constructed from multiple components that are joined together (e.g., via a hinged joint, a mechanical fastener or the like) to surround and/or secure the container assembly 1300. In some embodiments, for example, the housing 1100 (or any of the housings described herein) can include a movable lid or cover that can reveal a container portion within which the container assembly 1300 can be removably coupled. In use, the lid or cover can be closed to secure the container assembly 1300 within the housing 1110. In some embodiments, the housing 1100 (or any of the housings described herein) can include a lock member (or set of lock members) that retain the container assembly 1300 within the housing and can prevent premature and/or undesired removal of the container assembly 1300.

The drive assembly 1150 can be any suitable assembly or mechanism that produces a drive force to convey the first biomaterial component 1 (also referred to as the first component), or the second biomaterial component 2 (also referred to as the second component), or both the first component 1 and the second component 2 from the container assembly 1300 as described herein. More specifically, the drive assembly 1150 can produce the drive force and/or convey the components within a desired velocity range, force range, and/or range of flow rates. By controlling the delivery characteristics of the first component 1, the second component 2, and/or the delivered product 3, the drive assembly 1150 can repeatably deliver an accurate amount of the delivered product 3 to the target location. This, in turn, can lead to more consistent and improved outcomes. Controlling the delivery characteristics can also ensure that any desired reactions between the first component 1 and the second component 2 (e.g., a cross-linking reaction) are completed within the system 1000. Said another way, controlling the delivery characteristics can ensure that the delivered product 3 is fully formed within the system (e.g., the delivery member 1500), thereby ensuring that that the first component 1 and the second component 2 are not delivered while the product 3 is still yet to be formed (or is only partially formed). Controlling the delivery characteristics can also limit potential damage to the target tissue. Such damage can be caused by delivering an improper amount of the product or delivering the product too fast or at a force that causes tissue damage. Finally, controlling the delivery characteristics can also limit clogging or blockage within the system 1000 (e.g., the delivery member 1500).

As shown, the drive assembly 1150 includes a drive member 1160 that is operably coupled to the container assembly 1300 such that, upon actuation, the drive assembly 1150 can convey the first component 1 and the second component 2 from the container assembly 1300. The drive assembly 1150 can include any suitable mechanism for producing the drive force. For example, in some embodiments, the drive assembly can include an electromechanical driver (not shown in FIGS. 1 and 2) to produce the drive force. Such electromechanical drivers can include, for example, a motor-driven linear actuator, a hydraulic actuator (e.g., that includes a pump driven by an electronic component), a magnetic-based actuator, a pneumatic actuator that includes an electromechanical valve to control a pressure applied to the drive member 1160, or any other suitable electromechanical driver of the types described herein. In some embodiments, the drive assembly 1150 and/or the delivery device 1100 can include an electronic control system (not shown) that controls the electromechanical driver and any other aspect of the drive assembly to control the delivery characteristics of the first component 1, the second component 2, and/or the delivered product 3, as described herein. For example, in some embodiments, the electronic control system can be similar to the electronic control system 2200 described herein.

The container assembly 1300 includes a first container 1301 and a second container 1302, and can be coupled to and/or received within the housing 1110. The first container 1301 has a first end portion 1311, a second end portion 1312, and includes an elastomeric member (or stopper) 1315 therein. The first container 1301 defines a volume that is bounded on one side by the elastomeric member 1315 and that contains a first component 1. The first container 1301 includes a first plunger 1320 having an end portion movably disposed within the first container 1301 such that movement of the first plunger 1320 will cause movement of the elastomeric member 1315 to convey the first component 1 from the first container 1301. The opposite end of the first plunger 1320 is operably coupled to (e.g., is configured to engage) the drive member 1160. The second container 1302 has a first end portion 1331, a second end portion 1332, and includes an elastomeric member (or stopper) 1335 therein. The second container 1302 defines a volume that is bounded on one side by the elastomeric member 1335 and that contains a second component 2. The second container 1302 includes a second plunger 1340 having an end portion movably disposed within the second container 1302 such that movement of the second plunger 1340 will cause movement of the elastomeric member 1335 to convey the second component 2 from the second container 1302. The opposite end of the second plunger 1340 is operably coupled to (e.g., is configured to engage) the drive member 1160. In some embodiments, the elastomeric member is made of a butyl rubber such as chlorobutyl or bromobutyl. In some embodiments, the elastomeric member can be coated with a film or other coatings such as ethylene tetrafluoroethylene (ETFE) or fluorinated ethylene propylene (FEP).

The first container 1301 and the second container 1302 (and any of the containers described herein) can be any suitable containers. For example, the first container 1301 and/or the second container 1302 can be a cartridge, an ampule, or a syringe. Moreover, the first container 1301 and the second container 1302 (and any of the containers described herein) can be of any suitable size and can be constructed from any suitable material such a type I borosilicate glass. For example, in some embodiments, the first container 1301 and the second container 1302 can have different sizes (e.g., different diameters). In this manner, the container assembly can accommodate delivering different volumes of the first component 1 and the second component 2 while maintaining a constant stroke length. In other embodiments, the first container 1301 and the second container 1302 can be the same size.

The first component 1 and the second component 2 can be any of the biomaterial components described herein. For example, in some embodiments, the first component 1 and the second component 2 can each be a water soluble component (e.g., monomer, macromer, polymer, or the like) that is capable of crosslinking (e.g., with the other component) to form a hydrogel (as the delivered biomaterial product). In some embodiments, the first component 1 and the second component 2 are formulated such that the resulting hydrogel has a gelation time of less than 5 minutes. In other embodiments, the first component 1 and the second component 2 are formulated such that the resulting hydrogel has a gelation time of less than 2 minutes. In other embodiments, the first component 1 and the second component 2 are formulated such that the resulting hydrogel has a gelation time of less than 1 minute. In yet other embodiments, the first component 1 and the second component 2 are formulated such that the resulting hydrogel has a gelation time of less than 30 seconds. In some embodiments, the first component 1 is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component 2 is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole The hydrogel can be any of the hydrogels described herein and can have any of the characteristics as indicated herein. For example, in some embodiments, the formed hydrogel can be at least 90 percent water.

The first container 1301 and the second container 1302 are configured to be coupled to the connector 1400. By having the containers as separate articles from the connector, the first container 1301 and the second container 1302 can be commercially available containers (e.g., syringes) within which the first component 1 and the second component 2, respectively, can be prepared for use. Moreover, this arrangement allows the first component 1 to be prepared within the first container 1301 (e.g., via mixing, dilution, etc.) separately from when the second component 2 is prepared within the second container 1302. In other embodiments, however, the container assembly 1300 can include a first container and a second container that are integrally and/or monolithically constructed with the connector. In yet other embodiments, the container assembly 1300 can include a single container that contains both the first component 1 and the second component 2.

As shown, the connector 1400 includes a first (or input) end portion 1401 and a second (or output) end portion 1402. The first end portion 1401 is configured to receive a tip (or connector) 1313 of the first container 1301 and a tip (or connector) 1333 of the second container 1302. The second end portion 1402 is configured to be coupled to a delivery member 1500 (see e.g., FIGS. 5 and 6). In this manner, the first component 1 can be conveyed from the first container 1301, into the first end portion 1401 of the connector 1400, and out of the second end portion 1402 of the connector to the delivery member 1500. Similarly, the second component 2 can be conveyed from the second container 1302, into the first end portion 1401 of the connector 1400, and out of the second end portion 1402 of the connector 1400 to the delivery member 1500. In some embodiments, the connector 1400 can be a mixing connector within which the first component 1 is mixed with the second component 2 before the two components are conveyed into the delivery member 1500. In other embodiments, however, the connector 1400 can maintain the first component 1 separate from the second component 2, and the two components are conveyed into and mixed within the delivery member 1500. By maintaining separate flow paths within the connector 1400, the reaction (e.g., crosslinking) between the first component 1 and the second component 2 can be performed outside of the connector 1400 (i.e., within the delivery member 1500), thereby limiting the likelihood of clogging with the connector 1400. In this manner, the connector 1400 can be used for multiple injections.

The delivery member 1500 can be any suitable delivery member, such as a needle, a catheter, or any other device through which the first component 1, the second component 2, and/or the biomaterial product 3 can be delivered to the target location. In some embodiments, the connector 1400 and the delivery member 1500 can be monolithically constructed or otherwise pre-assembled prior to use. In other embodiments, the connector 1400 can be separate from the delivery member 1500 and coupled to the delivery member 1500 as a part of the delivery procedure.

In use, after the container assembly 1300 is prepared and coupled to the delivery device 1100, the drive assembly 1150 can be actuated to produce the drive force. In this manner, the drive assembly 1150 (and the drive member 1160) can move the first plunger 1320 and the second plunger 1340 simultaneously for a time period to dispense a portion of the first component 1 from the first container 1301 and a portion of the second component 2 from the second container 1302. The first component 1 and the second component 2 are conveyed through the connector 1400, as shown by the arrow AA in FIG. 2. As described above, the first component 1 and the second component 2 can react (e.g., within the delivery member 1500, not shown in FIG. 2) to form the biomaterial product 3. The drive assembly 1150 is configured to move the first plunger 1320 and the second plunger 1340 such that the first component 1 and the second component 2 exit the connector 1400 at an exit velocity within a predetermined velocity range during the time period.

In some embodiments, the predetermined velocity range is bounded by an upper velocity threshold and a lower velocity threshold. For example, FIG. 3 shows a plot of the exit velocity as a function of time. As shown, during the injection time period Δt, the velocity of the components exiting the connector 1400 (and/or exiting the delivery member 1500) is bounded by the upper velocity threshold Vupper and the lower velocity threshold Vlower. By maintaining the velocity below the upper velocity threshold, the biomaterial can be delivered in a manner that limits the likelihood of tissue damage (e.g., due to excessive velocity causing potential tissue damage). Moreover, maintaining the velocity below the upper velocity threshold can ensure that the delivered biomaterial product 3 is properly formed within the system 1000 (e.g., the delivery member 1500) before exiting the delivery member 1500. For example, if the biomaterial product 3 has a gelation time of approximately 15 seconds, then the desired residence time of the first component 1 and the second component 2 within the delivery member is at least 15 seconds. Accordingly, the upper velocity threshold can be predetermined based on the length of the delivery member 1500 and the gelation time of the biomaterial product 3. The predetermined velocity range can be any suitable range to accommodate the desired delivery characteristics. For example, in some embodiments, the velocity range can be between 0.1 mm/sec to 10 mm/sec. In other embodiments, the velocity range can be between 0.1 mm/sec to 5 mm/sec. In other embodiments, the velocity range can be between 0.01 mm/sec and 1 mm/sec.

Moreover, by maintaining the velocity within the predetermined range and for the predetermined delivery time, the system 1000 can deliver a volume of the biomaterial product 3 that is within a desired volume range. In this manner, the amount of biomaterial can be accurately controlled. In some embodiments, the volume range is between about 5 microliters and about 1000 microliters. In other embodiments, the volume range is between about 50 microliters and 500 microliters. In yet other embodiments, the volume range is between about 50 microliters and 250 microliters. In still other embodiments, the volume range is between about 75 microliters and 150 microliters.

Additionally, in some embodiments, the lower velocity threshold is above zero. By maintaining the exit velocity (and/or the velocity within the delivery member 1500) above zero, the likelihood of clogging within the delivery member is reduced.

Although FIG. 3 depicts a quasi-constant velocity during the delivery time, in other embodiments, the drive assembly 1150 is configured to produce any desired velocity profile during the delivery time period. Similarly, in some embodiments, the drive assembly 1150 is configured to produce any desired acceleration (the rate of change of the velocity) or jerk (the rate of change of the acceleration) profile during the delivery time period. For example, FIG. 4 shows another plot of the exit velocity as a function of time. As described above, during the injection time period Δt, the velocity of the components exiting the connector 1400 (and/or exiting the delivery member 1500) is bounded by the upper velocity threshold Vupper and the lower velocity threshold Vlower. Additionally, the drive assembly 1150 produces a velocity profile having an initial "high velocity" portion, followed by a deceleration to a lower velocity portion. In addition to providing control of the delivery velocity (and/or acceleration), in some embodiments, the drive assembly 1150 can be configured to maintain the drive force applied by the drive member 1160 on the plungers below a force threshold.

The system 1000 (and any of the systems described herein) can be used to deliver a biomaterial product (such as any of the hydrogels described herein) to a target location. For example, FIGS. 5-7 are schematic illustrations showing the system 1000 being used to deliver a biomaterial product 3 to a body lumen L. In use, the container assembly 1300 can be readied for use by preparing (e.g., mixing, reconstituting, etc.) and loading the first component 1 into the first container 1301 and the second component 2 into the second container 1302. The container assembly 1300 can then be coupled to (or loaded into) the delivery device 1100 and primed for use, in accordance with any of the methods described herein. The delivery member 1500 is then inserted into the body lumen L, as shown in FIG. 5. In some embodiments, the delivery member 1500 can be inserted before being connected to the connector 1400. In other embodiments, however, the delivery member 1500 can be coupled to the connector 1400 and then inserted into the body lumen L. As shown in FIG. 6, the delivery device 1100 can be actuated to initiate delivery of the first component 1 and the second component 2 through the connector 1400 and the delivery member 1500, as described above. Specifically, the delivery device 1100 can convey the first component 1 and the second component 2 for a delivery time period and within a desired velocity range. In this manner, the desired volume or length of the biomaterial product 3 can be delivered into the body lumen L. The delivery member 1500 can then be removed from the body lumen L, as shown in FIG. 7. The body lumen L can be any suitable body lumen, such as, for example, an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate. The target location can also be an organ of a gastrointestinal tract or circulatory system or respiratory system or nervous system, a subcutaneous space, an intramuscular space, or an interstitial space.

Figure 8:
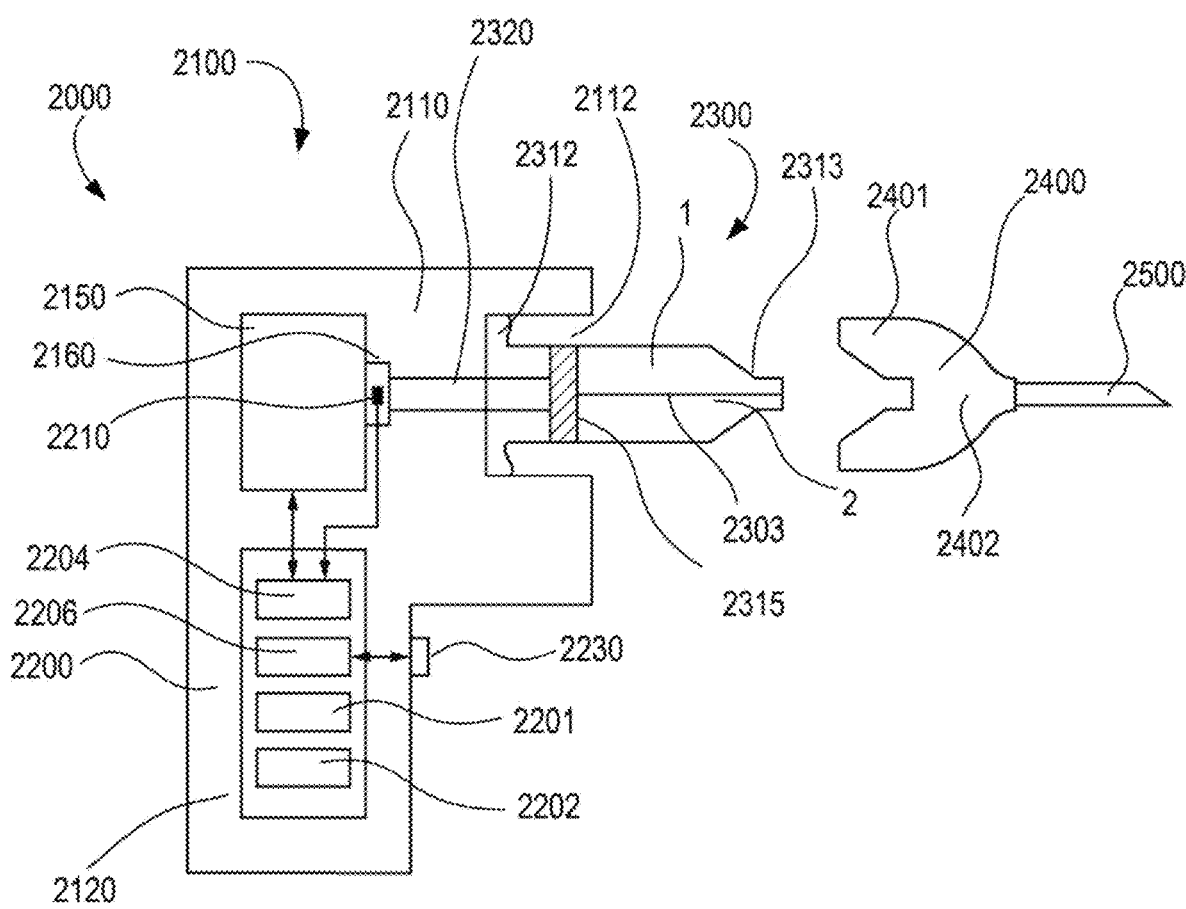
FIG. 8 is schematic illustration of a delivery system including a body, a connector, a drive assembly, and an electronic control system according to an embodiment.
Figure 9:
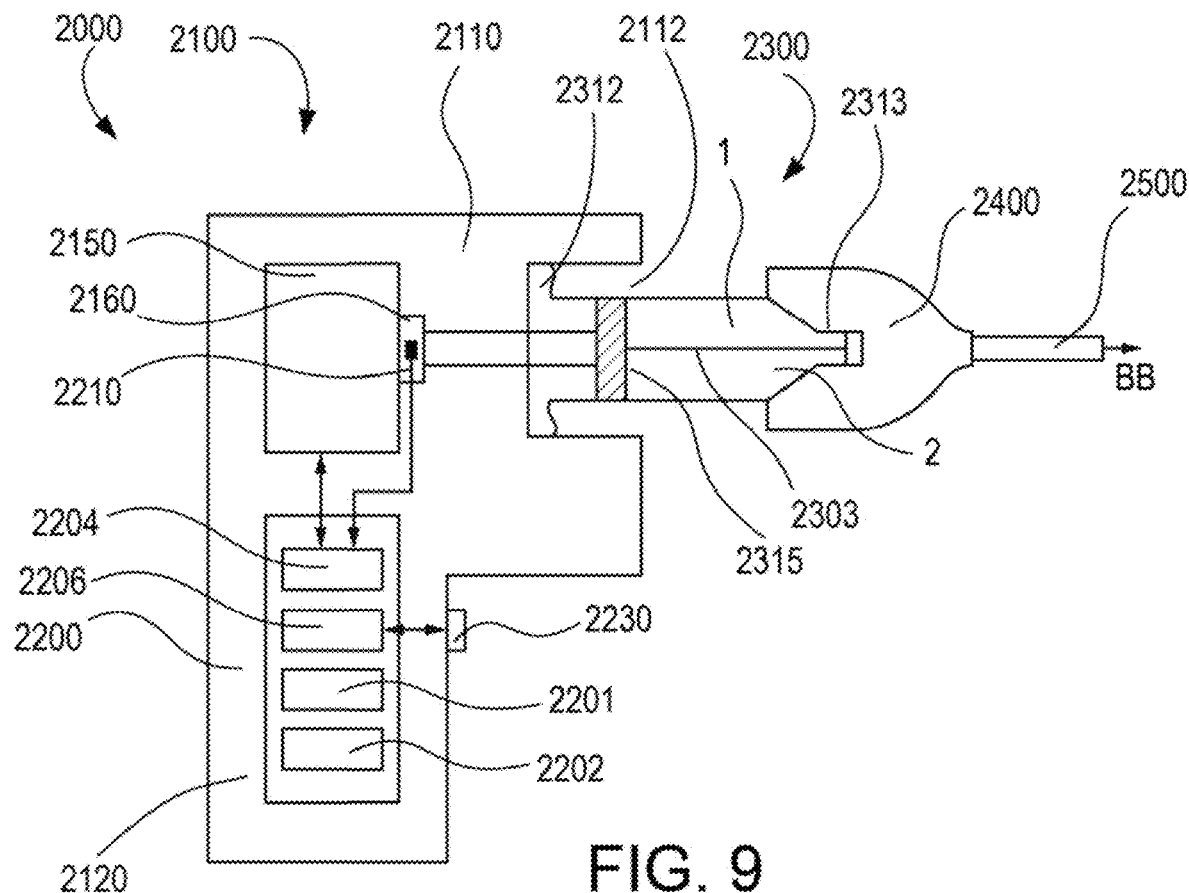
FIG. 9 is schematic illustration of the delivery system in FIG. 8 with the connector coupled to the body.
Figure 10:
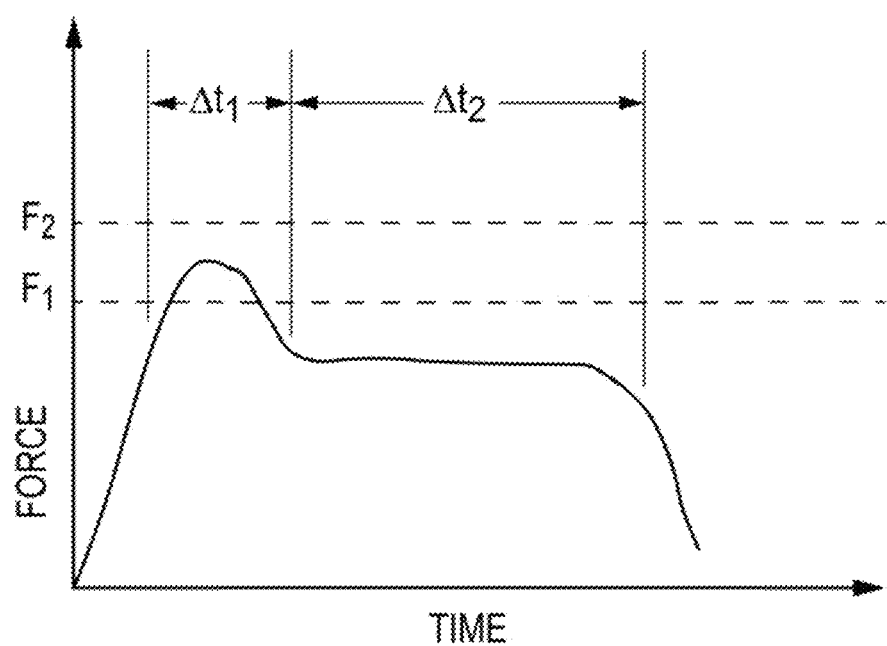
FIG. 10 is a plot showing a sample force profile of the biomaterial components during use of the delivery system of FIG. 9.

In some embodiments a delivery device can include one or more feedback sensors to facilitate closed-loop control of the delivery characteristics of the biomaterial product. Such delivery characteristics can include the velocity of the components delivered from the container assembly, the velocity of the biomaterial product delivered, the peak force applied during delivery, the amount of biomaterial product delivered, a sudden drop-off or spike in forces observed at the plunger, or the like. For example, FIGS. 8 and 9 are schematic illustrations of a system 2000 (also referred to as a delivery system) according to an embodiment. As described herein, the system 2000 is configured to convey and combine multiple biomaterial components that form a biomaterial product that is delivered to a target location. FIG. 10 is a plot showing a sample force profile of the biomaterial components during use of the system 2000. The system 2000 includes a delivery device 2100, a container assembly 2300, a connector 2400, and a delivery member 2500.

The delivery device 2100 includes a housing 2110, a drive assembly 2150, and an electronic control system 2200. The housing 2110 includes a container receiving portion 2112 configured to receive at least a portion of the container assembly 2300. The container receiving portion 2112 can be an opening or recess within which an end portion 2312 of the container assembly 2300 can be retained during use. The container receiving portion 2112 can include any suitable retention structure, locking members, pin system, magnets, or the like. The housing 2110 can also contain the drive assembly 2150 and the electronic control system 2200. As shown, the housing 2110 includes a handle 2120 that can be gripped and/or manipulated by a user during operation of the device 2100. The housing 2110 can be made from any suitable material or materials and can provide any suitable structural components to receive and/or retain the portion of the container assembly 2300 and perform any of the functions described herein. For example, in some embodiments, the housing 2110 can be constructed from multiple components that are joined together (e.g., via a hinged joint, a mechanical fastener or the like) to surround and/or secure the container assembly 2300.

The container assembly 2300 has a first end portion 2311, a second end portion 2312, and includes an elastomeric member (or stopper) 2315 therein. The container assembly 2300 defines a first chamber (or volume) and a second chamber (or volume) that is separated from the first chamber by a separation member 2303. The first chamber contains a first component 1 and the second chamber contains a second component 2 that is separate from the first component (i.e., by the separation member 2303). The separation member 2303 can be a flexible member, a seal, or any other structure that maintains the first chamber separate from and/or fluidically isolated from the second chamber. In this manner, the first component 1 and the second component 2 can be stored within the container assembly 2300 without reacting together. The first chamber and the second chamber are bounded on one side by the elastomeric member 2315. The container assembly 2300 includes a plunger 2320 having an end portion movably disposed within the container assembly 2300 such that movement of the plunger 2320 will cause movement of the elastomeric member 2315 to convey the first component 1 and the second component 2 from the container assembly 2300. The opposite end of the first plunger 2320 is operably coupled to (e.g., is configured to engage) a drive member 2160 of the drive assembly 2150.

The first component 1 and the second component 2 can be any of the biomaterial components described herein. For example, in some embodiments, the first component 1 and the second component 2 can each be a water soluble component (e.g., monomer, macromer, polymer, or the like) that is capable of crosslinking (e.g., with the other component) to form a hydrogel (as the delivered biomaterial product). In some embodiments, the first component 1 and the second component 2 are formulated such that the resulting hydrogel has a gelation time of less than 5 minutes. In other embodiments, the first component 1 and the second component 2 are formulated such that the resulting hydrogel has a gelation time of less than 2 minutes. In other embodiments, the first component 1 and the second component 2 are formulated such that the resulting hydrogel has a gelation time of less than 2 minute. In yet other embodiments, the first component 1 and the second component 2 are formulated such that the resulting hydrogel has a gelation time of less than 30 seconds. In some embodiments, the first component 1 is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component 2 is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole. The hydrogel can be any of the hydrogels described herein and can have any of the characteristics as indicated herein. For example, in some embodiments, the formed hydrogel can be at least 90 percent water. In other embodiments, the formed hydrogel can be >50% water.

The container assembly 2300 is configured to be coupled to the connector 2400 and a delivery member 2500. By having the containers as separate articles from the connector and delivery member, the first component 1 and the second component can each be prepared within the container assembly 2300 (e.g., via mixing, dilution, etc.) separately from when connector 2400 is attached. In other embodiments, however, the container assembly 2300 can be provided as a prefilled assembly. In other embodiments, the container assembly 2300 can be integral to and/or monolithically constructed with the connector 2400. In yet other embodiments, the container assembly 2300 can include two separate containers, like the first container 1301 and the second container 1302 described herein.

The connector 2400 can be similar to any of the connectors described herein, and includes a first (or input) end portion 2401 and a second (or output) end portion 2402. The first end portion 2401 is configured to receive a tip (or connector) 2313 of the container assembly 2300. The second end portion 2402 is configured to be coupled to a delivery member 2500. In this manner, the first component 1 and the second component 2 can be conveyed from the container assembly 2300, into the first end portion 2401 of the connector 2400, and out of the second end portion 2402 of the connector to the delivery member 2500. In some embodiments, the connector 2400 can be a mixing connector within which the first component 1 is mixed with the second component 2 before the two components are conveyed into the delivery member 2500. In other embodiments, however, the connector 2400 can maintain the first component 1 separate from the second component 2, and the two components are conveyed into and mixed within the delivery member 2500. By maintaining separate flow paths within the connector 2400, the reaction (e.g., crosslinking) between the first component 1 and the second component 2 can be performed outside of the connector 2400 (i.e., within the delivery member 2500), thereby limiting the likelihood of clogging with the connector 2400. In this manner, the connector 2400 can be used for multiple injections.

The delivery member 2500 can be any suitable delivery member, such as a needle, a catheter, or any other device through which the first component 1, the second component 2, and/or the delivered biomaterial product can be delivered to the target location. In some embodiments, the connector 2400 and the delivery member 2500 can be monolithically constructed or otherwise pre-assembled prior to use. In other embodiments, the connector 2400 can be separate from the delivery member 2500 and coupled to the delivery member 2500 as a part of the delivery procedure.

The drive assembly 2150 can be any suitable assembly or mechanism that produces a drive force to convey the first biomaterial component 1, or the second biomaterial component 2, or both the first component 1 and the second component 2 from the container assembly 2300 as described herein. More specifically, the drive assembly 2150 can produce the drive force and/or convey the components within a desired velocity range, force range, and/or range of flow rates. As shown, the drive assembly 2150 includes a drive member 2160 that is operably coupled to the container assembly 2300 such that, upon actuation, the drive assembly 2150 can convey the first component 1 and the second component 2 from the container assembly 2300. The drive assembly 2150 can include any suitable mechanism for producing the drive force. For example, in some embodiments, the drive assembly can include an electromechanical driver (not shown in FIGS. 8 and 9) to produce the drive force. Such electromechanical drivers can include, for example, a motor-driven linear actuator, a hydraulic actuator (e.g., that includes a pump driven by an electronic component), a magnetic-based actuator, a pneumatic actuator that includes an electromechanical valve to control a pressure applied to the drive member 2160, or any other suitable electromechanical driver of the types described herein. In some embodiments the drive assembly 2150 (or any of the drive assemblies described herein) can include one or more springs configured to apply force onto the drive member. Furthermore, these preloaded drive assembles can facilitate multiple injections with the same device.

The electronic control system 2200 controls the electromechanical driver and any other suitable aspect of the drive assembly to control the delivery characteristics of the first component 1, the second component 2, and/or the delivered product, as described herein. As shown, the electronic control system 2200 includes one or more sensors 2210, one or more processors 2201, one or more memory components 2202, and various modules, such as a drive module 2204 and a user interface module 2206. Although FIGS. 8 and 9 illustrates the electronic control system 2200 being within the housing 2110, the electronic control system 2200 or portions thereof can be provided outside of the housing 2110 (e.g., certain operations of the electronic control system 2200 can be performed within a cloud computing environment). As described herein, the electronic control system 2200 can automatically control the duration of delivery, the velocity of the components, the peak force applied during delivery, and any other aspects of delivering the biomaterial product.

Specifically, the electronic control system 2200 can control the drive assembly 2150 based on feedback from the sensor(s) 2210. The sensor 2210 can be separate and/or included within the electronic control system 2200 can include any suitable sensor that produces a feedback signal associated with at least one of a position of the drive member 2160, a velocity of the drive member 2160, an acceleration of the drive member 2160, or the drive force applied by the drive member 2160. Such sensors can include, for example, imaging devices, optical sensors, accelerometers, temperature sensors, contact sensors, proximity sensors, position sensors, and/or any other suitable input device. For example, in some embodiments, the sensor 2210 can be a linear position sensor (e.g., an LVDT or the like) that produces a feedback signal associated with the position of the drive member 2160. The feedback signal can also be used to determine changes in position during the delivery event (i.e., the velocity of the drive member 2160). In other embodiments, the sensor 2210 can be a force sensor (e.g., a strain gauge force sensor) that produces a feedback signal associated with the force applied by or exerted on the drive member 2160. In yet other embodiments, the sensor 2210 can be a current sensor that measures the current and/or voltage supplied to the electromechanical driver. From the measured current and/or voltage, the electronic control system 2200 (e.g., the drive module 2202) can calculate the power, and therefore, the approximate force applied by the drive member 2160. The sensor 2210 can also be other type of sensor, such as an accelerometer (to measure vibration, motion and/or acceleration of the drive member 2160), an optical sensor(s) to detect certain positions of the drive member 2160 and/or container assembly 2300, or one or more switches. Although described as including one feedback sensor, the electronic control system 2200 (and any of the electronic control systems described herein) can include any number of sensors. For example, in some embodiments, the electronic control system 2200 can include a linear position sensor to measure the position of the drive member 2160 and an optical sensor to determine whether the connector 2400 is coupled to the container assembly 2300. In some embodiments, the electronic control system 2200 is configured to detect and verify that the container assembly 2300 and/or the connector assembly 2400 are properly mounted and coupled to the housing 2110. In some embodiments, the electronic control system 2200 is configured to monitor a position the plunger 2320 relative to the drive member 2160 and/or the housing 2110 to improve accuracy and control of the plunger 2320 during priming operation or the injection operation.

The processor 2201, and any of the processors described herein can be any suitable processor for performing the methods described herein. In some embodiments, processor 2201 can be configured to run and/or execute application modules, processes and/or functions associated with the delivery device 2100. For example, the processor 2201 can be configured to run and/or execute the drive module 2204, the user interface module 2206 (which functions an input/output module), and/or any of the other modules described herein, and perform the methods associated therewith. The processor 2201 can be, for example, a Field Programmable Gate Array (FPGA), an Application Specific Integrated Circuit (ASIC), a Digital Signal Processor (DSP), and/or the like. The processor 2201 can be configured to retrieve data from and/or write data to memory, e.g., the memory 2202.

The memory 2202 (or any of the memory devices described herein) can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 2202 stores instructions to cause the processor 2201 to execute modules, processes and/or functions associated with the delivery device 2100. For example, the memory 2202 can store instructions to cause the processor 2201 to execute any of the application modules described herein, and perform the methods associated therewith.

The user interface module 2206 can be a hardware and/or software module (stored in memory 2202 and/or executed in the processor 2201). The user interface module 2206 can be configured to receive input from and/or produce output to the user. For example, the user can depress the actuator button 2230, which is operatively coupled to the electronic control system 2200. The user interface module 2206 can receive the input and produce one or more signals based on the user input. For example, in some embodiments, the user interface module 2206 can produce a signal to the drive assembly 2150 to "prime" the system by moving the drive member 2160 a predetermined distance. In other embodiments, the user interface module 2206 can produce a signal to the drive assembly 2150 to stop movement of the drive member 2160 (e.g., in an error state or "stop" state). The user interface module 2206 can also produce a signal to cause the electronic control system 2200 to produce one or more outputs. For example, in some embodiments, the electronic control system 2200 (and any of the electronic control systems described herein) includes an output device, such a light output device (e.g., LED's), an audible output device (e.g., speaker), or a tactile output device (e.g., vibration device). In such embodiments, the user interface module 2206 can produce a signal to cause the output device to produce an output (e.g., a visual, audible, or tactile output) to indicate a change in state (e.g., priming completed, mixing completed, injection complete) or error condition associated with the delivery device 2100. In some embodiments, the user interface module 2206 includes a graphical user interface to display information relating to the system 2000 and to receive inputs from a user.

The drive module 2204 can be a hardware and/or software module (stored in memory 2202 and/or executed in the processor 2201). The drive module 2204 can be configured to receive the feedback sensor (e.g., from the sensor(s) 2210) and produce, based on the feedback signal, a drive signal to maintain the drive force below a drive force threshold. For example, after the container assembly 2300 is prepared and coupled to the delivery device 2100, the drive assembly 2150 can be actuated (e.g., via the actuator button 2230) to produce the drive force. In this manner, the drive assembly 2150 (and the drive member 2160) can move the plunger 2320 for a time period to dispense a portion of the first component 1 and a portion of the second component 2 from the container assembly 2300. The first component 1 and the second component 2 are conveyed through the connector 2400 and into the delivery member 2500. The first component 1 and the second component 2 can react (e.g., within the delivery member 2500) to form the biomaterial product, as shown by the arrow BB. The drive module 2204 is configured produce a drive signal to maintain the drive force below a drive force threshold during the delivery time period. The drive signal can be, for example, a control signal that adjusts a level of power (e.g., current or power) applied to the drive assembly 2150 to maintain the drive force below the drive force threshold. In some embodiments, the drive assembly 2150 can include an electromechanical driver, such as a stepper motor. The drive signal can be a series of pulses to maintain and/or control the speed of the motor, thereby maintaining the force below the drive force threshold.

In some embodiments, the drive module 2204 can be configured to maintain the drive force below more than one threshold. For example, FIG. 10 shows a plot of the drive force as a function of time. In some embodiments, the injection can be divided into two time periods: a first time period $\Delta t_1$ and a second time period $\Delta t_2$. During the first time period, which can be referred to as a "breakaway" period, the drive module 2204 can be configured to maintain the drive force below a breakaway force threshold (identified as $F_2$ in FIG. 10). During the second time period, which can be referred to as a "delivery" period, the drive module 2204 can be configured to maintain the drive force below a drive force threshold (identified as $F_1$ in FIG. 10). As shown, the drive force threshold is lower than the breakaway force threshold. By controlling drive assembly 2150 to produce a higher force on the "startup" period (i.e., the period during which movement of the plunger 2320 is initiated), the system can overcome static friction, while still minimizing the high force impulse to limit potential tissue damage. Although FIG. 10 shows the drive force threshold being lower than the breakaway force threshold, in other embodiments, the drive force threshold can be equal to or higher than the breakaway force threshold. In yet other embodiments, the drive force can be maintained below more than two different thresholds. For example, in some embodiments, the drive module 2204 can be configured to maintain the drive force below a drive threshold force curve that changes as a function of time. In some embodiments, the drive threshold curve can remain constant, increase, and/or decrease as a function of time.

In some embodiments, the drive module 2204 and/or the user interface module 2206 is configured to produce an error signal when the drive force exceeds the drive force threshold. In some embodiments, the error signal can cause an output device (not shown) to produce any one of a visual, audible, or tactile output. In other embodiments, the error signal can cause a reduction in the power or drive signal to the drive assembly 2150. Similarly stated, the error signal can cause the drive assembly 2150 to reduce and/or stop movement to limit the likelihood of tissue damage caused by excessive force. In yet other embodiments, the drive module 2204 can produce a completion signal at the end of the delivery event to cause the drive assembly 2150 to stop movement.

By maintaining the drive force below the drive force threshold, the biomaterial can be delivered in a manner that limits the likelihood of tissue damage (e.g., due to excessive velocity and/or force causing potential tissue damage). Specifically, the drive force (i.e., the force applied by the delivery member) is related to the force with which the biomaterial is delivered to the target location (i.e., the delivery force). For example, the drive force generates a pressure within the container assembly that moves the elastomeric member thereby causing the flow of the first component 1 and the second component 2 through the system (including the connector 2400 and the delivery member 2500). The drive force is counteracted by friction forces within the system as wells as pressure from the delivery site. Thus, the delivery force, which is applied to and/or within the target tissue, is associated with the drive force and also the losses (e.g., friction forces) through the system. The drive force threshold can be any suitable value. For example, in some embodiments, the drive force can be maintained between 0.1N and about 45N. In other embodiments, the drive force can be maintained below about 20N. In yet other embodiments, the drive force can be maintained below about 12N and/or within a range of between about 7N and 12N.

In some embodiments, the drive module 2204 can be configured to maintain a velocity of the components exiting the connector 2400 (and/or exiting the delivery member 2500) within a desired velocity range, similar to the ranges described above with respect to the delivery device 1100. As described above, the drive force needed to deliver the components from the container assembly 2300 and the biomaterial product exiting the delivery member 2500 is related to the target flow rate (and therefore the velocity), the properties of the materials (e.g., viscosity), and the characteristics of the delivery system 2000 (e.g., length of the delivery member and friction between the elastomeric member 2315 and the container assembly 2300). In certain circumstances (i.e., laminar flow of the components), the pressure of the first component 1 and the second component 2 within the container assembly 2300 (which is related to the drive force exerted by the drive assembly 2150) can be modeled by the Hagen-Poiseuille law, as indicated below:

$$P = (8 * \mu * L * Q)/(\Pi * R^4) \quad (1)$$

where P is the pressure of the first component 1 and/or the second component 2 within the container assembly 2300, $\mu$ is the viscosity of the first component 1 and/or the second component 2, L is the length of the delivery member 2500, Q is the flow rate of the first component 1, the second component 2, and/or the biomaterial product through the delivery member 2500, and R is the radius of the lumen defined by the delivery member 2500. Because the pressure (and therefore drive force) required to inject a high viscosity fluid through a small-diameter delivery member is proportional to the inverse of the radius of the lumen of the delivery member to the fourth power, the pressure of the components within the container assembly 2300 must be high enough to achieve the desired flow rate, while being controlled to avoid excess flow rates (or velocities) and/or high delivery (or exit) forces, which could damage the target tissue. Furthermore, for certain applications, it is necessary to control the injection location, rate of delivery, and volume of the biomaterial delivered such that implantation of the biomaterial into that tissue space does cause the material to enter or damage other tissue spaces. For example, if the injection is too slow based upon the mechanical properties and pressures at the implantation site this can cause a poorly formed implant or leakage from entry site for implantation or clogs. For example, if the injection is too fast based upon the mechanical properties and pressures at the implantation site this can cause excessive tissue damage or vessel rupture or foreign body response from damage of implantation.

In some embodiments, the container assembly 2300 (and any of the container assemblies described herein), the first component 1 and the second component 2 can be configured and/or formulated to facilitate maintaining a desired force and/or velocity profile. For example, in some embodiments, the container assembly 2300 (and any of the container assemblies described herein) can include two containers of equal size and containing substantially the same volume of the components. Moreover, in some embodiments, any of the devices and methods described herein can include conveying equal amounts of the first component 1 and the second component 2 to produce the biomaterial product. Further, in some embodiments, the viscosity of the first component 1 and the second component 2 can be "matched." Specifically, in some embodiments, the first component is characterized by a first viscosity and the second component is characterized by a second viscosity, the second viscosity being within twenty-five percent of the first viscosity.

Figure 11:
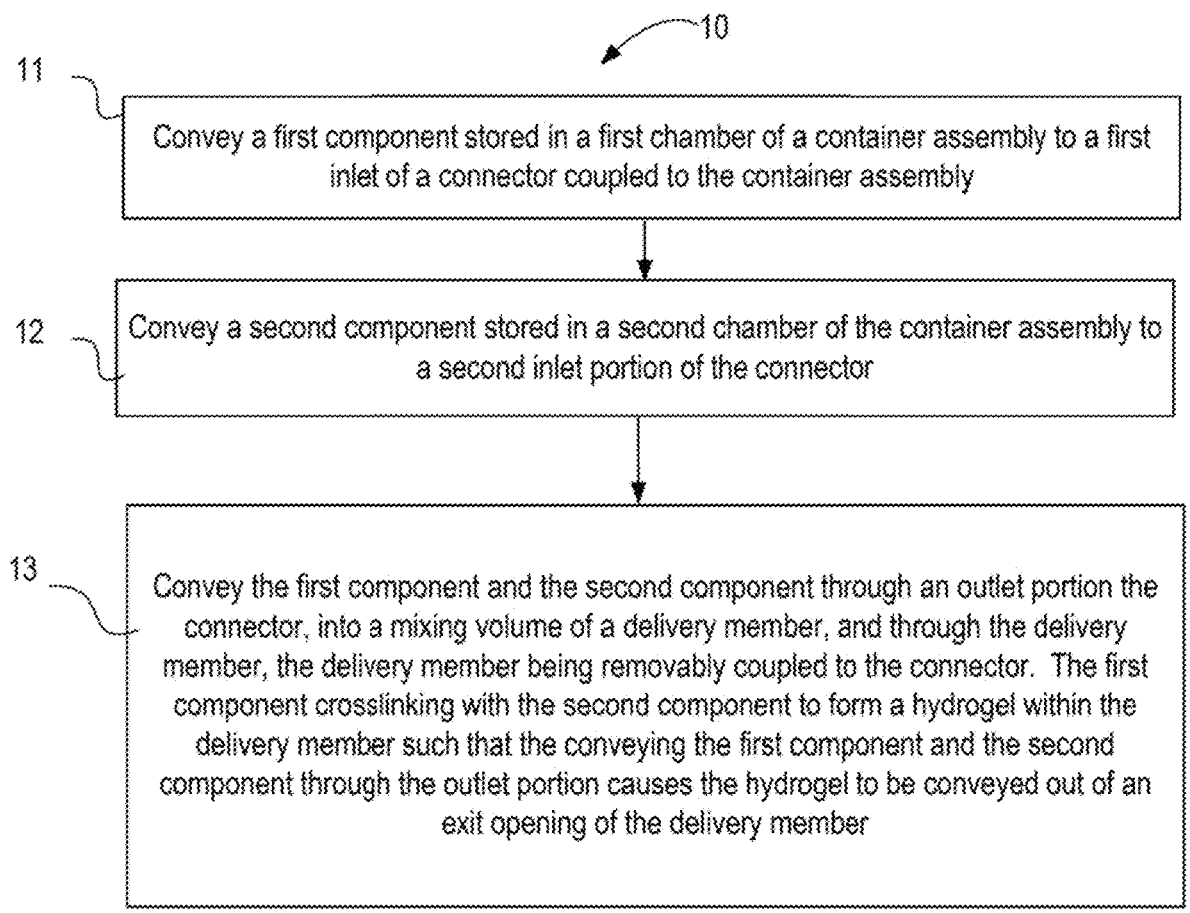
FIG. 11 is a flow chart of a method of conveying first and second components from a container assembly to form a hydrogel according to an embodiment.

FIG. 11 is a flow chart illustrating a method 10 of delivering a biomaterial product, according to an embodiment. The method 10 can be performed with any of the systems, delivery devices, and components described herein, such as, for example, the delivery systems 1000, 2000, 3000, and 4000 and/or the delivery devices 1100, 2100, 3100, and 4100 described herein. The method includes conveying a first component stored in a first chamber of a container assembly to a first inlet of a connector coupled to the container assembly, at 11. The method further includes conveying a second component stored in a second chamber of the container assembly to a second inlet portion of the connector, at 12. In some embodiments, the container assembly includes two separate containers, with the first component being within the first container and the second component being within the second container. In other embodiments, however, container assembly includes a single container (similar to the container assembly 2300 described above), with the first component and the second component being within separate chambers of the container. In some embodiments, the first component and the second component can be conveyed to the connector simultaneously.

The first component and the second component are then conveyed through an outlet portion of the connector, into a mixing volume of a delivery member, and through the delivery member, at 12. The delivery member is removably coupled to the connector. The first component crosslinks with the second component to form a hydrogel within the delivery member such that the conveying the first component and the second component through the outlet portion causes the hydrogel to be conveyed out of an exit opening of the delivery member. Similarly stated, the first component and the second component are delivered in a manner to ensure that the hydrogel (also referred to as the delivered product) is fully formed within the system (e.g., the delivery member 1500), thereby ensuring that that the first component and the second component are not delivered while the delivered product is still yet to be formed (or is only partially formed).

The first component and the second component can be any of the components or compositions described herein. For example, in some embodiments, the first component and the second component are formulated such that the hydrogel has a gelation time. The first component and the second component are conveyed through the outlet portion, into the mixing volume, and through the delivery member within a flow rate range that is based on the gelation time such that they hydrogel is fully formed within the delivery member before being conveyed out of the exit opening.

In some embodiments, the hydrogel is conveyed out of the exit opening of the delivery member into a body lumen to at least partially occlude the body lumen. The body lumen can be any suitable body lumen, such as for example, an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space.

In some embodiments, the method 10 optionally includes removing the connector from the delivery member. The method can further optionally include coupling a second delivery member to the connector and conveying a second amount of the first component and the second component through the outlet portion of the connector, into a mixing volume of the second delivery member, and through the second delivery member to a second target location within the body.

In some embodiments, any of the delivery devices described herein can be configured to prime the biomaterial product and/or perform the injection. "Priming" is defined as any steps that prepare the material prior to injection, for example, mixing or merging solutions within the device, removing dead volume (e.g., from the connector), and/or setting/adjusting the injection volume. "Injection" is defined as delivering the biomaterial product into the body. In one aspect, the priming and injection steps are pre-defined and not adjustable by the user (e.g. physician). In one aspect, both the priming and injection steps are adjustable by the user. In one aspect, the priming and injection steps can be a combination of adjustable and not adjustable.

In some embodiments, any of the device described herein may be able to perform one or more injections, such as delivering two biomaterial products into the same patient from the same apparatus. In some embodiments, any of the device described herein can perform a single priming step and single injection; single priming step and multiple injections; multiple priming steps and a single injection; and multiple priming steps and multiple injections. The priming and injection steps can be performed in a pre-defined sequence or performed in any order. The priming steps may be the same or different volumes. If multiple injections are done, they may be the same or different volumes each time.

In some embodiments, the priming and/or injection(s) may occur via user input; for example, the user's hands or fingers may apply force on levers, switches, plungers, pistons, and/or rods. In some embodiments, the priming and/or injection(s) may occur by the apparatus or motor or actuator applying a force on levers, switches, plungers, and/or rods; often, the user may initiate these steps through a switch, trigger, button, lever, rod, graphical user interface and/or voice command. The priming and/or injection(s) may occur through a combination of user input and apparatus, such as where the user provides part of the force and part of the force is derived from the apparatus or motor or actuator, which can include or act on levers, switches, plungers, pistons, and/or rods. In other embodiments, other actuators (e.g. linear actuator) or pumps (e.g. peristaltic pump) can be used for priming and/or injection. One or more reservoirs can also be included for storing the biomaterial components individually or together in a manner suitable for providing the biomaterials ready for injection.

Figure 12:
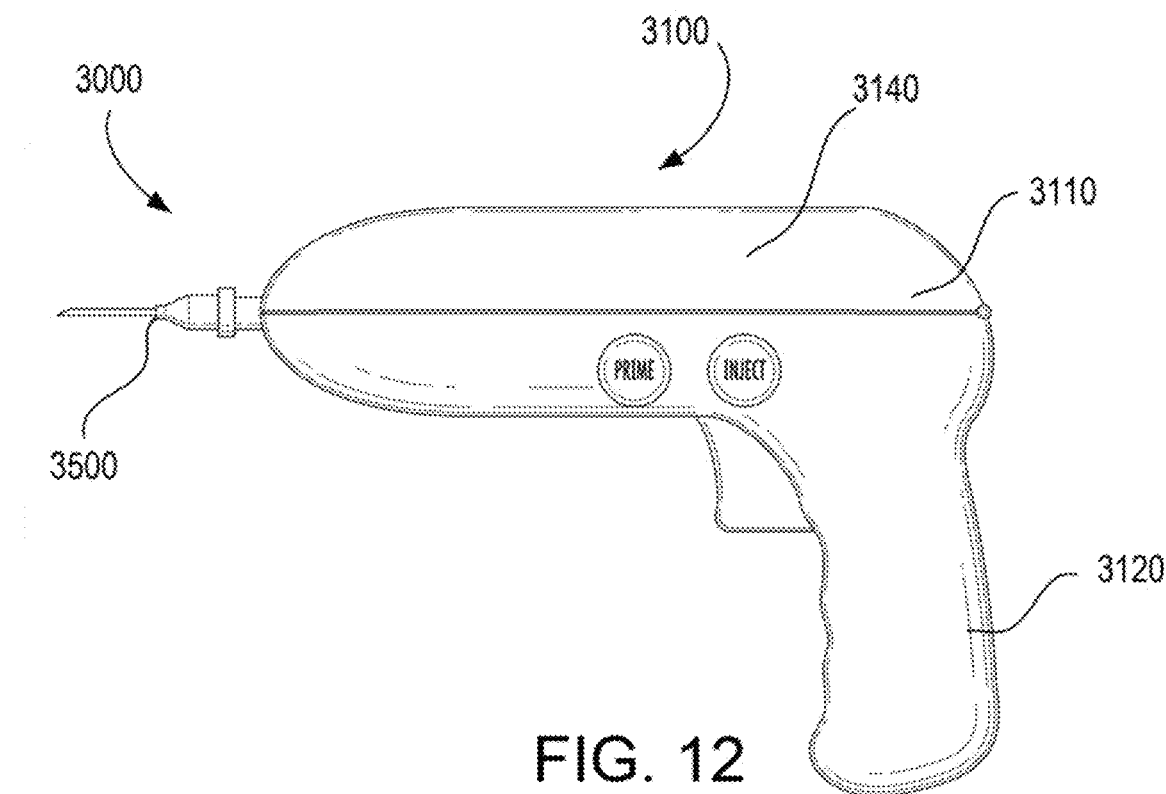
FIG. 12 is a schematic diagram showing a side view of a delivery apparatus according to an embodiment.
Figure 13:
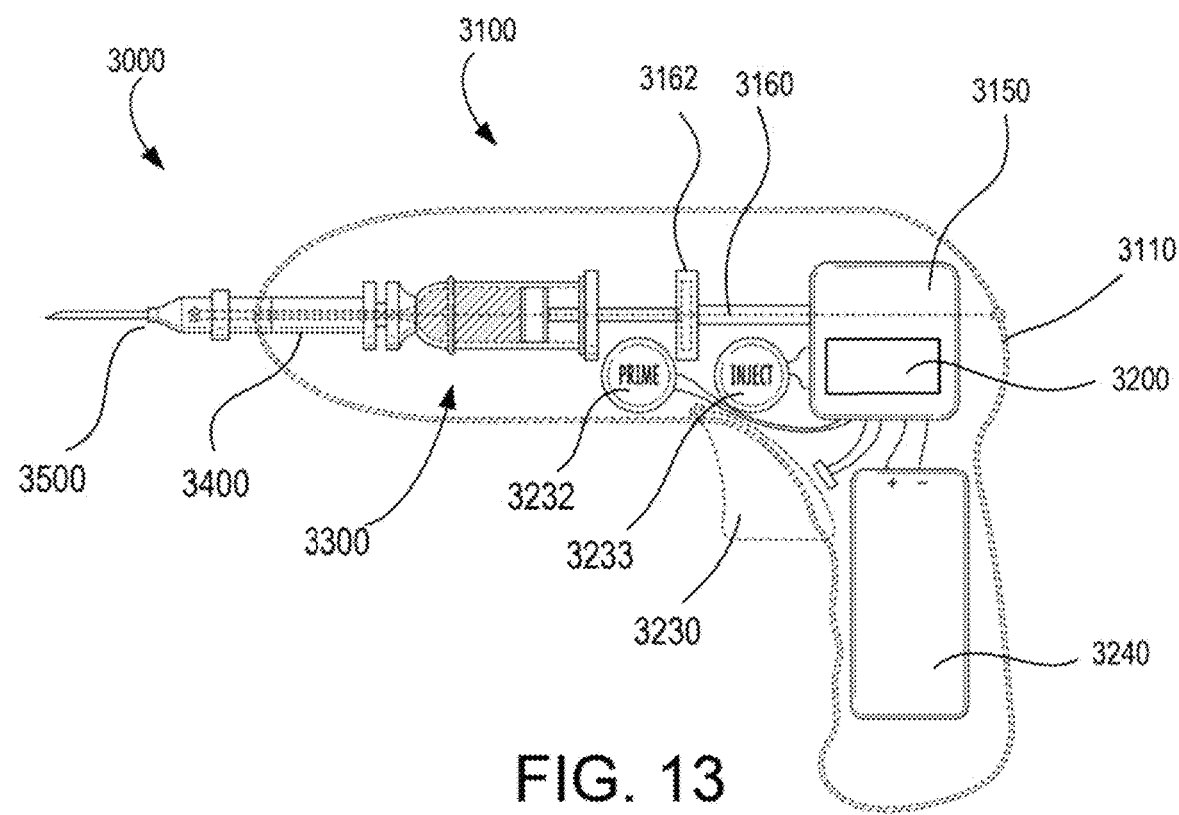
FIG. 13 is a schematic diagram showing a cross-sectional, side view of the delivery apparatus of FIG. 12.
Figure 14:
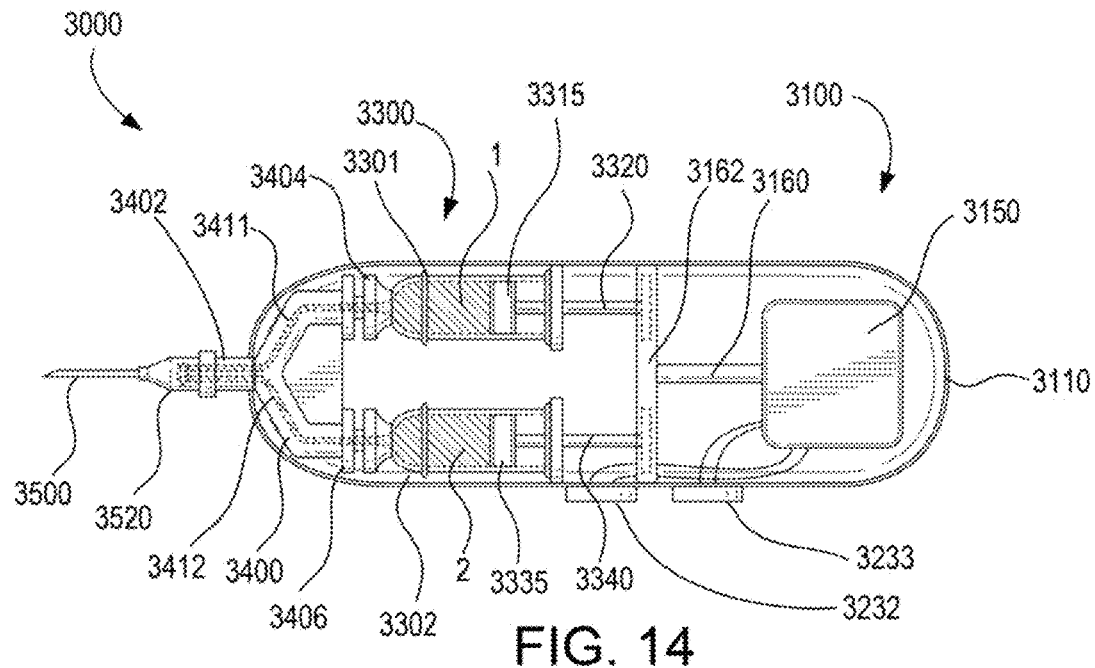
FIG. 14 is a schematic diagram showing a cross-sectional, top view of a delivery apparatus of FIG. 12.

For example, FIGS. 12-14 show various views of a system 3000 that includes a delivery device 3100 that both primes and injects a biomaterial, according to an embodiment. The system 3000 includes the delivery device 3100, a container assembly 3300, a connector 3400, and a delivery member 3500. The delivery device 3100 includes a housing 3110, a drive assembly 3150, and an electronic control system 3200. The housing 3110 is configured to receive the container assembly 3300. Specifically, the housing 3110 can include an opening or recess within which the container assembly 3300 can be retained during use. The housing 3110 can include any suitable retention structure, locking members, or the like. The housing 3110 also contains the drive assembly 3150 and the electronic control system 3200. As shown, the housing 3110 includes a handle 3120 that can be gripped and/or manipulated by a user during operation of the device. 3100. The housing 3110 can be made from any suitable material or materials and can provide any suitable structural components to receive and/or retain the portion of the container assembly 3300 and perform any of the functions described herein.

The container assembly 3300 includes a first container 3301 and a second container 3302. The first container 3301 has a first end portion, a second end portion, and includes an elastomeric member (or stopper) 3315 therein. The first container 3301 defines a volume that is bounded on one side by the elastomeric member 3315 and that contains a first component 1. The first container 3301 includes a first plunger 3320 having an end portion movably disposed within the first container 3301 such that movement of the first plunger 3320 will cause movement of the elastomeric member 3315 to convey the first component 1 from the first container 3301. The opposite end of the first plunger 3320 is operably coupled to (e.g., is configured to engage) the drive member 3160. The second container 3302 has a first end portion, a second end portion, and includes an elastomeric member (or stopper) 3335 therein. The second container 3302 defines a volume that is bounded on one side by the elastomeric member 3335 and that contains a second component 2. The second container 3302 includes a second plunger 3340 having an end portion movably disposed within the second container 3302 such that movement of the second plunger 3340 will cause movement of the elastomeric member 3335 to convey the second component 2 from the second container 3302. The opposite end of the second plunger 3340 is operably coupled to (e.g., is configured to engage) the drive member 3160. In this manner, a single drive assembly 3150 can move both the first plunger 3320 and the second plunger 3340. The first container 3301 and the second container 3302 (and any of the containers described herein) can be any suitable containers, as described herein.

The first component 1 and the second component 2 can be any of the biomaterial components described herein. For example, in some embodiments, the first component 1 and the second component 2 can each be a water soluble component (e.g., monomer, macromer, polymer, or the like) that is capable of crosslinking (e.g., with the other component) to form a hydrogel (as the delivered biomaterial product). In some embodiments, the first component 1 and the second component 2 are formulated such that the resulting hydrogel has a gelation time of less than 5 minutes. In other embodiments, the first component 1 and the second component 2 are formulated such that the resulting hydrogel has a gelation time of less than 2 minutes. In other embodiments, the first component 1 and the second component 2 are formulated such that the resulting hydrogel has a gelation time of less than 1 minute. In yet other embodiments, the first component 1 and the second component 2 are formulated such that the resulting hydrogel has a gelation time of less than 30 seconds. In some embodiments, the first component 1 is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component 2 is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole. The hydrogel can be any of the hydrogels described herein and can have any of the characteristics as indicated herein. For example, in some embodiments, the formed hydrogel can be at least 90 percent water.

The container assembly 3300 is configured to be coupled to the connector 3400, which is, in turn, coupled to a delivery member 3500. By having the containers as separate articles from the connector 3400 and delivery member 3500, the first component 1 and the second component can each be prepared within the container assembly 3300 (e.g. via mixing, dilution, etc.) separately from when connector 3400 is attached. In other embodiments, however, the container assembly 3300 can be provided as a prefilled assembly.

The connector 3400 can be similar to any of the connectors described herein, and includes a first (or input) end portion and a second (or output) end portion 3402. The first end portion includes a first inlet 3404 that is coupled to a tip (or connector) of the first container 3301 and a second inlet 3406 that is coupled to a tip (or connector) of the second container 3302. The second end portion 3402 is configured to be coupled to the delivery member 3500 (FIGS. 12-14 show the connector 3400 being coupled to a hub 3520 of the delivery member 3500). As shown in FIG. 14, the connector 3400 defines a first passageway (or lumen) 3411 placing the first inlet 3404 in fluid communication with the second end portion 3402 and a second passageway (or lumen) 3412 placing the second inlet 3406 in fluid communication with the second end portion 3402. In this manner, the first component 1 can be conveyed from the first container 3301, into the first end portion of the connector 3400, and out of the second end portion 3402 of the connector to the delivery member 3500. Similarly, the second component 2 can be conveyed from the second container 3302, into the first end portion of the connector 3400, and out of the second end portion 3402 of the connector 3400 to the delivery member 3500. As shown, the connector 3400 maintains the first component 1 separate from the second component 2, and the two components are conveyed into and mixed within the hub 3520 of the delivery member 3500. By maintaining separate flow paths within the connector 3400, the reaction (e.g., crosslinking) between the first component 1 and the second component 2 can be performed outside of the connector 3400 (i.e., within the delivery member 3500), thereby limiting the likelihood of clogging with the connector 3400. In this manner, the connector 3400 can be used for multiple injections.

The drive assembly 3150 can be any suitable assembly or mechanism that produces a drive force to convey the first biomaterial component 1 and the second biomaterial component 2 from the container assembly 3300. As shown, the drive assembly 3150 includes a drive member 3160 having an end portion 3162 that is operably coupled to the container assembly 3300 (specifically, the first plunger 3320 and the second plunger 3340) such that, upon actuation, the drive assembly 3150 can convey the first component 1 and the second component 2 from the container assembly 3300. The drive assembly 3150 can include any suitable mechanism for producing the drive force. For example, in some embodiments, the drive assembly can include an electromechanical driver (not shown in FIGS. 12-14) to produce the drive force. Such electromechanical drivers can include, for example, a motor-driven linear actuator, a hydraulic actuator (e.g., that includes a pump driven by an electronic component), a magnetic-based actuator, a pneumatic actuator that includes an electromechanical valve to control a pressure applied to the drive member 3160, or any other suitable electromechanical driver of the types described herein.

The electronic control system 3200 controls the electromechanical driver and any other suitable aspect of the drive assembly to control the delivery characteristics of the first component 1, the second component 2, and/or the delivered product, as described herein. Moreover, the electronic control system 3200 can cause the drive assembly 3150 to produce separate movement associated with a priming operation and an injection operation. The electronic control system 3200 can be similar to (and include any of the features of) the electronic control system 2200. For example, although not shown in FIGS. 12-14, the electronic control system 3200 can include one or more sensors, one or more processors, one or more memory components, and various modules, such as a drive module and a user interface module. As shown, the electronic control system 3200 includes an actuator (or trigger) 3230, a first user input switch 3232 (also referred to as a "prime switch"), and a second user input switch 3233 (also referred to as an "injection switch"). The electronic control system 3200 is powered by a power supply 3240. The power supply 3240 can be any suitable power supply, such as a battery (including a rechargeable battery), an AC to DC converter (e.g., to facilitate an AC powered device). The actuator 3230, the prime switch 3232, and the injection switch 3233 can each provide input to the electronic control system 3200 via a user interface module (not shown, but which can be similar to the user interface module 2206 described above).

In use, the electronic control system 3200 can control the drive assembly 3150 based on the user input received via the prime switch 3232 and the injection switch 3233. Specifically, the electronic control system 3200 (and/or the drive module) is configured to produce a prime signal to cause the drive member 3160 to move a prime distance when prime switch 3232 is actuated. The prime signal can be an electronic signal (e.g., a current, a number of pulses or the like) that causes an electromechanical driver of the drive system 3150 to move the drive member 3160 by a predetermined distance (i.e., the prime distance) that is sufficient to prime the system 3000 in preparation for (and before commencement of) and injection operation. In some embodiments, the electronic control system 3200 (and/or the drive module) is configured to produce the prime signal in response to actuation of the prime switch 3232 and the actuator 3230. For example, in some embodiments, the user can first actuate the prime switch 3232 to place the electronic control system 3200 into a prime mode. Then after the user actuates the actuator 3230, the electronic control system 3200 (and/or the drive module) produces the prime signal to initiate the prime operation (movement of the drive member 3160).

Additionally, the electronic control system 3200 (and/or the drive module) is configured to produce an injection signal to cause the drive member 3160 to move an injection distance when injection switch 3233 is actuated. The injection signal can be an electronic signal (e.g., a current, a number of pulses or the like) that causes an electromechanical driver of the drive system 3150 to move the drive member 3160 by a predetermined distance (i.e., the injection distance) that is sufficient to deliver the desired volume of the biomaterial product (e.g., the hydrogel). In some embodiments, the electronic control system 3200 (and/or the drive module) is configured to produce the injection signal in response to actuation of the injection switch 3233 and the actuator 3230. For example, in some embodiments, the user can first actuate the injection switch 3233 to place the electronic control system 3200 into an injection mode. Then after the user actuates the actuator 3230, the electronic control system 3200 (and/or the drive module) produces the injection signal to initiate the injection operation (movement of the drive member 3160).

In some embodiments, the electronic control system 3200 (and/or the drive module) can produce, control, and/or adjust a drive signal to control the electromechanical driver to maintain an exit force of the hydrogel being conveyed out of the delivery member 3500 below an exit force threshold, as described herein. In some embodiments, the electronic control system 3200 (and/or the drive module) can produce, control, and/or adjust a drive signal to control the electromechanical driver to maintain a velocity of the first component 1, the second component 2, and/or the delivered biomaterial product within a desired velocity range, as described herein.

In some embodiments, the electronic control system 3200 (and any of the electronic control systems described herein) is configured to detect an error condition associated with the delivery system 3000 and/or the delivery device 3100 and produce a notification to the user. For example, in some embodiments, the electronic control system 3200 includes an output device (e.g., a light, a speaker, or a vibration device). On the condition that injection switch 3233 is actuated but the prime operation has not been completed, the electronic control system 3200 can produce an error signal. In this manner, the electronic control system 3200 can eliminate or reduce the likelihood of an improper injection being completed (due to the failure to properly prime the device). In some embodiments, the electronic control system 3200 (and any of the electronic control systems described herein) includes a sensor configured to produce a feedback signal indicating whether the connector 3400 is coupled to the container assembly 3300. The electronic control system 3200 (and/or the drive module) can produce an error signal when the feedback signal indicates that the connector 3400 is not coupled to the container assembly 3300. In this manner, the electronic control system 3200 can eliminate or reduce the likelihood of an improper injection being completed if the connector 3400 is not properly coupled to the container assembly 3300. Specifically, the error signal can cause the output device to produce any one of a visual, audible, or tactile output. In some embodiments, the error signal can disable the injection signal or the drive signal, or can otherwise prevent movement of the drive member 3160.

Figure 15:
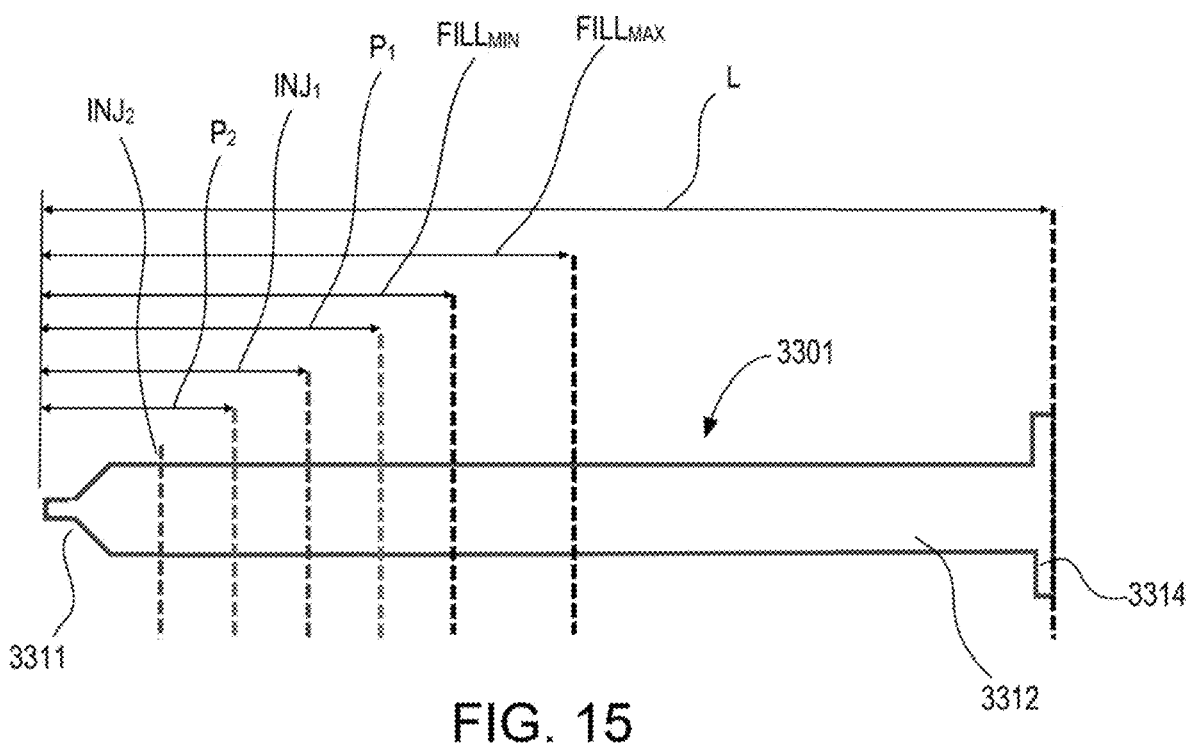
FIG. 15 is a schematic diagram of a container showing various operating positions and travel of a plunger of a delivery apparatus according to an embodiment.

In some embodiments, the system 3000 can be used to perform multiple injections using the same container assembly 3300. For example, in some embodiments, the system 3000 (and any of the systems described herein) can be used to deliver a biomaterial product (e.g., a hydrogel) to occlude each of the two vas deferens of a patient. In such embodiments, the container assembly 3300 can include a sufficient amount of the first component 1 and the second component 2 to deliver two separate biomaterial products to the patient (one for each vas deferens). Such methods are described below with reference to the methods 20 and 30. In such embodiments, the system 3000 can be primed two times (once before each of the injection events). The two priming events and the two injection events are described schematically in FIG. 15, which shows a schematic illustration of the first container 3301. As shown, the first container 3301 has a first end portion 3311 and a second end portion 3312. The second end portion 3312 includes a flange 3314, which serves as a reference point for identifying the distances through which the elastomeric member 3315 (not shown in FIG. 15) is moved during each of the prime and injection operations.

As shown, the first container 3301 (and any of the containers described herein) can be filled with the first component prior to being coupled within the delivery device 3100. The first container 3301 can be prefilled with the first component or alternative the user can mix and/or prepare the first component on site and then manually fill the first container 3301 before use. As shown, the amount of the first component within the first container 3301 will vary between a maximum fill volume (identified as FILLmax) and a minimum fill volume (identified as FILLmin). In use, upon initiating the first prime event, the movable member 3160 will move through a first prime distance from a starting position (i.e., a home position of the drive member 3160 and/or the drive assembly 3150) to the first prime position (identified as $P_1$). During the first prime event, the first component 1 and the second component 2 will be conveyed from the first container 3301 and the second container 3302, respectively, and through the first lumen 3411 and the second lumen 3412, respectively, of the connector 3400. Because the first component 1 is separate from the second component 2 within the connector 3400, no crosslinking of the components takes place during the first prime operation. The user can wipe the residual material from the tip of the connector 3400. The system 3000 is then ready to be coupled to the delivery member 3500 to complete the first injection.

In use, upon initiating the first injection event, the movable member 3160 moves through a first injection distance from the first prime position $P_1$ to the first injection position (identified as $INJ_1$). During the first injection event, additional amounts of the first component 1 and the second component 2 will be conveyed from the first container 3301 and the second container 3302, respectively, through the connector 3400, into a mixing volume of the delivery member 3500, and through the delivery member 3500 to the target location.

Because the first component 1 is separate from the second component 2 within the connector 3400, no crosslinking of the components takes place during the first prime operation. The user can wipe the residual material from the tip of the connector 3400. The system 3000 is then ready to be coupled to the delivery member 3500 to complete the crosslinking of the two components and subsequently the first injection. As described herein, during the first injection event, the delivery characteristics of the first component 1 and the second component 2 (i.e., the velocity, the flow rate, the maximum delivery force) can be controlled to ensure that the delivered biomaterial product (e.g., the hydrogel) is fully formed within the delivery member 3500 before being conveyed to the target location, and is conveyed in a repeatable, accurate manner that does not damage the target tissue. After completion of the first injection event the connector 3400 can be disconnected from the delivery member 3500.

The second prime event can be initiated to cause the movable member 3160 to move through a second prime distance from the first injection position $INJ_1$ to a second prime position (identified as $P_2$). The second prime event can be similar to the first prime event, as described above. Because the second prime event starts with the movable member 3160 at the first injection position $INJ_1$, however, the system 3000 does not need to account for variability in the initial fill amount of the first container 3301. Accordingly, the second prime distance can be less than the first prime distance. After the second prime event, the user can again wipe the residual material from the tip of the connector

3400. The system 3000 is then ready to be coupled to a second delivery member 3500 (separate from the first delivery member) to complete the second injection. During the second injection event, the movable member 3160 moves through a second injection distance from the second prime position $P_2$ to the second injection position (identified as $INJ_2$). During the second injection event, additional amounts of the first component 1 and the second component 2 will be conveyed from the first container 3301 and the second container 3302, respectively, through the connector 3400, into a mixing volume of the second delivery member 3500, and through the second delivery member 3500 to the target location. The second injection event is similar to the first injection event described above. Upon completion of the second injection event, the container assembly 3300 and delivery member 3500 can be removed from the device 3100 and discarded.

As described above, the drive member 3160 and/or the drive assembly 3150 is associated with a starting (or home) position, which is the position from which the drive member 3160 initially begins a sequence of operations and/or to which the drive member 3160 returns after completing a sequence of operations. The home position can be maintained at a constant (or substantially constant) distance from the flange 3314 of the first container 3301 (and any of the containers described herein). By maintaining a constant home position relative to the container assembly 3300, the device 3100 can repeatably deliver the desired amounts of the components for multiple different operations, with the same or different patients, using multiple different container assemblies 3300.

Figure 16:
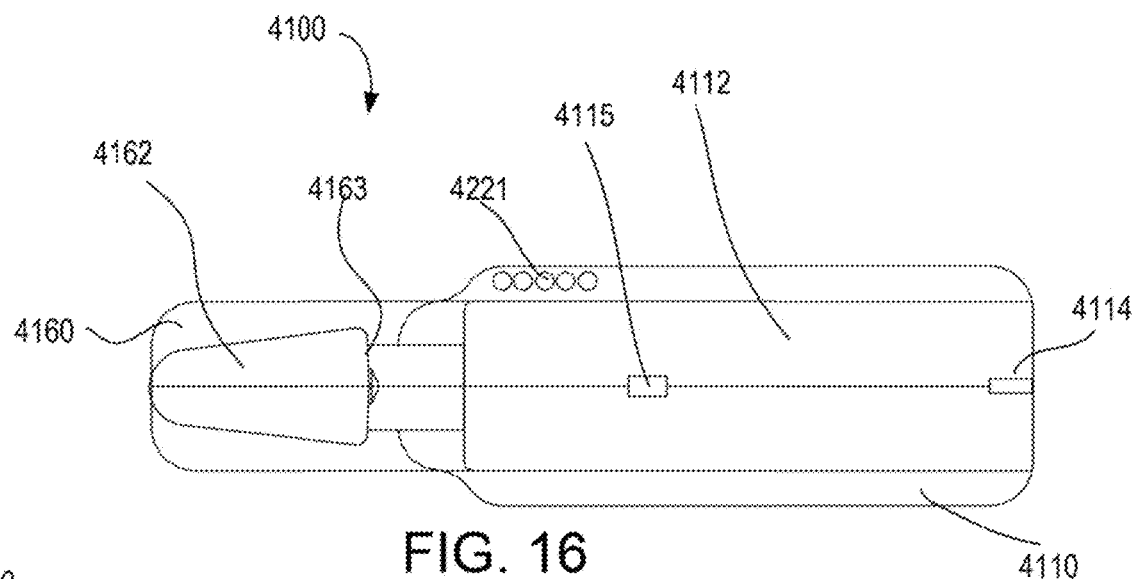
FIG. 16 is a top view of a portion of a delivery system according to an embodiment.
Figure 17:
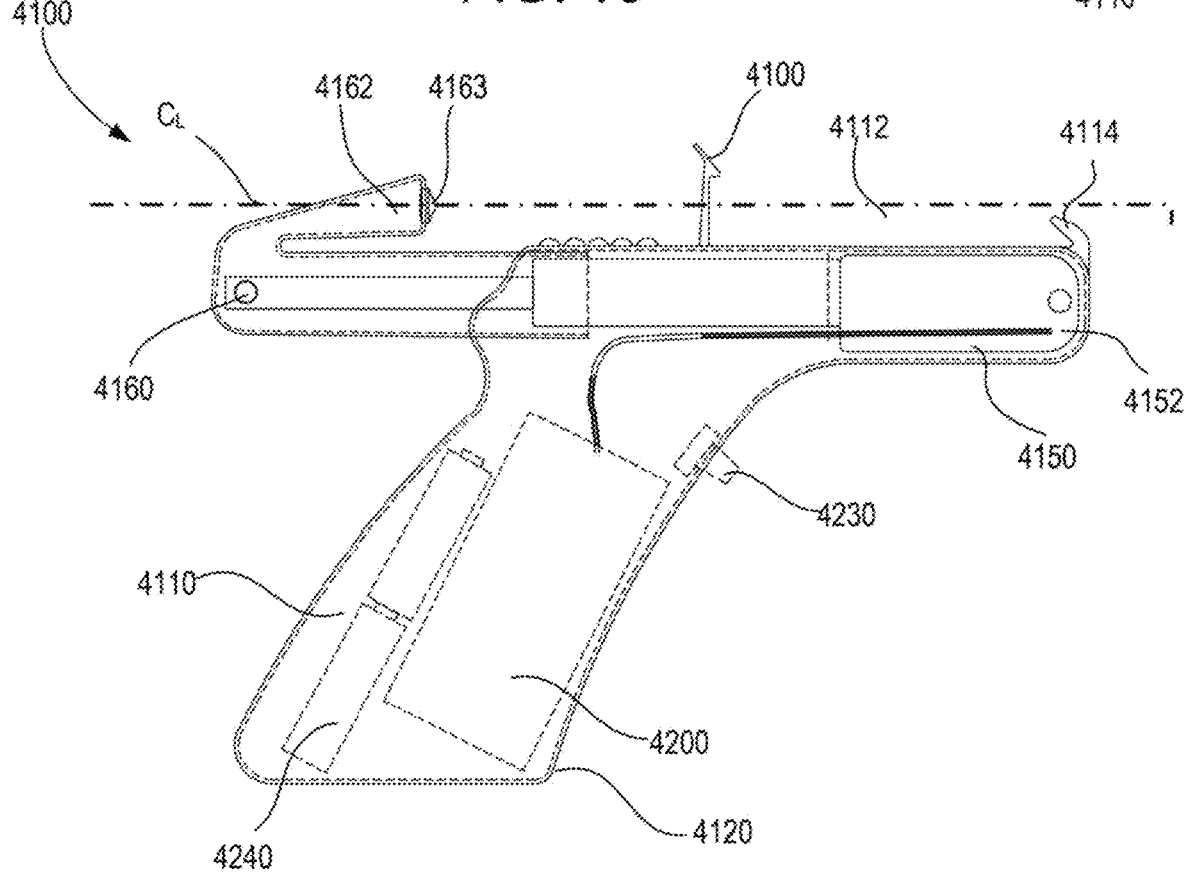
FIG. 17 is a side cross-sectional view of the delivery system of FIG. 16.
Figure 18:
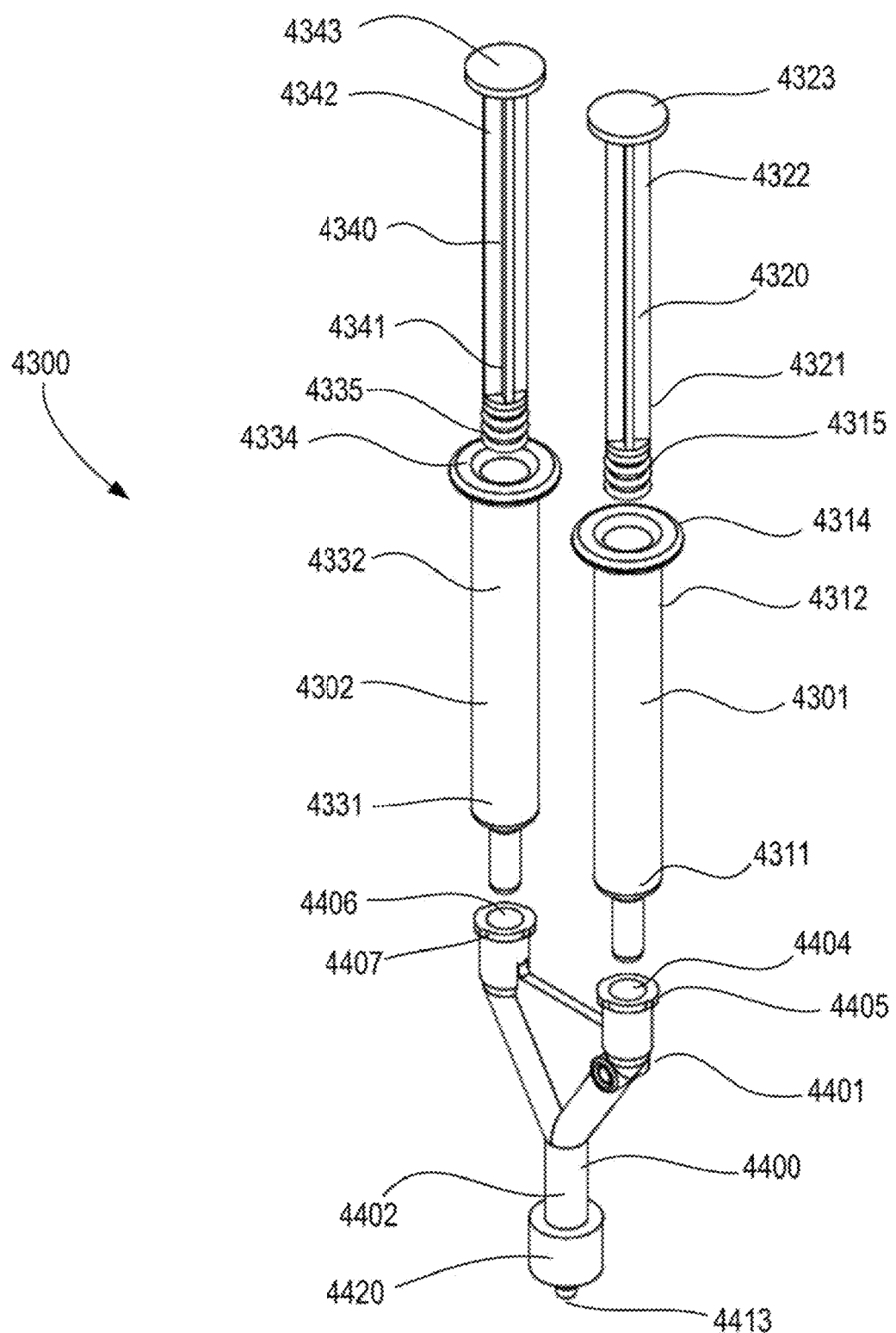
FIG. 18 is an exploded view of a container assembly and a connector according to an embodiment.
Figure 19:
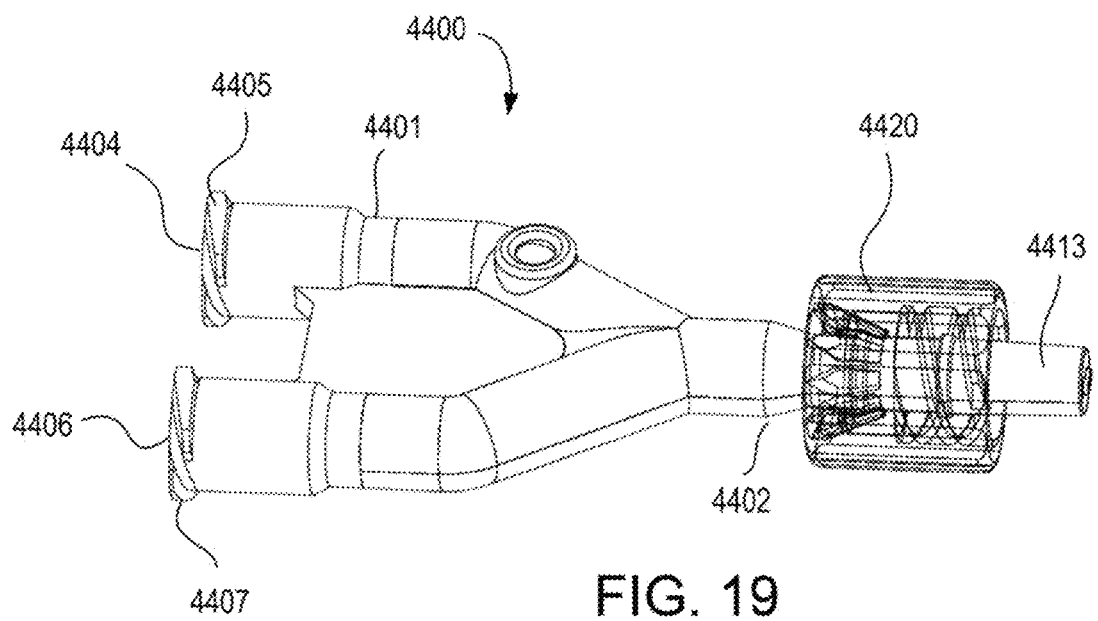
FIG. 19 is a perspective view of the connector of FIG. 18 showing a coupler for removably coupling to a delivery member.
Figure 20:
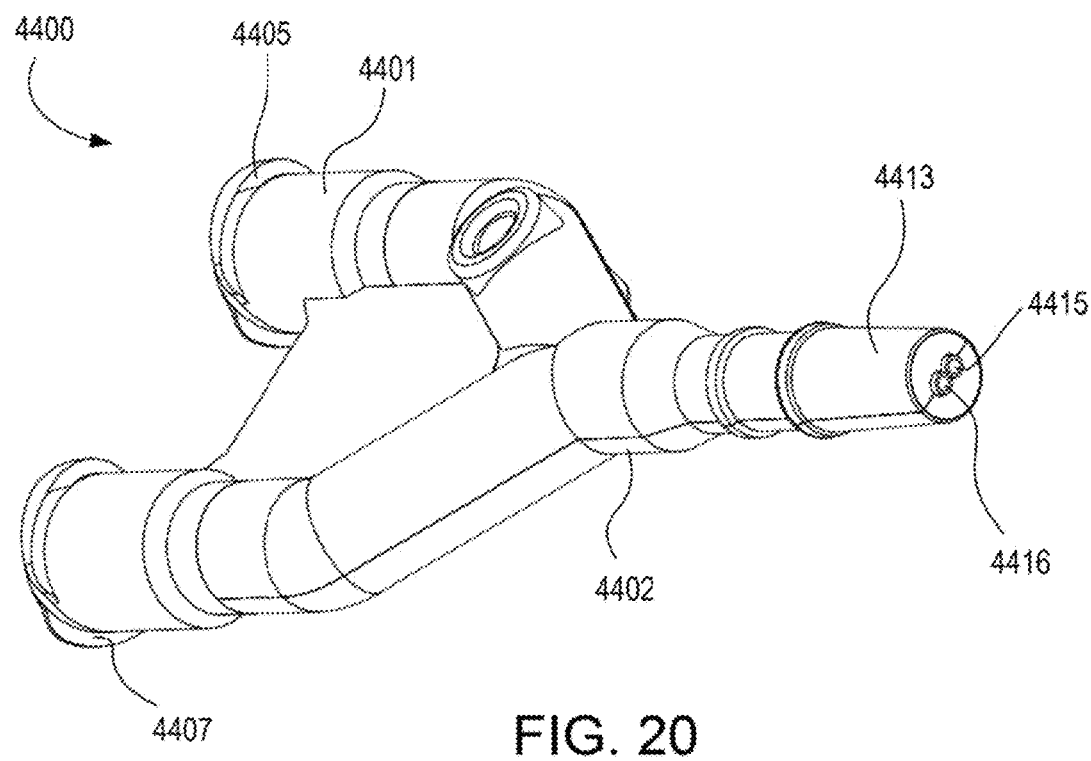
FIG. 20 is a perspective view of the connector of FIG. 19 with the coupler removed.

In some embodiments, container assembly can include a cartridge or other structure to ensure that the containers therein coupled to the delivery device in the desired position (i.e., relative to the home position of the drive assembly). By using a cartridge that includes indexing and/or alignment features, the likelihood of misalignment and/or improper positioning by the user can be minimized. For example, FIGS. 16-31 are various views of a system 4000 according to an embodiment, that includes, among other things, a cartridge for positioning of the container assembly. The system 4000 includes the delivery device 4100 (e.g., FIGS. 16 and 17), a container assembly 4300 (e.g., FIGS. 18 and 22), a connector 4400 (e.g., FIGS. 18-20), and a delivery member 4500 (e.g., FIGS. 27 and 28). The delivery device 4100 includes a housing 4110, a drive assembly 4150, and an electronic control system 4200.

The housing 4110 includes a container receiving portion 4112 configured to receive at least a portion of the container assembly 4300. The container receiving portion 4112 is an opened portion of the housing 4110 that is bounded by a bottom surface against which the container assembly 4300 and/or the cartridge 4350 can be placed. The container receiving portion 4112 includes a first retainer 4114 and a second retainer 4115. As described in more detail below, the first retainer 4114 engages the first engagement portion 4361 of the cartridge 4350 (see FIG. 21) to retain the cartridge 4350 within the housing 4110 in a fixed position. The second retainer 4115 engages the second engagement portion 4363 of the cartridge 4350 (see FIG. 21) to retain the cartridge 4350 within the housing 4110 in the fixed position. The fixed position can be fixed relative to a home position of the drive assembly 4150 and/or the drive member 4160. Additionally, as shown, the second retainer 4115 includes a lock protrusion that can releasably retain the cartridge 4350 within the housing 4110. The second retainer 4115 is deformable and can be deformed to move the lock protrusion from the second engagement portion 4363 to allow the cartridge 4350 to be removed.

The housing 4110 also contains the drive assembly 4150 and the electronic control system 4200. As shown, the housing 4110 includes a handle 4120 that can be gripped and/or manipulated by a user during operation of the device. 4100. The housing 4110 can be made from any suitable material or materials and can provide any suitable structural components to receive and/or retain the portion of the container assembly 4300 and perform any of the functions described herein.

The container assembly 4300 includes a first container 4301 and a second container 4302. The first container 4301 has a first end portion 4311, a second end portion 4312, and includes an elastomeric member (or stopper) 4315 therein. The second end portion 4312 includes a flange 4314 that can be coupled within the cartridge 4350, as described below. The first container 4301 defines a volume that is bounded on one side by the elastomeric member 4315 and that contains a first component. The first container 4301 includes a first plunger 4320 having a first end portion 4321 and a second end portion 4322. The first end portion 4321 is movably disposed within the first container 4301 such that movement of the first plunger 4320 will cause movement of the elastomeric member 4315 to convey the first component from the first container 4301. The second end portion 4322 of the first plunger 4320 terminates in a flange 4323 that is operably coupled to (e.g., is configured to engage) the drive member 4160. The second container 4302 has a first end portion 4331, a second end portion 4332, and includes an elastomeric member (or stopper) 4335 therein. The second end portion 4332 includes a flange 4334 that can be coupled within the cartridge 4350, as described below. The second container 4302 defines a volume that is bounded on one side by the elastomeric member 4335 and that contains a second component. The second container 4302 includes a second plunger 4340 having a first end portion 4341 and a second end portion 4342. The first end portion 4341 is movably disposed within the second container 4302 such that movement of the second plunger 4340 will cause movement of the elastomeric member 4335 to convey the second component from the second container 4302. The second end portion 4342 terminates in a flange 4343 that is operably coupled to (e.g., is configured to engage) the drive member 4160

Figure 21:
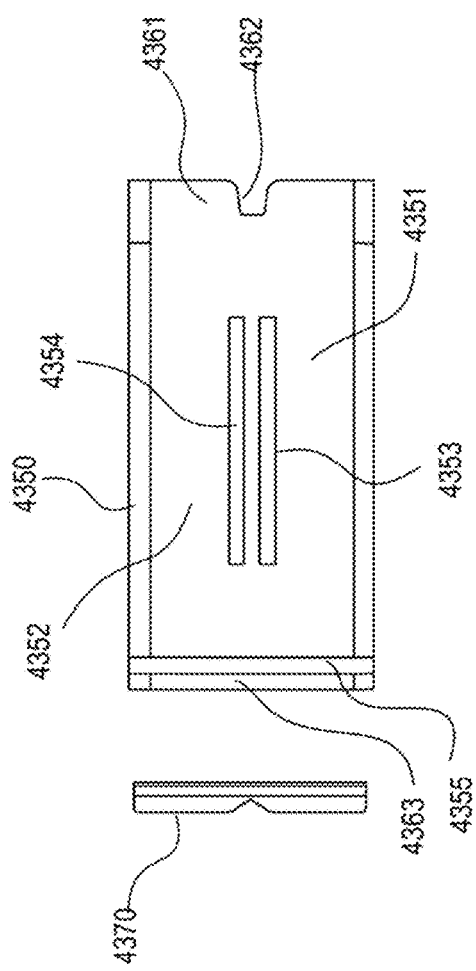
FIG. 21 is a top view of portion of a cartridge for holding the container assembly of the delivery system shown in FIG. 18.
Figure 22:
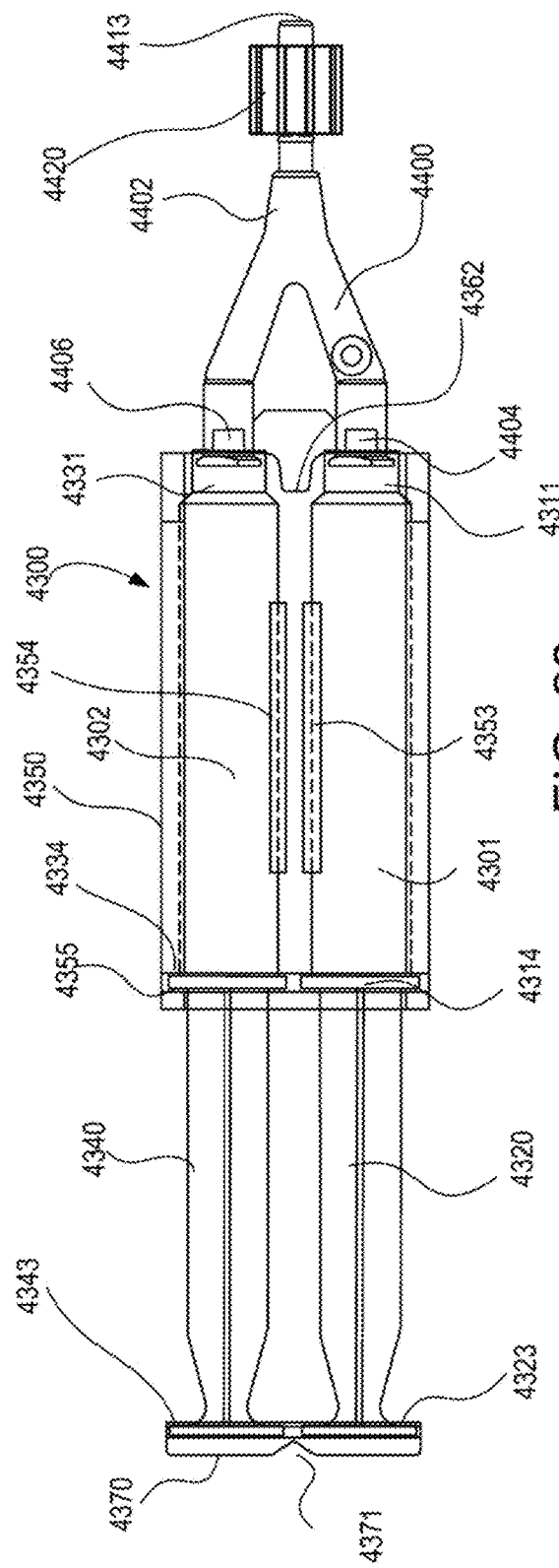
FIG. 22 is a top view of the container assembly and connector of FIG. 18 installed on the cartridge of FIG. 21.

Referring to FIGS. 21 and 22, the cartridge 4350 defines a first recess or opening 4351 that receives a portion of the first container 4301 (i.e., the container body) and a second recess or opening 4352 that receives a portion of the second container 4302 (i.e., the container body). The cartridge 4350 includes a first retainer (or clip) 4353, a second retainer (or clip) 4354, a first engagement portion 4361, and a second engagement portion 4363. The first retainer 4353 forms a boundary of the first recess 4351 and engages the container body of the first container 4301 to retain the first container 4301 within the cartridge. The second retainer 4354 forms a boundary of the second recess 4352 and engages the container body of the second container 4302 to retain the second container 4302 within the cartridge. Either or both of the first retainer 4353 and the second retainer 4354 can be deformable to form an interference fit with the respective container body. In this manner, the containers can be securely fastened within the cartridge 4350. The first retainer 4353 and the second retainer 4354 can position the containers in a fixed position in a first direction, i.e., normal to the longitudinal center line CL of the container assembly 3300 and/or the delivery device 3100. The cartridge 4350 define a flange slot 4355 within which the flange 4314 (of the first container 3301) and the flange 4334 (of the second container 3302) are received. In this manner, the position of the containers along the center line CL can be fixed.

The first engagement portion 4361 of the cartridge define a notch 4362 that receives and/or matingly engages the first retainer 4114 of the housing 4110. The second engagement portion 4363 includes a surface against which the lock protrusion of the second retainer 4115 can engage to removably retain the cartridge 4350 (and therefore, the container assembly 3300) within the housing 4110 (see e.g., FIGS. 24 and 25). This arrangement allows the cartridge 4350 to be coupled to the delivery device 4100 in a fixed position relative to a home position associated with the drive assembly 4150. In other embodiments, the housing can define one or more recesses or notches and the cartridge can include one or more protrusions to securely (and removably) couple the cartridge 4350 to the housing 4110.

The plunger link 4370 is configured to be coupled to the flange 4323 of the first plunger 4320 and the flange 4343 of the second plunger 4340. Specifically, the plunger link 4370 defines a retention slot 4371 and includes a surface against which the drive member 4160 can exert a drive force. The retention slot 4371 receives the flange 4323 and the flange 4343. The plunger link 4370 facilitates the use of a single drive assembly 4350 to produce the drive force to repeatably move both the first plunger 4320 and the second plunger 4340. In other embodiments, however, a plunger link is not included. In some embodiments, the first plunger 4320 and the second plunger 4340 can include an engagement portion to couple or attach to the pistons (or stoppers) within each container.

The first component and the second component can be any of the biomaterial components described herein. For example, in some embodiments, the first component and the second component can each be a water soluble component (e.g., monomer, macromer, polymer, or the like) that is capable of crosslinking (e.g., with the other component) to form a hydrogel (as the delivered biomaterial product). In some embodiments, the first component and the second component are formulated such that the resulting hydrogel has a gelation time of less than 5 minutes. In other embodiments, the first component and the second component are formulated such that the resulting hydrogel has a gelation time of less than 2 minutes. In other embodiments, the first component and the second component are formulated such that the resulting hydrogel has a gelation time of less than 1 minute. In yet other embodiments, the first component and the second component are formulated such that the resulting hydrogel has a gelation time of less than 30 seconds. In some embodiments, the first component is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent. In some embodiments the polysaccharides may be modified with different functional groups. In some embodiments the polysaccharides and proteins may range in molecular weight from 10,000-1,000,000 grams/mole. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from 1,000-1,000,000 grams/mole. The hydrogel can be any of the hydrogels described herein and can have any of the characteristics as indicated herein. For example, in some embodiments, the formed hydrogel can be at least 90 percent water.

The container assembly 4300 is configured to be coupled to the connector 4400, which is, in turn, coupled to a delivery member 4500. By having the containers as separate articles from the connector 4400 and delivery member 4500, the first component and the second component can each be prepared within the container assembly 4300 (e.g. via mixing, dilution, etc.) separately from when connector 4400 is attached. In other embodiments, however, the container assembly 4300 can be provided as a prefilled assembly and include prefilled syringes or prefilled cartridges. In some embodiments, the prefilled assembly can be provided with premixed components, or the prefilled assembly can be provided with separate powder(s) and solvent(s) that can be combined prior to use with the delivery device 4100.

The connector 4400 can be similar to any of the connectors described herein, and includes a first (or input) end portion 4401 and a second (or output) end portion 4402. The first end portion includes a first inlet 4404 that is coupled to a tip (or connector) of the first container 4301 (e.g., via the flange 4405, which can be coupled to a luer connector, not shown, of the first container 4401). The first end portion includes a second inlet 4406 that is coupled to a tip (or connector) of the second container 4302 (e.g., via the flange 4407, which can be coupled to a luer connector, not shown, of the second container 4402). The second end portion 4402 is configured to be coupled to the delivery member 4500 (see FIG. 27). The second end portion 4402 includes a fitting 4420, which can rotate relative to the connector 4400 to couple to a mating flange of the hub 4520 of the delivery member 4500. In some embodiments, the fitting 4420 and the connector 4400 can include one or more indicators to provide a visual cue to a user to confirm that a secure connection has been made. In some embodiments, the connector 4400 and the delivery member 4500 can include one or more indicators to provide a visual cue to a user to confirm that a secure connection has been made. In some embodiments, a sensor can be provided in (or associated with) the connector 4400 and/or the delivery member 4500 to detect a secure connection. For example, the sensor can communicate with the electronic control system 4200 to provide an audible or visual cue to the user that a secure connection has been made, or a warning if a secure connection has not been made. In some embodiments, the sensor can communicate with the electronic control system 4200 to prohibit the drive assembly 4150 from operating in the event of an incomplete or improper connection.

Similar to the connector 3400 described above, the connector 4400 defines a first passageway placing the first inlet 4404 in fluid communication with a first outlet 4415 (see FIG. 20) and a second passageway placing the second inlet 4406 in fluid communication with a second outlet 4416. In this manner, the first component can be conveyed from the first container 4301, into the first end portion of the connector 4400, and out of the first outlet 4415 into a mixing volume 4521 of the delivery member 4500. Similarly, the second component can be conveyed from the second container 4302, into the first end portion of the connector 4400, and out of the second outlet 4416 into the mixing volume 4521 of the delivery member 4500. Thus, the connector 4400 maintains the first component separate from the second component, and the two components are conveyed into and mixed within the hub 4520 of the delivery member 4500. By maintaining separate flow paths within the connector 4400, the reaction (e.g., crosslinking) between the first component and the second component can be performed outside of the connector 4400 (i.e., within the delivery member 4500), thereby limiting the likelihood of clogging with the connector 4400. In this manner, the connector 4400 can be used for multiple injections.

Figure 27:
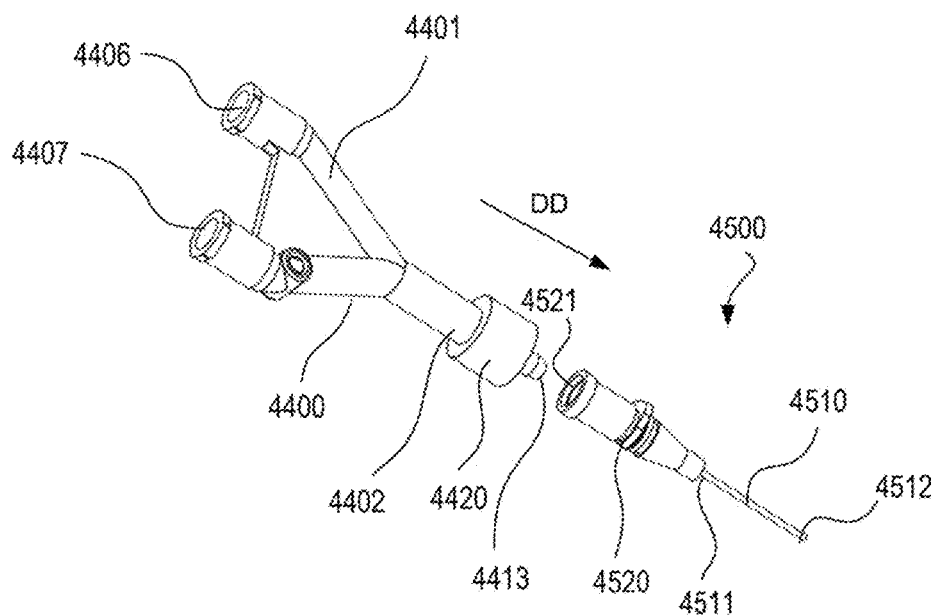
FIG. 27 is a perspective view of a connector and a delivery member according to an embodiment.
Figure 28:
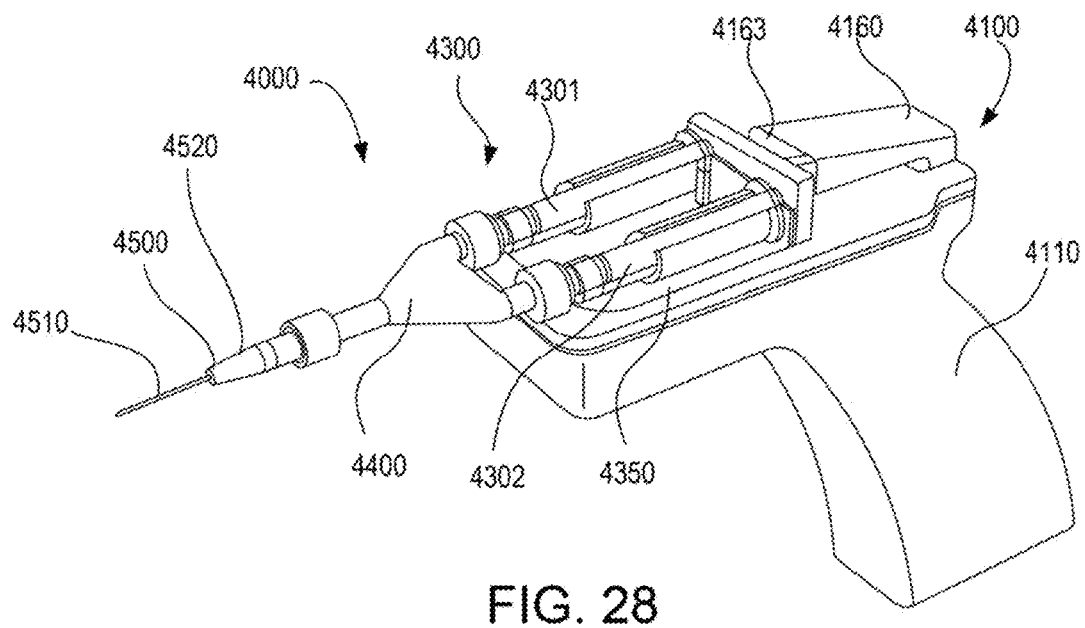
FIG. 28 is a perspective view of a delivery member mounted onto connector of the delivery system of FIG. 17 according to an embodiment.
Figure 29:
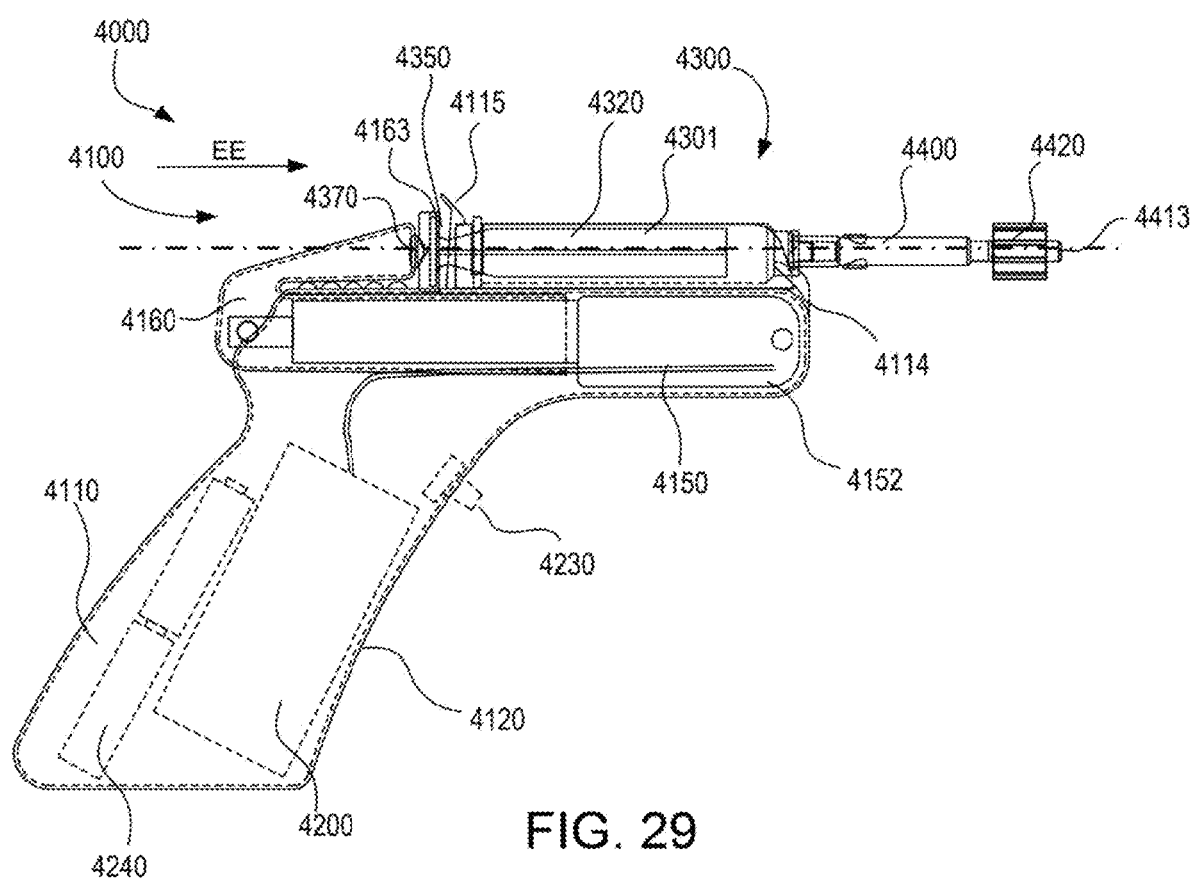
FIG. 29 is a side cross-sectional view of the delivery system of FIG. 28, after delivery of the components from the container assembly.
Figure 30:
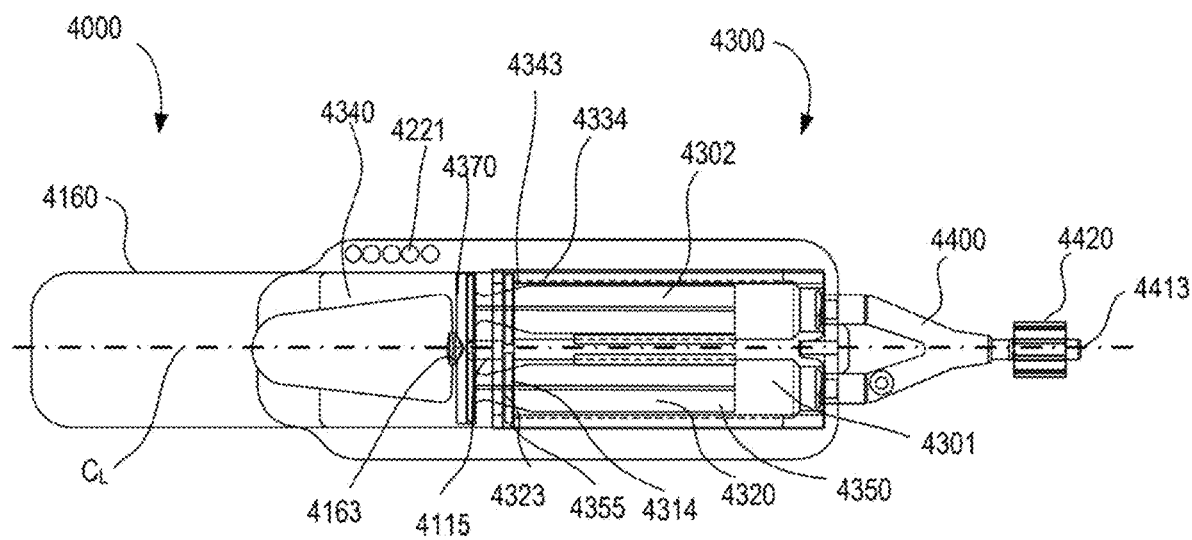
FIG. 30 is a top view of the delivery system of FIG. 28, after delivery of the components from the container assembly.
Figure 31:
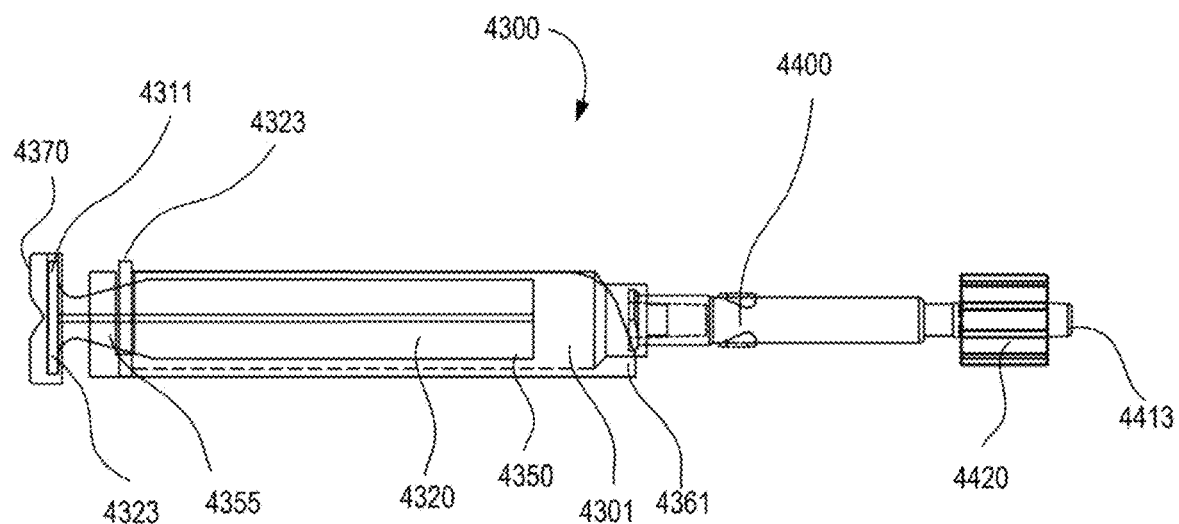
FIG. 31 is a partial side cross-sectional view of the cartridge, container assembly, and connector in the delivery system of FIG. 28 after having been removed from the delivery device.

The delivery member 4500 includes a catheter 4510 coupled to a hub 4520. The hub 4520 includes a flange or other suitable fastening mechanisms by which the hub 4520 can be coupled to the fitting 4420 of the connector 4400. As shown in FIG. 27, the hub 4520 defines a mixing volume 4521 within which the first component and the second component can be conveyed and mixed together. The catheter 4510 includes a first end 4511 coupled to the hub 4520 and a second end 4512 that can be inserted into a body lumen or other target location.

The drive assembly 4150 can be any suitable assembly or mechanism that produces a drive force to convey the first biomaterial component and the second biomaterial component from the container assembly 4300. As shown, the drive assembly 4150 includes an electromechanical driver 4152 and a drive member 4160. The electromechanical driver 4152 can be any of the electromechanical drivers described herein, and in this embodiment, is a linear actuator powered by a stepper motor that produces the drive force. The drive member 4160 has an end portion 4162 that is operably coupled to the container assembly 4300 by a contact surface 4163. Specifically, the contact surface 4163 can engage the corresponding surface of the plunger link 4370 such that, upon actuation, the drive assembly 4150 can move the first plunger 4320 and the second plunger 4340 along the longitudinal center line CL. In some embodiments, the drive assembly 4150 can include one or more springs and dampers in addition to, or in lieu of, the electromechanical driver 4152 to provide controlled actuation of the first plunger 4320 and the second plunger 4340 along the longitudinal center line CL.

The electronic control system 4200 controls the electromechanical driver 4152 and other aspects of the drive assembly 4150 to control the delivery characteristics of the first component, the second component, and/or the delivered product, as described herein. Moreover, the electronic control system 4200 can cause the drive assembly 4150 to produce separate movement associated with a priming operation and an injection operation, as described above with reference to the system 3000. The electronic control system 4200 can be similar to (and include any of the features of) the electronic control system 2200 and the electronic control system 3200. For example, although not shown, the electronic control system 4200 can include one or more sensors, one or more processors, one or more memory components, and various modules, such as a drive module and a user interface module. As shown, the electronic control system 4200 includes an actuator (or trigger) 4230 and a set of output devices 4221. Although not shown, the electronic control system 4200 can include various user input switches, such as a prime switch and/or an injection switch, as described above with reference to the system 3000. The electronic control system 4200 is powered by a power supply 4240. The power supply 4240 can be any suitable power supply, such as a battery (including a rechargeable battery), an AC to DC converter (e.g., to facilitate an AC powered device). The actuator 4230 can provide input to the electronic control system 4200 via a user interface module (not shown, but which can be similar to the user interface module 2206 described above).

In use, the electronic control system 4200 can control the drive assembly 4150 based on the user input received to produce any of a prime signal, an injection signal, and a drive signal, as described above. For example, the electronic control system 4200 (and/or the drive module) can produce, control, and/or adjust a drive signal to control the electromechanical driver to maintain an exit force of the biomaterial product (e.g., hydrogel) being conveyed out of the delivery member 4500 below an exit force threshold, as described herein. In some embodiments, the electronic control system 4200 (and/or the drive module) can produce, control, and/or adjust a drive signal to control the electromechanical driver to maintain a velocity of the first component, the second component, and/or the delivered biomaterial product within a desired velocity range, as described herein.

Figure 23:
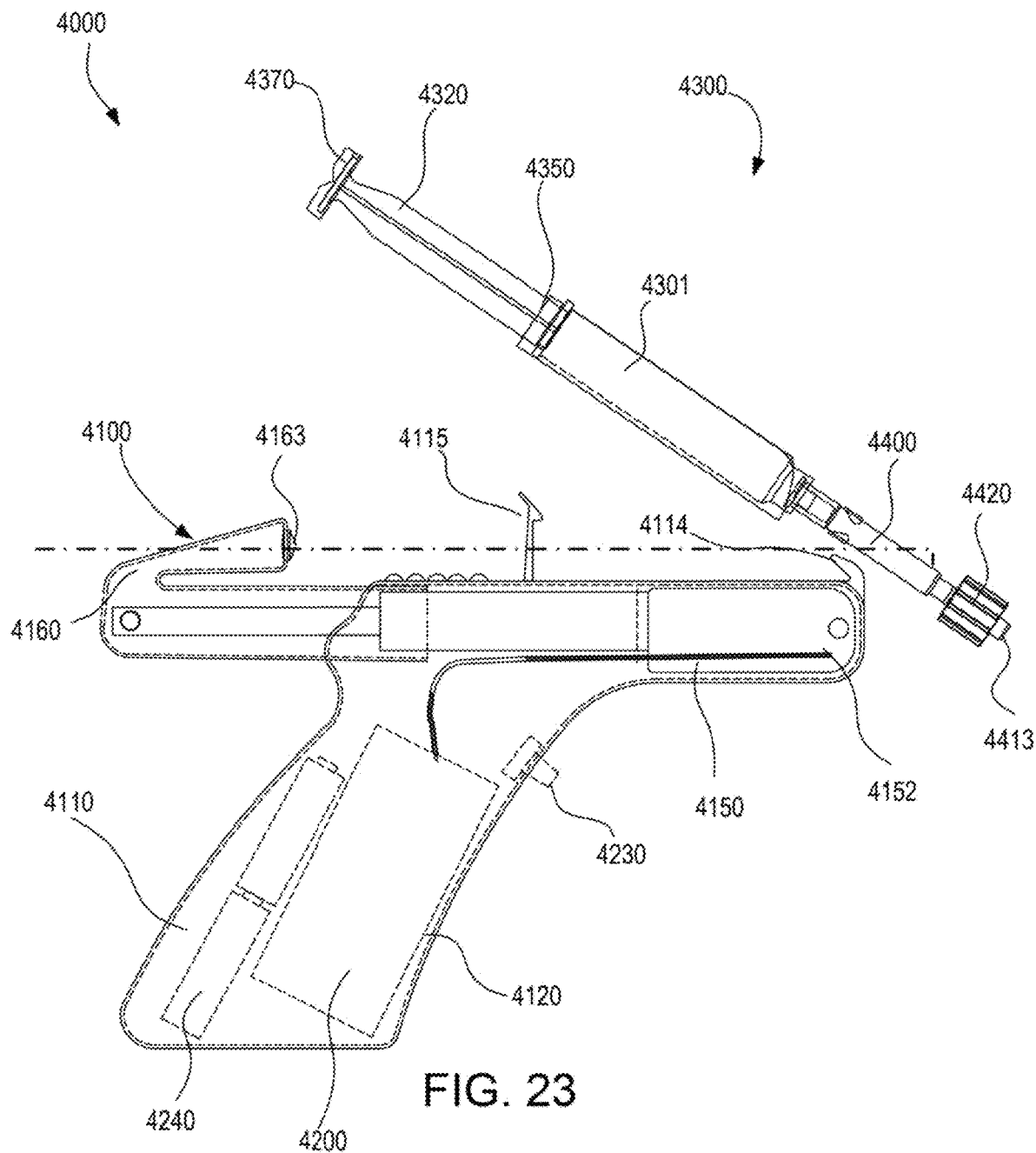
FIGS. 23-24 are side cross-sectional views of the cartridge, container assembly, and connector of FIG. 22 being installed onto the delivery system of FIG. 17.
Figure 24:
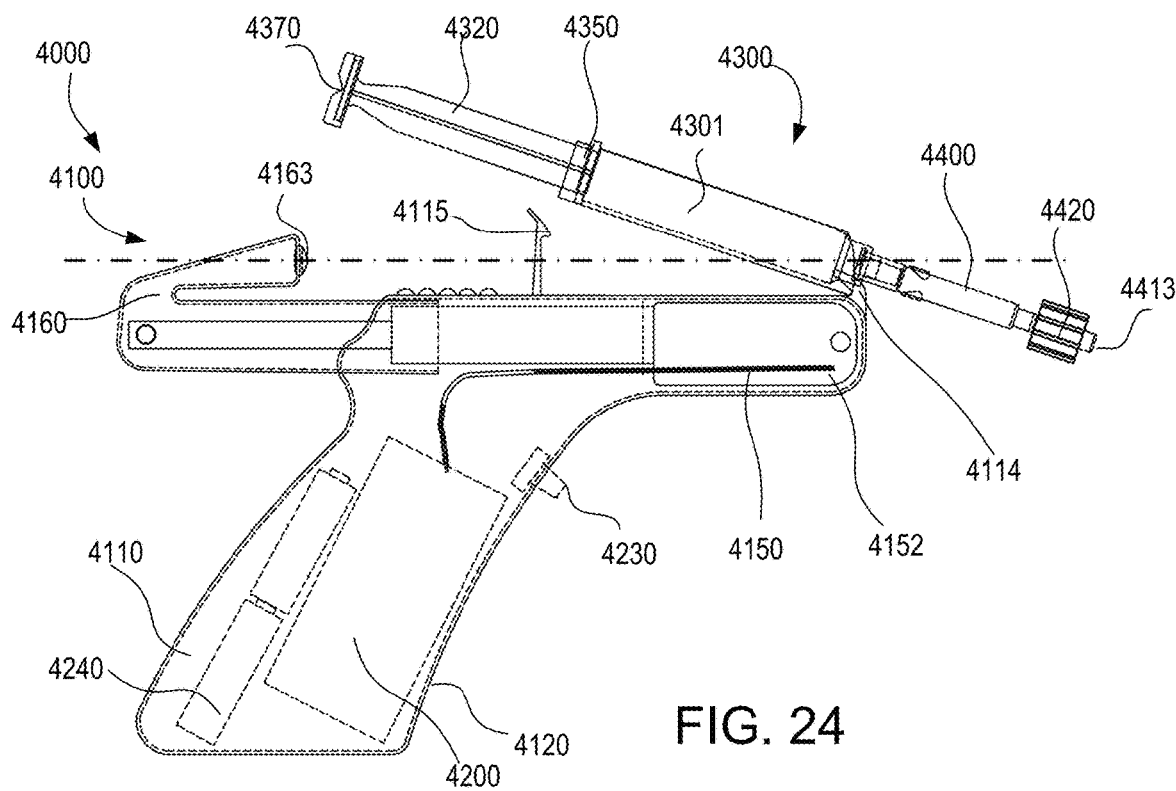
Figure 25:
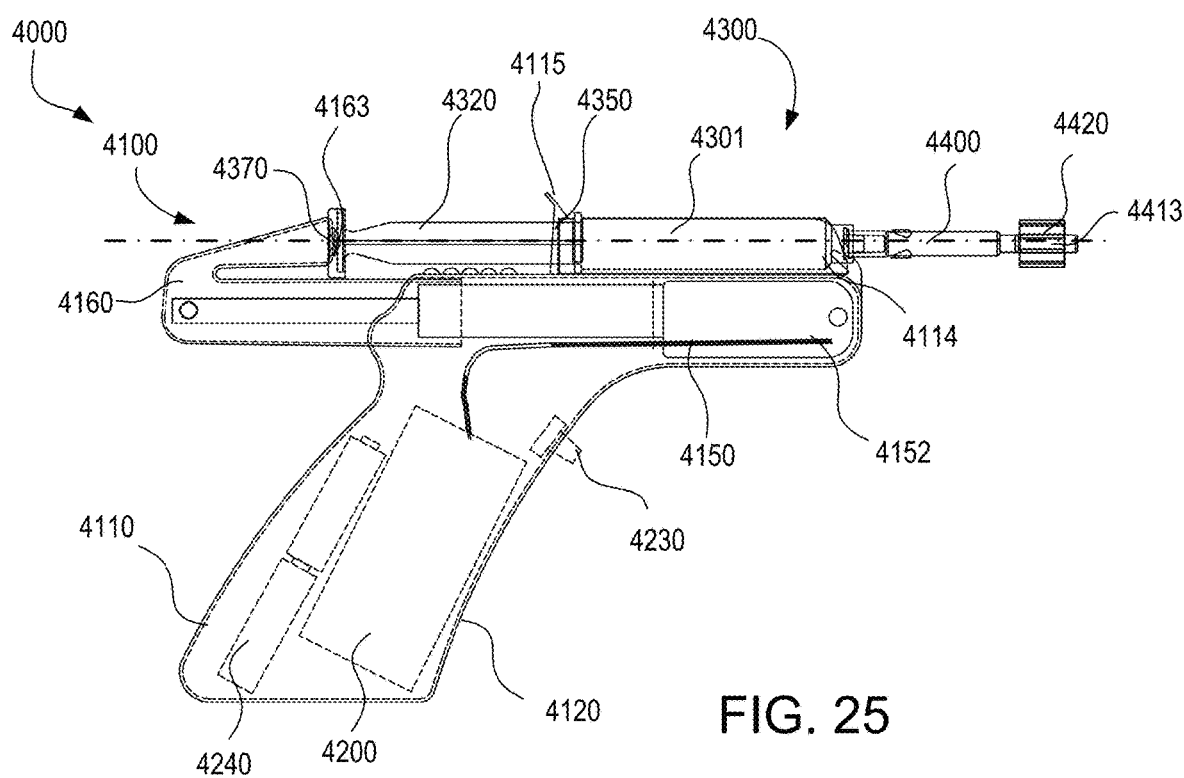
FIG. 25 is a side cross-sectional view of the cartridge, container assembly, and connector installed onto the delivery system of FIG. 17.
Figure 26:
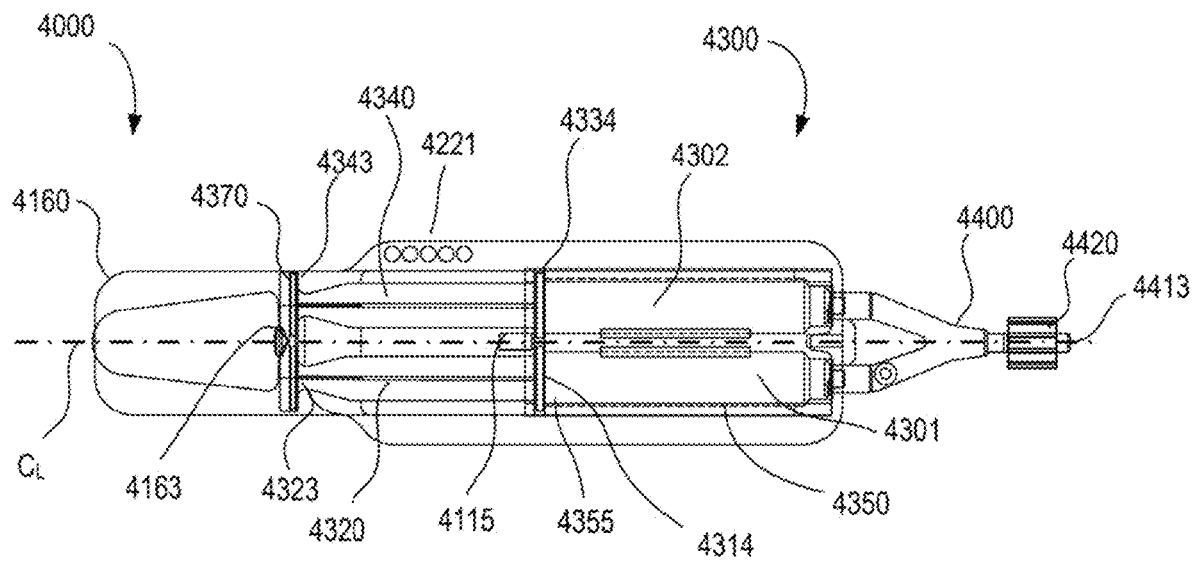
FIG. 26 is a top view of the cartridge, container assembly, and connector installed onto the delivery system of FIG. 17.
Figure 32:
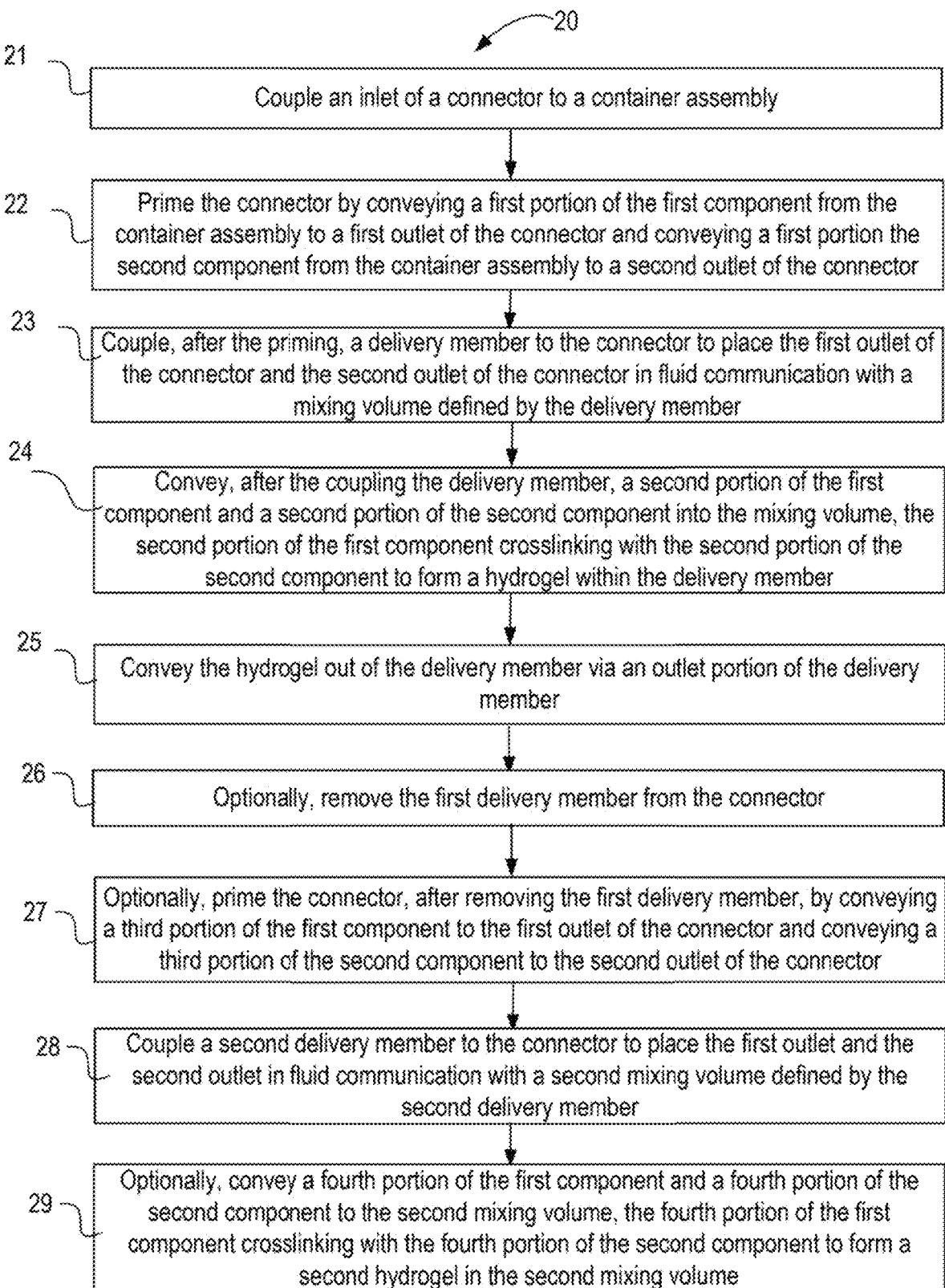
FIG. 32 is a flow chart of a method of delivering a hydrogel according to an embodiment.

FIG. 32 is a flow chart illustrating a method 20 of delivering a biomaterial product, according to an embodiment. Although the method 20 is described in connection with the delivery system 4000, in other embodiments the method 20 can be performed with any of the systems, delivery devices, and components described herein, such as, for example, the delivery systems 1000, 2000, and 3000 and/or the delivery devices 1100, 2100, and 3100 described herein. In some embodiments, the cartridge assembly can be prepared in advance of the delivery operation. For example, the first component can be prepared and loaded into a first container (or syringe) and the second component can be prepared and loaded into a second container (or syringe). Referring to FIG. 22, the containers can then be placed into a cartridge (e.g., the cartridge 4350). As shown in FIGS. 23 and 24, the container assembly 4300 (including the cartridge 4350) can be loaded into the container receiving portion 4112 of the housing 4100. Specifically, the cartridge 4350 can be aligned to receive the first retainer 4114 within the notch 4362. The cartridge 4350 can be rotated, as shown by the arrow CC in FIG. 24, and the second retainer 4115 can be secured about the second engagement portion 4363.

After the container assembly is loaded, the method includes coupling an inlet of a connector to a container assembly, at 21. As shown and described above, the connector (e.g., connector 4400) can be coupled to each of the containers via a luer fitting or the like. The system can then be primed, as described above with respect to the system 3000. Specifically, the method includes priming the connector by conveying a first portion of the first component from the container assembly to a first outlet (e.g., the first outlet 4415) of the connector and conveying a first portion of the second component from the container assembly to a second outlet (e.g., the second outlet 4416) of the connector, at 22. Any residual amounts of the components can optionally be wiped from the end surface 4413 of the connector.

After the priming, a delivery member is coupled to the connector to place the first outlet of the connector and the second outlet of the connector in fluid communication with a mixing volume defined by the delivery member, at 23. Referring to FIG. 27, the connector 4400 can be coupled to the delivery member 4500 by moving the end surface 4413 of the connector into the hub 4520 of the delivery member 4500. The fitting 4420 is then coupled to a flange of the hub 4520. In some embodiments, the fitting 4420 can be a swivel fitting that rotates relative to the connector 4400 to couple to the delivery member. In this manner, the distal surface 4413, including the first outlet 4415 and the second outlet 4416 are within the mixing volume 4521 of the hub. In some embodiments, the portions of the first component and the second component can be conveyed automatically in response to the user actuating an "prime" switch and/or a trigger, as described above with reference the system 3000.

After the delivery member is coupled to the connector, a second portion of the first component and a second portion of the second component are then conveyed into the mixing volume, at 24. The second portion of the first component crosslinks with the second portion of the second component to form a hydrogel (i.e., a delivered biomaterial product) within the delivery member. In some embodiments, the hydrogel has a short gelation time and is conveyed at a low velocity such that the hydrogel is fully formed within the mixing volume. In other embodiments, the formation of the hydrogel (i.e., the crosslinking reaction) can occur in the mixing volume and the catheter portion such that the hydrogel is fully formed upon exiting the delivery member. The method further includes conveying the hydrogel out of the delivery member via an outlet portion of the delivery member, at 25. In some embodiments, the portions of the first component and the second component can be conveyed automatically in response to the user actuating an "inject" switch and/or a trigger, as described above with reference the system 3000.

In some embodiments, the hydrogel can be any of the hydrogels described herein and can be conveyed into a body lumen. For example, in some embodiments, the hydrogel can be conveyed into a vas deferens to form an occlusion therein in order to block sperm as a form of contraception.

In some embodiments, the conveying of the components can be controlled by any of the electronic control systems described herein. For example, in some embodiments, components can be conveyed at a velocity within a predetermined velocity range and/or with a drive force below a drive force threshold. In some embodiments, the hydrogel can be conveyed into a body lumen in less than 30 seconds. In some embodiments, the conveying the hydrogel out of the delivery member includes conveying between about 50 microliters and about 200 microliters in between about 5 seconds and about 20 seconds.

In some embodiments, the method can include use the system and the same container assembly to perform a second injection (e.g., into a second body lumen of the patient). In such embodiments, the method 20 can optionally include removing the first delivery member from the connector, at 26. The connector can then optionally be primed a second time, after removing the first delivery member, at 27. The second priming can be performed by conveying a third portion of the first component to the first outlet of the connector and conveying a third portion of the second component to the second outlet of the connector.

After the second priming, a second delivery member is optionally coupled to the connector to place the first outlet of the connector and the second outlet of the connector in fluid communication with a mixing volume defined by the second delivery member, at 28. After the second delivery member is coupled to the connector, a fourth portion of the first component and a fourth portion of the second component are then conveyed into the mixing volume, at 29. The fourth portion of the first component crosslinks with the fourth portion of the second component to form a second hydrogel (i.e., a second delivered biomaterial product) within the second delivery member.

In some embodiments, any of the systems described herein can be used to deliver a biomaterial product into each of the two vas deferens of a patient. After delivery, the biomaterial product can then occlude the lumen of the vas deferens to block the flow of sperm therethrough. Notably, the procedure can be completed using a single container assembly. This is advantageous because the components used to form each of the delivered biomaterial products are prepared once for both injections. Additionally, the single container assembly is only loaded once into the delivery device. By reducing the number of steps, the procedure can be streamlined and more efficient.

Figure 33:
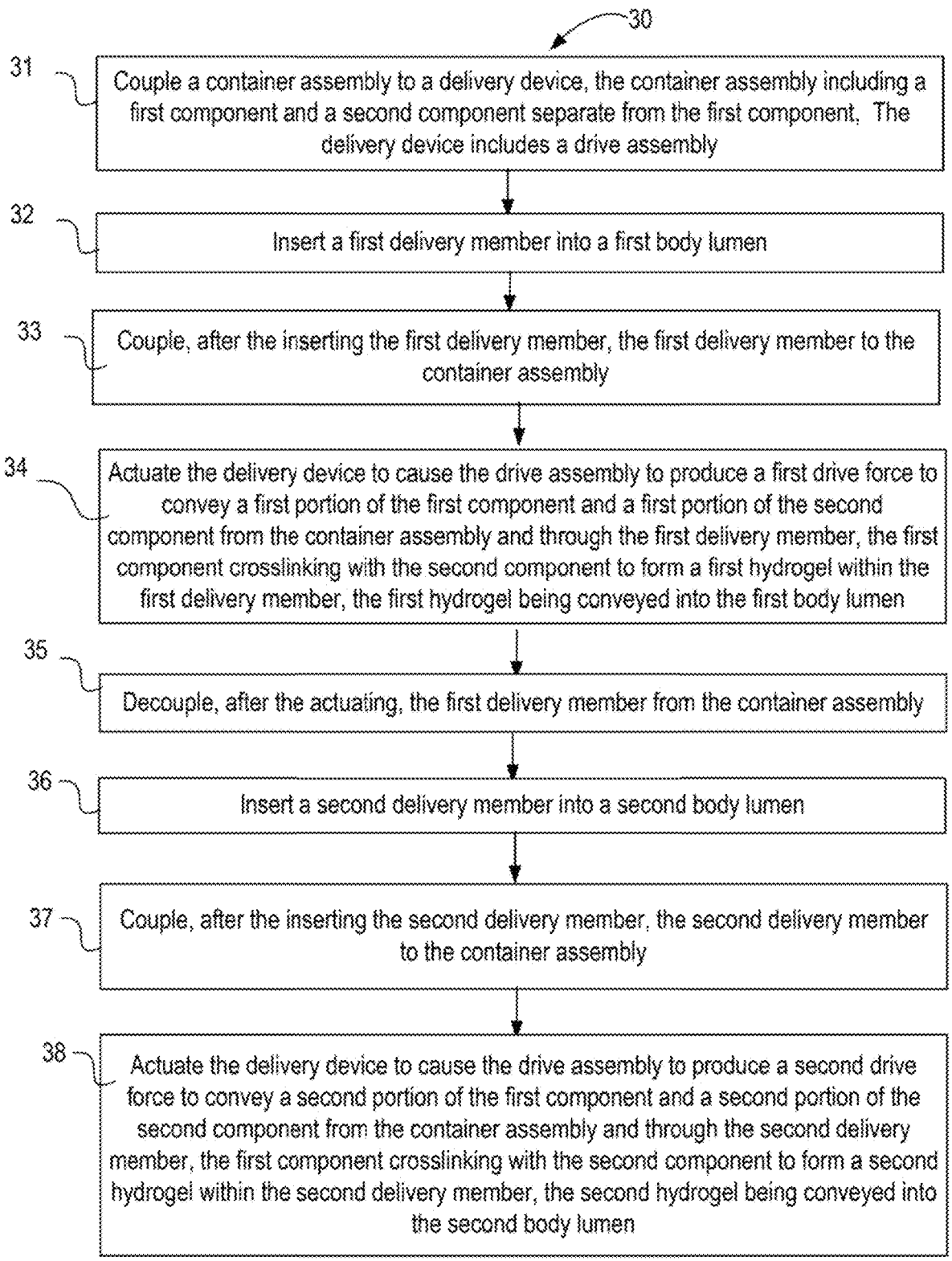
FIG. 33 is a flow chart of a method of delivering a hydrogel according to an embodiment.
Figure 34:
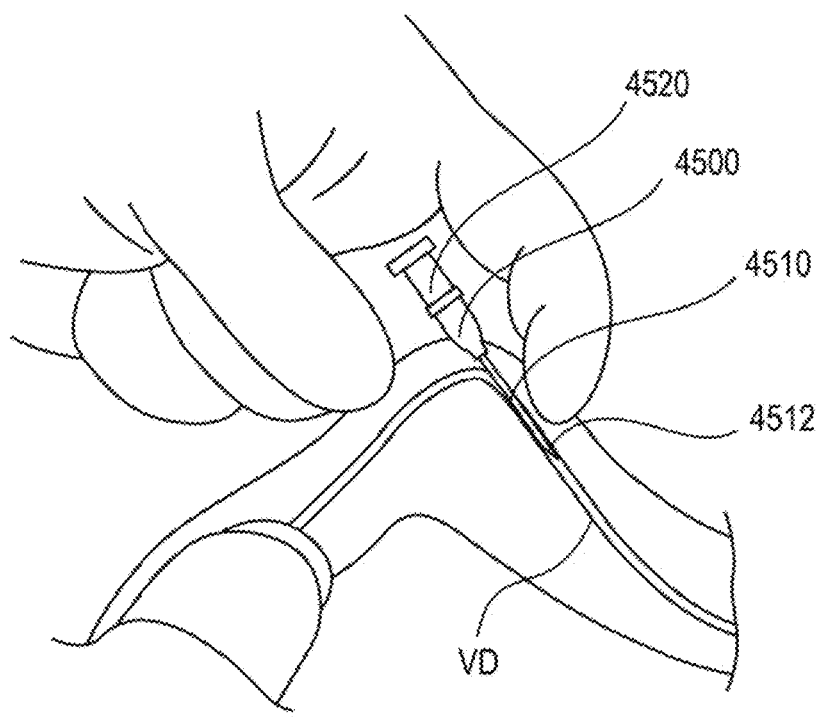
FIG. 34 is a schematic diagram showing an insertion of a delivery member into a body lumen according to an embodiment.
Figure 35:
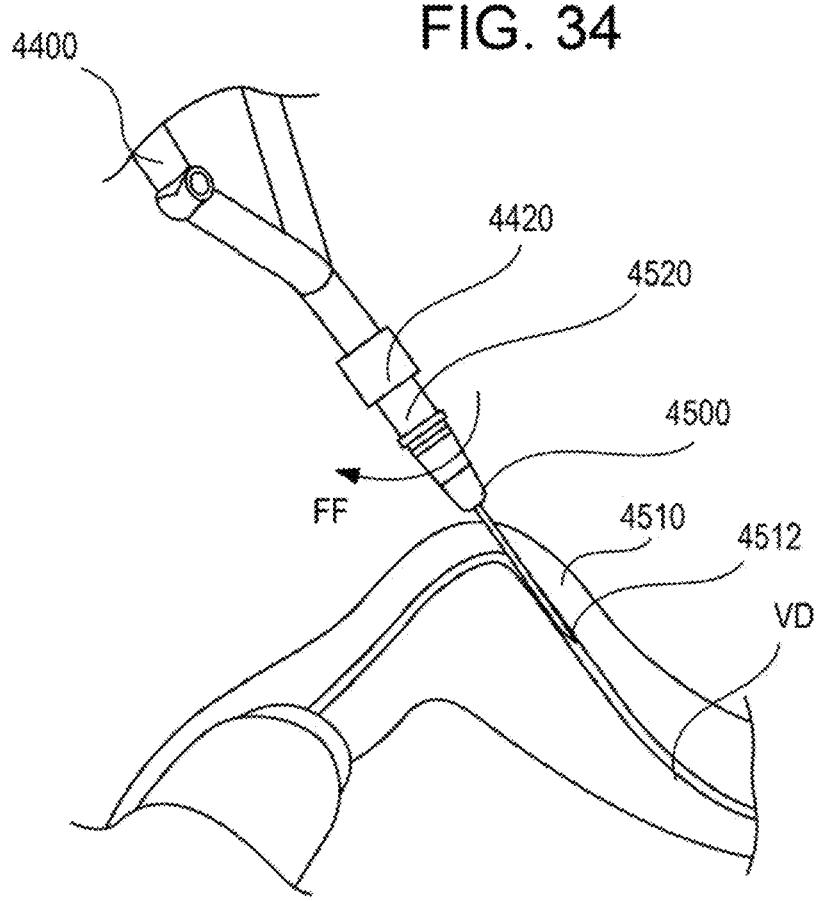
FIG. 35 is a schematic diagram showing a coupling of the delivery member in FIG. 34 to a connector attached to a container assembly according to an embodiment.
Figure 36:
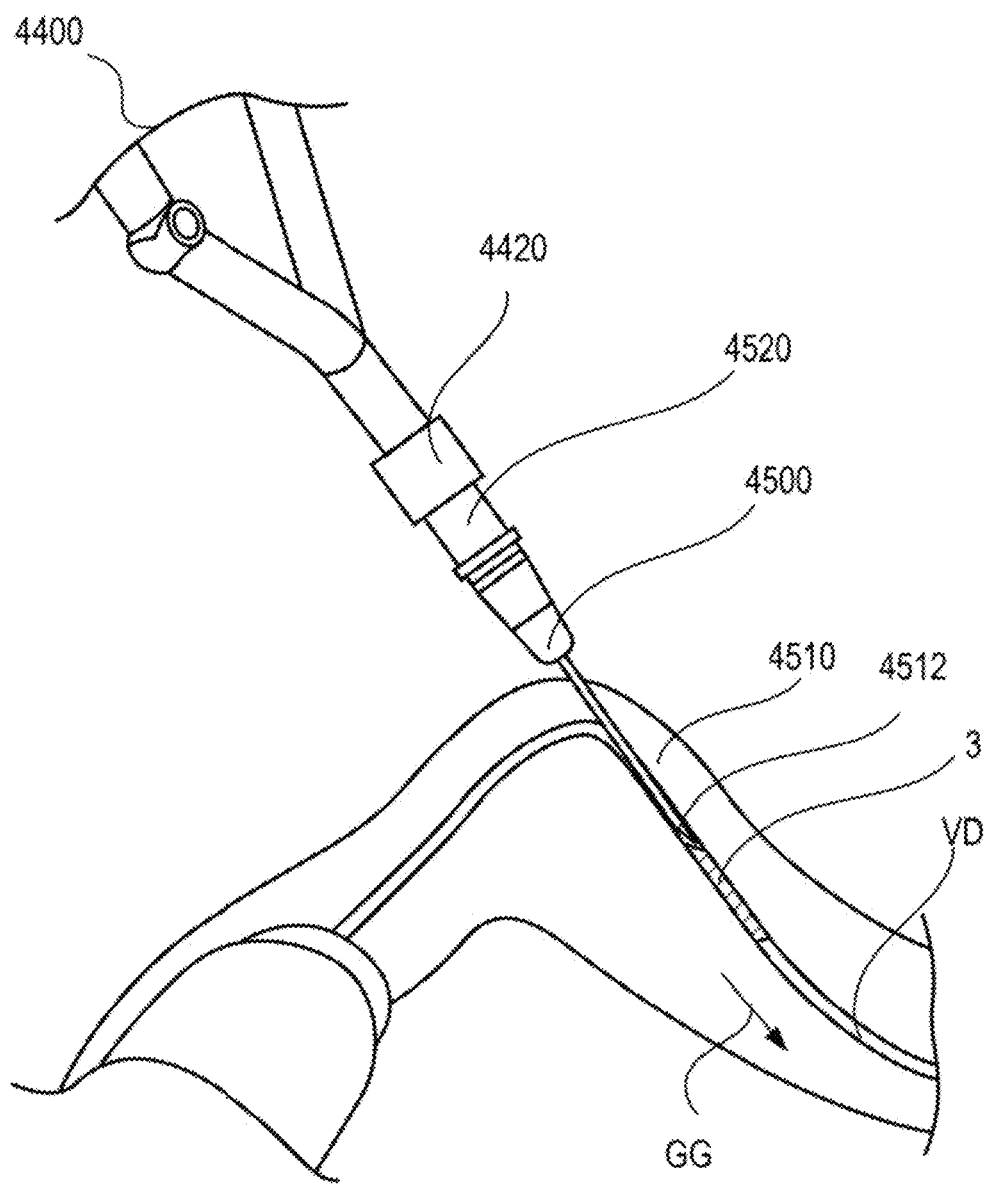
FIG. 36 is a schematic diagram showing delivery of biomaterial components to the body lumen via the connector and delivery member of FIG. 35.

FIG. 33 is a flow chart illustrating a method 30 of delivering a biomaterial product, according to an embodiment, which is described below with reference to FIGS. 34-36. Although the method 30 is described in connection with the delivery system 4000, in other embodiments the method 30 can be performed with any of the systems, delivery devices, and components described herein, such as, for example, the delivery systems 1000, 2000, and 3000 and/or the delivery devices 1100, 2100, and 3100 described herein. In some embodiments, the cartridge assembly can be prepared in advance of the delivery operation. For example, the first component can be prepared and loaded into a first container (or syringe) and the second component can be prepared and loaded into a second container (or syringe). The containers can then be optionally be placed into a cartridge (e.g., the cartridge 4350). The method includes coupling the container assembly to a delivery device, at 31. The container assembly includes a first component and a second component separate from the first component. In some embodiments, the container assembly can include a single container similar to the container assembly 2300 described above. The delivery device can be any of the delivery devices described herein and includes a drive assembly.

A first delivery member is inserted into a first body lumen, at 32. Referring to FIG. 34, the first delivery member can be the delivery member 4500 and the inserting can include inserting the end portion 4512 into a first vas deferens VD of a patient. After the first delivery member is inserted, the first delivery member coupled to the container assembly, at 33. In some embodiments, the system can be primed before the first delivery member is coupled to the container assembly, as described above. Referring to FIG. 35, the first delivery member 4500 can be coupled to the container assembly via the connector 4400. The coupling can be completed by rotating at least one of the fitting 4420 or the delivery member 4500 relative to the other.

The delivery device is actuated to cause the drive assembly to produce a first drive force to convey a first portion of the first component and a first portion of the second component from the container assembly and through the first delivery member, at 34. The first component crosslinks with the second component to form a first hydrogel within the first delivery member. The continued conveying causes the first hydrogel to be conveyed into the first body lumen. Referring to FIG. 36, the first hydrogel (identified as the biomaterial product 3) is conveyed into the vas deferens VD as shown by the arrow GG. The delivery can be controlled as described herein to produce a desired volume and/or length of the first hydrogel within the vas deferens.

After the first actuating, the first delivery member is decoupled from the container assembly, at 35. The first delivery member can optionally be removed and discarded. A second delivery member is inserted into a second body lumen, at 36. The second delivery member can be the delivery member 4500 and the inserting can include inserting the end portion 4512 into a first vas deferens VD of a patient. After the second delivery member is inserted, the second delivery member coupled to the container assembly, at 37.

The delivery device is actuated at second time to cause the drive assembly to produce a second drive force to convey a second portion of the first component and a second portion of the second component from the container assembly and through the second delivery member, at 38. The first component crosslinks with the second component to form a second hydrogel within the second delivery member. The continued conveying causes the second hydrogel to be conveyed into the second body lumen.

Although in many instances it can be undesirable to deliver any substance other than the therapeutic material into the body, the systems described herein can be used to advantageously prime (or prepare) a vessel within which the biomaterial product is to be delivered. Similarly stated, in some embodiments, a method can include delivering a priming fluid (e.g., air, saline, or any other suitable inert fluid) into the target vessel before delivering the biomaterial product. Delivery of a priming fluid can prepare the body lumen by dilating (or enlarging) the body lumen, washing away impurities, and/or by producing a coating on the walls that can improve the efficacy of the delivered biomaterial product and aid in proper placement of the biomaterial product.

Figure 37:
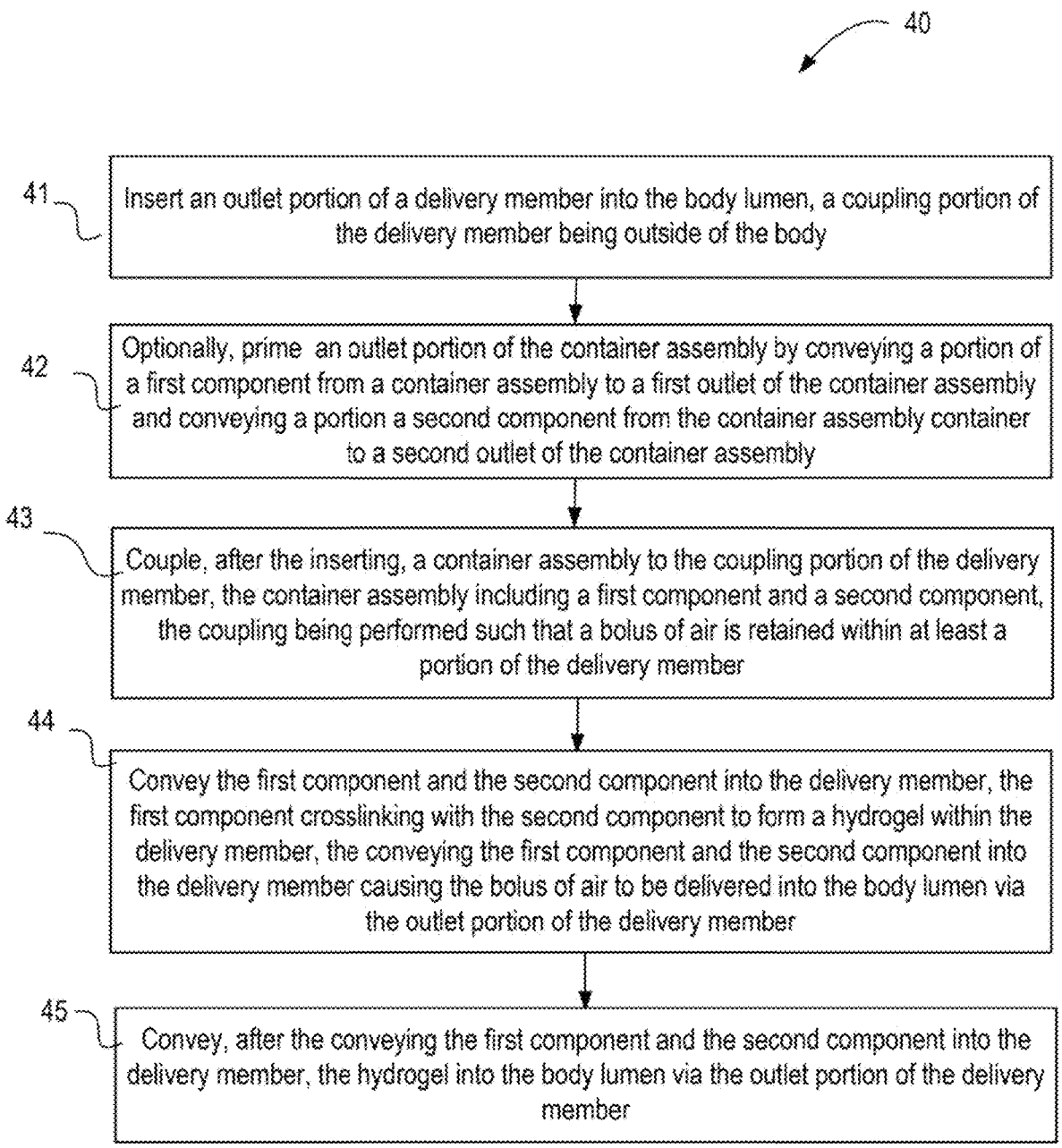
FIG. 37 is a flow chart of a method of delivering a hydrogel into a body lumen according to an embodiment.
Figure 38:
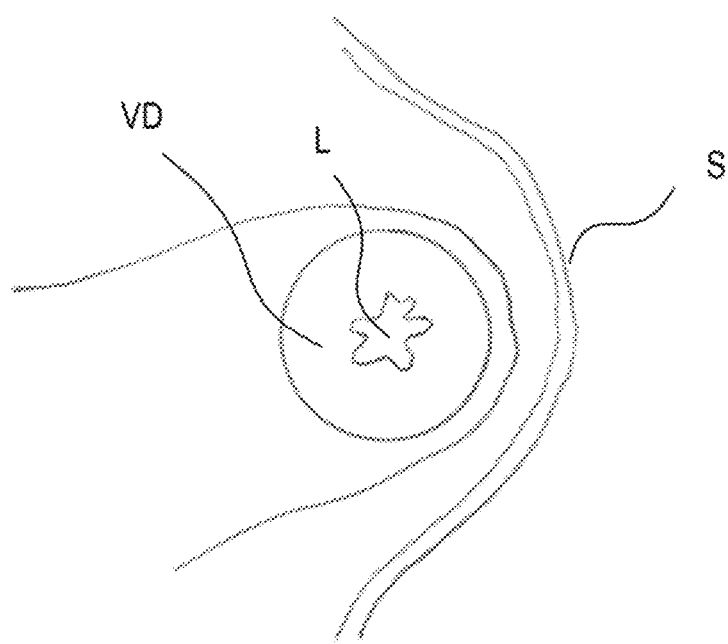
FIGS. 38 and 39 are partial cross-sectional views of a vas deferens and an interior body lumen thereof in various stages during the method shown in FIG. 37.
Figure 39:
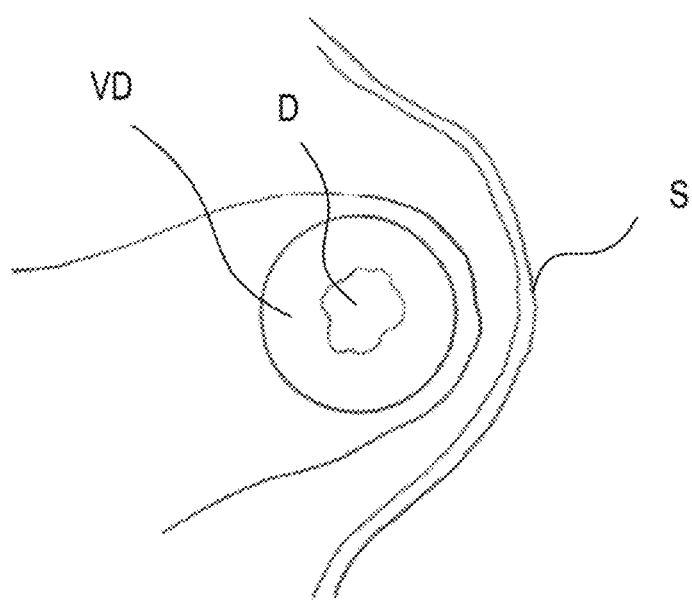

FIG. 37 is a flow chart illustrating a method 40 of delivering a biomaterial product, according to an embodiment, which is described below with reference to FIGS. 38 and 39. The method 40 can be performed with any of the systems, delivery devices, and components described herein, such as, for example, the delivery systems 1000, 2000, 3000, and 4000 and/or the delivery devices 1100, 2100, 3100, and 4100 described herein. In some embodiments, the cartridge assembly can be prepared in advance of the delivery operation. For example, the first component can be prepared and loaded into a first container (or syringe) and the second component can be prepared and loaded into a second container (or syringe). The containers can then be optionally be placed into a cartridge (e.g., the cartridge 4350). The method includes inserting an outlet portion of a delivery member into the body lumen, at 41. The delivery member can be any of the delivery members described herein (e.g., the delivery member 4500) and the outlet portion can be inserted into any body lumen, such as a vas deferens VD of a patient. The delivery member is inserted such that a coupling portion (e.g., similar to the hub 4520) is outside of the body.

In some embodiments, the system can optionally be primed before the first delivery member is coupled to the container assembly, at 42. The system priming (not to be confused with the priming of the vessel) can be performed by any of the methods described above. For example, in some embodiments, the system priming can include priming an outlet portion of the container assembly by conveying a portion of the first component from the container assembly to a first outlet of the container assembly and conveying a portion of the second component from the container assembly to a second outlet of the container assembly.

After the delivery member is inserted, the coupling portion of the delivery member is coupled to the container assembly, at 43. The coupling is performed such that a bolus of air is retained within at least a portion of the delivery member. In other embodiments, however, a bolus of any fluid can be used to prime the vessel. For example, in some embodiments, a predetermined amount of a saline solution can be placed into the delivery member (e.g., the mixing volume 4521) before the delivery member is coupled to the container assembly.

The method then includes conveying the first component and the second component into the delivery member, at 44. The first component crosslinks with the second component to form a hydrogel within the delivery member. The conveying the first component and the second component into the delivery member also causes the bolus of air to be delivered into the body lumen via the outlet portion of the delivery member. For example, FIGS. 38 and 39 show cross-sectional views of portion of a vas deferens VD in which the biomaterial product is to be implanted. FIG. 38 shows the cross-sectional shape of the lumen L before the bolus of air (or priming fluid) is delivered. As shown, the cross-sectional shape is irregular and includes many sharp bends (i.e., areas of small radius of curvature). FIG. 39 shows the cross-sectional shape of the lumen L after the bolus of air (or priming fluid) has been delivered. As shown, delivery of priming fluid expands the lumen L and reduces the irregularity and sharp bends in the lumen L. In this manner, the priming of the vessel produces a section of the vessel that will produce better adherence and/or retention of the delivered biomaterial. After the initial conveying of the first component and the second component into the delivery member, the hydrogel is conveyed into the body lumen via the outlet portion of the delivery member, at 45.

Figure 40:
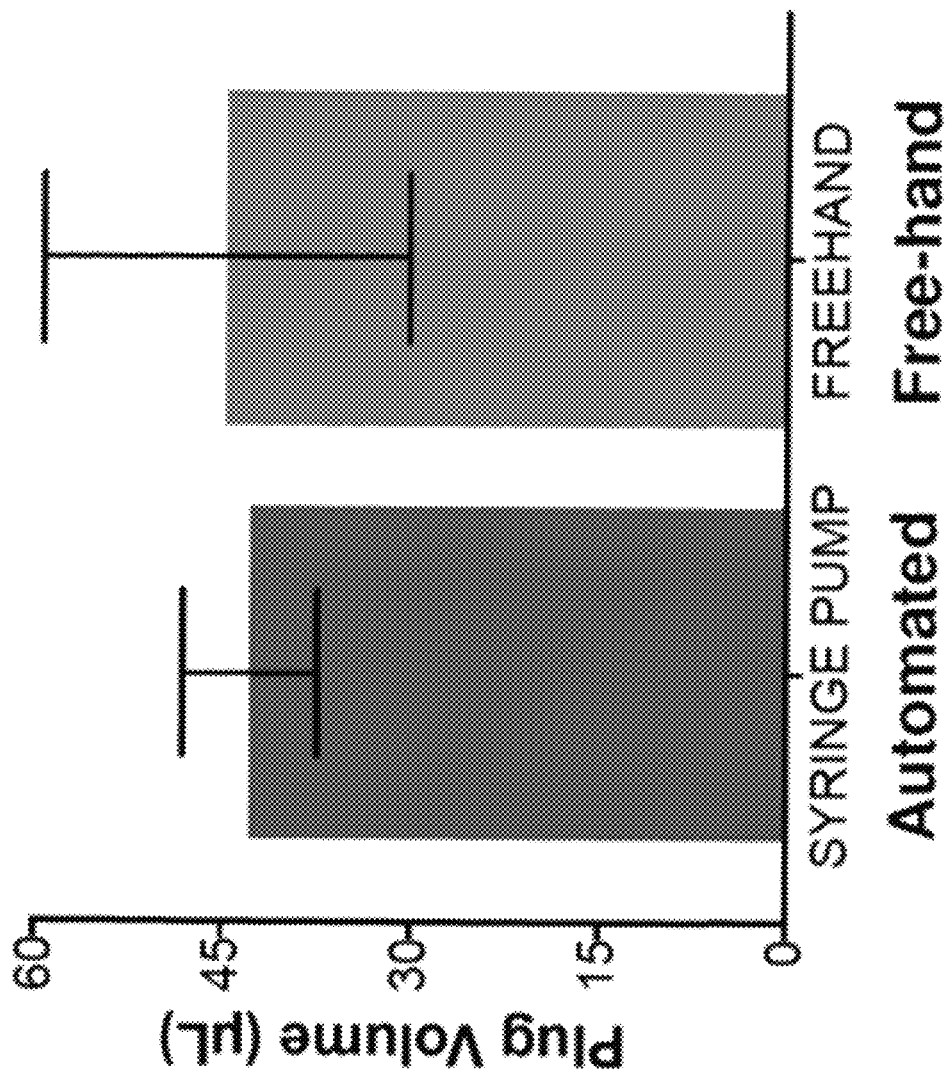
FIG. 40 is a graph showing the accuracy and precision of plug volume extruded from an automated delivery apparatus, according to an embodiment, versus that produced by a free-hand delivery apparatus.

FIG. 40 is a bar graph demonstrating the accuracy and precision of using an automated injection device, as described in embodiments in this invention, versus a free-hand injection device, which requires the user to press on a thumb clip to inject. Both the automated and free-hand devices have similar components including syringes, plungers, Y-connector, delivery member (e.g., angiocatheter), and polymer materials. Testing of the free-hand injections into synthetic model tubing across six users (n=207) demonstrated high accuracy of plug volume; however, the precision was low and users experienced clogging of the device 5% of the time. The automated device, on the other hand, had high accuracy and precision for all implantations (n=28) and there were zero clogs reported. This highlights the improvements provided by the automated devices described herein, which can allow users (i.e. physicians) to reliably implant biomaterials even amongst the patient-to-patient variability. Specifically by controlling delivery of the implanted material by a device and not by forces generated by the user's hands, the performance of the delivery is improved. The volume displayed does not include the dead volume of the needle or catheter, rather only the volume that exited the tip of the catheter or needle.

Figure 41:
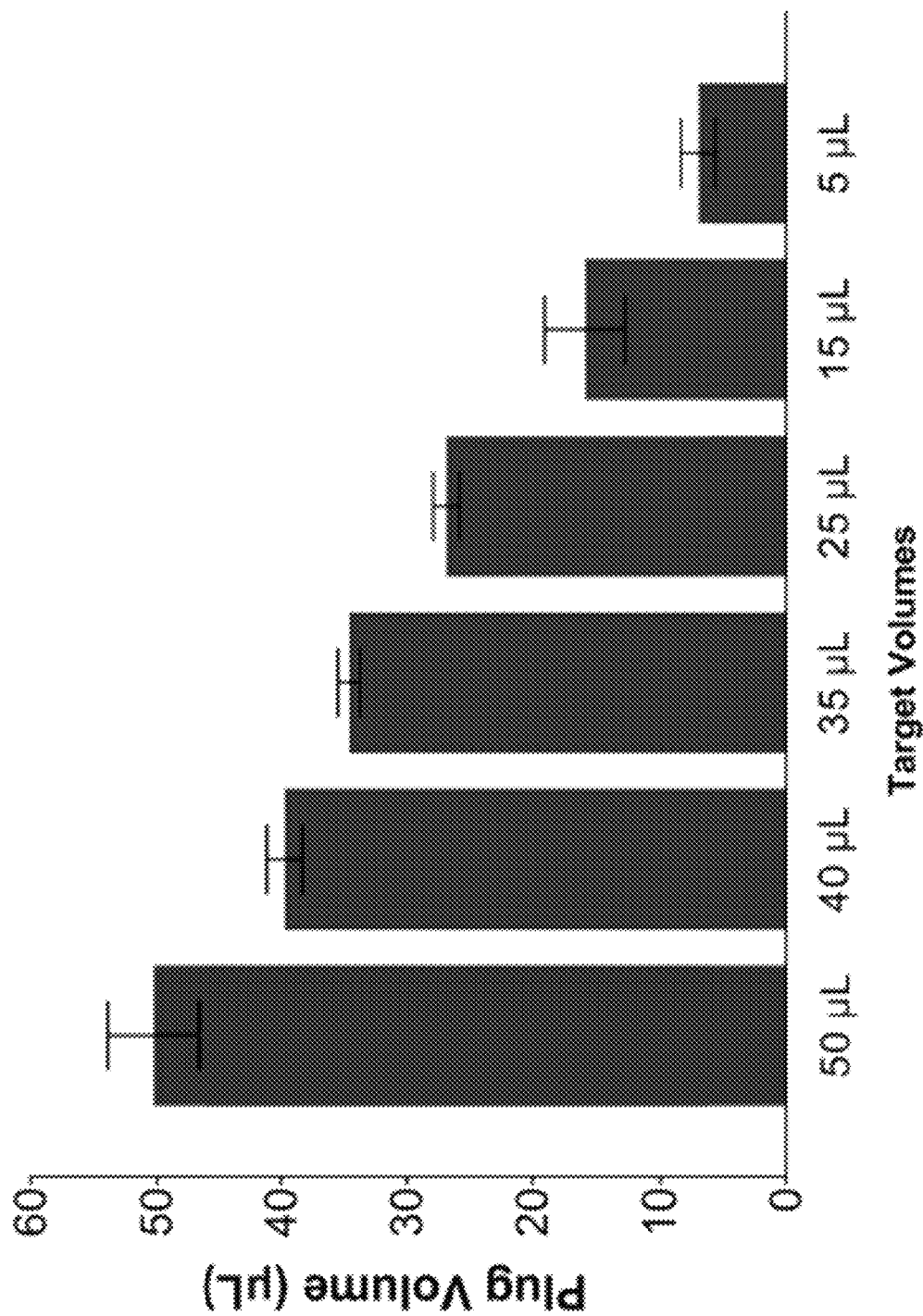
FIG. 41 is a graph showing the target and resulting plug volume using a delivery apparatus according to an embodiment, such as an automated delivery apparatus.

FIG. 41 is a bar graph demonstrating the use and precision of an embodiment described herein. The automated device was able to deliver two-component polymer hydrogels (n=10) with implant volumes that precisely corresponded to the target delivery volumes. No clogs were observed for any group. The volume displayed does not include the dead volume of the needle or catheter, rather only the volume that exited the tip of the catheter or needle.

Figure 42:
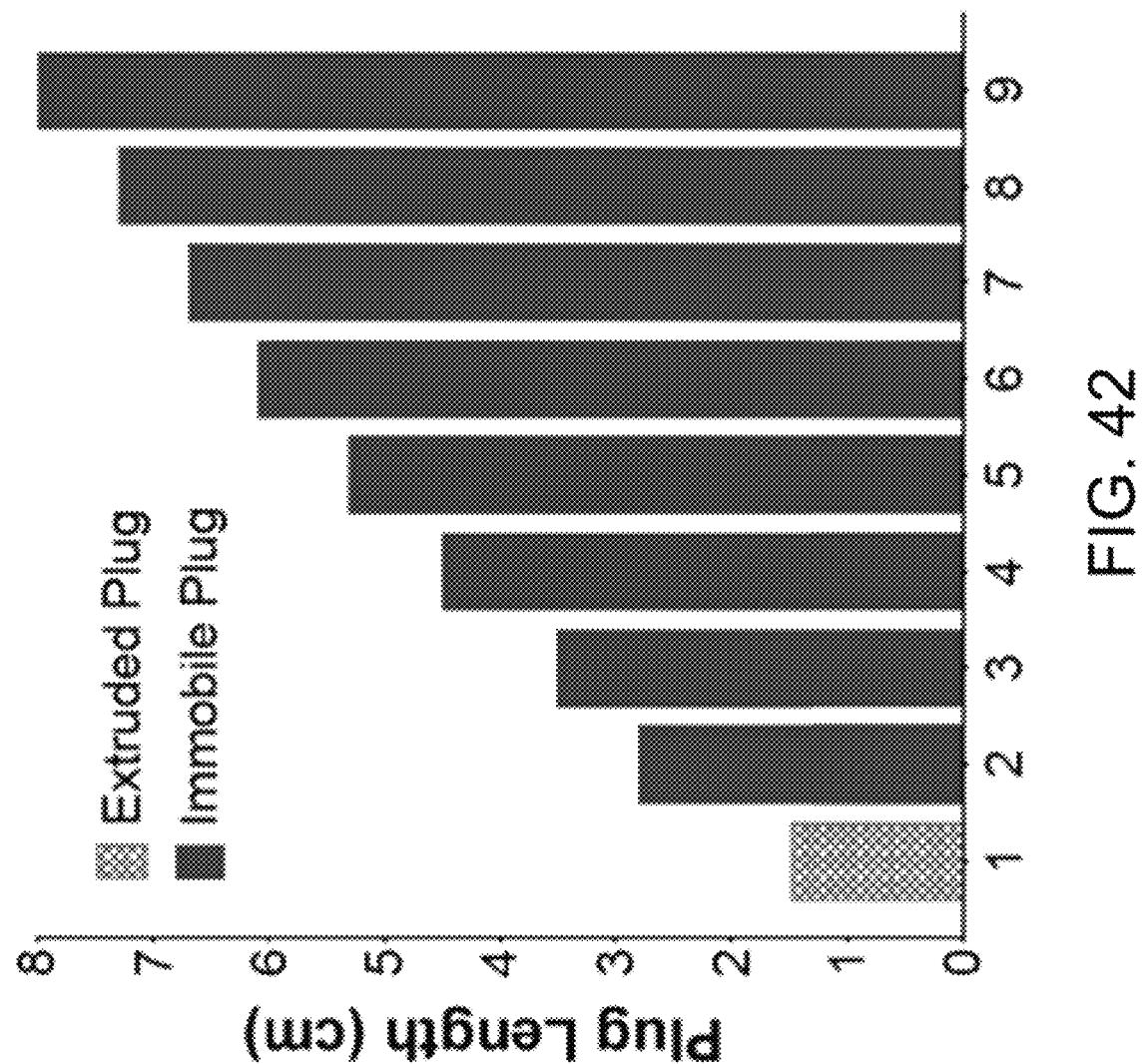
FIG. 42 is a graph showing extruded and immobile plug lengths formed using a delivery apparatus according to an embodiment, such as an automated delivery apparatus.
Figure 43:
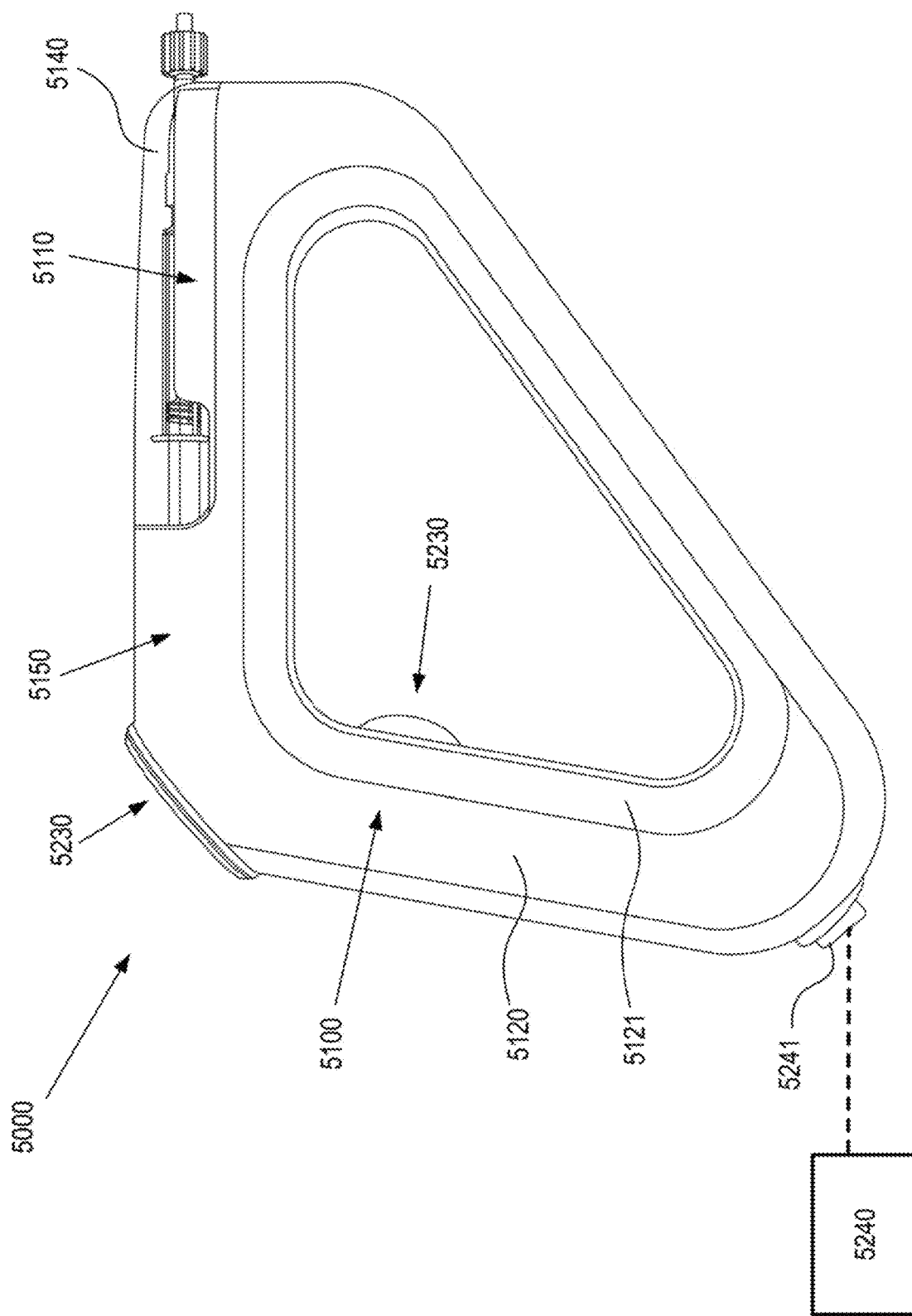
FIG. 43 is a side view of a delivery system according to an embodiment.
Figure 44:
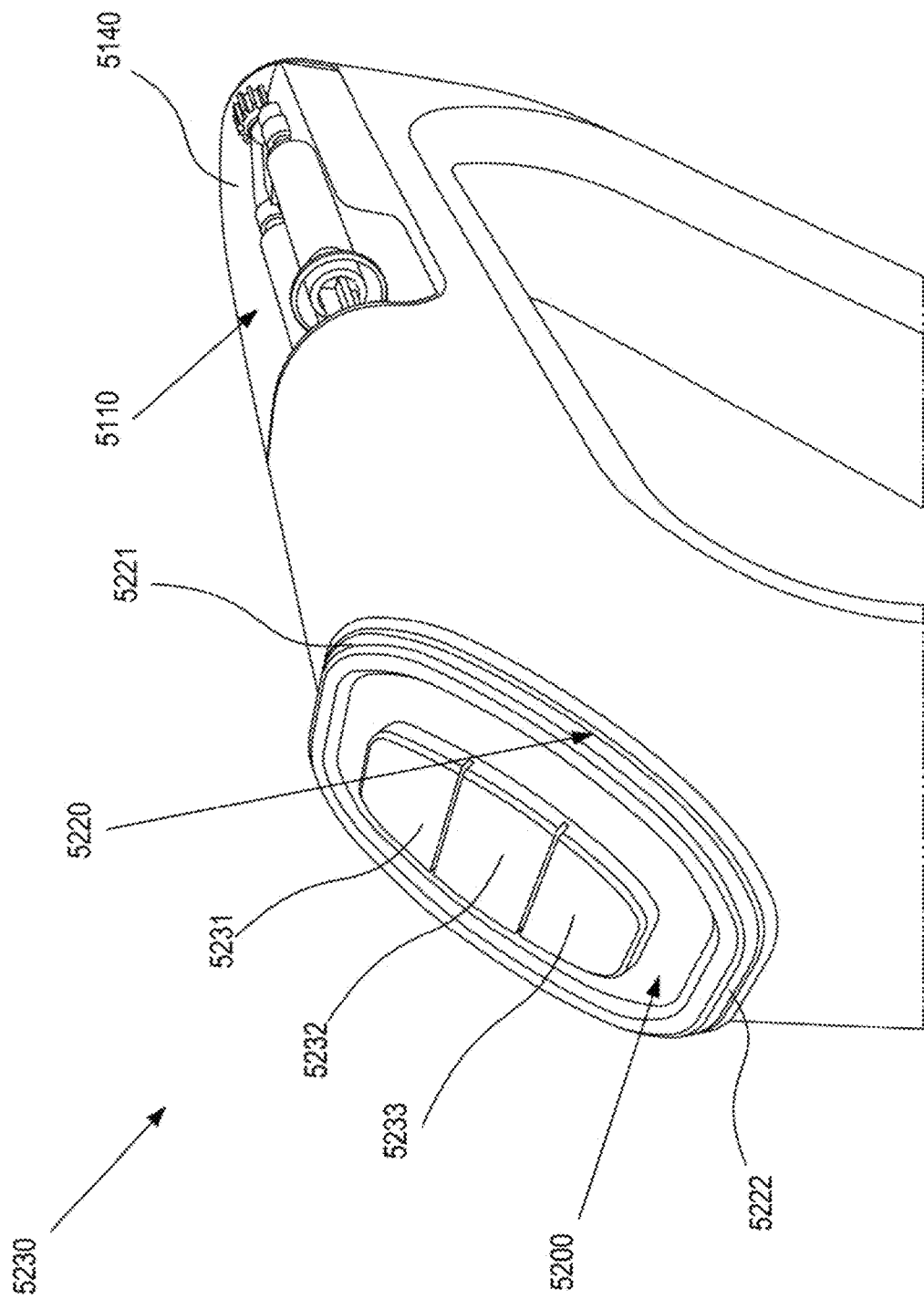
FIG. 44 is a rear perspective view of the delivery system of FIG. 43 illustrating user operated buttons.

FIG. 42 is a bar graph demonstrating the use of an embodiment of an automated device to form different implant lengths (also known as plug lengths) into synthetic tubing (0.8 mm in inner diameter). Plug lengths ranged from 1.5 cm to 8 cm depending on the injection volume. Following implantation, the plugs were subjected to burst-pressure testing of saline at 10 lbF (120× in vivo pressures). The graph depicts that plugs of 1.5 cm in length were not able to withstand burst-pressure testing, while plugs greater than 2 cm were able to withstand the burst pressure. This data underscores the importance of controlling the velocity, flow rate and/or drive force to ensure a desired volume and/or length of the delivered biomaterial is achieved.

FIGS. 43-47 show a delivery system 5000 according to an embodiment. As described herein, the delivery system 5000 is configured to convey and combine multiple biomaterial components to form a biomaterial product that is delivered to a target location.

The system 5000 includes a delivery device 5100, a drive assembly 5150, an electronic control system 5200, a container assembly 5300, and a connector 5400. The delivery device 5100 includes a housing 5110, a drive assembly 5150, and a handle portion 5120. The handle portion 5120 can include a textured or perforated surface 5121 to improve grip. Similar to other container assemblies described above, the container assembly 5300 includes a first container 5301 and a second container 5302. The container assembly 5300 further includes a first end 5331 configured to couple to the connector 5400, and a second end 5332 that includes a flange portion 5343 configured to receive an input force from the drive assembly 5150. The drive system 5150 is configured to drive the flange portion 5343, which in turn actuates the plungers 5340 to expel a first component from the first container 5301 and a second component from the second container 5302. As the first and second components are expelled from the first container 5301 and the second container 5302, respectively, the first and second components are conveyed to the connector 5400. The components can be mixed, crosslinked, and dispensed from the connector 5400 in the same manner as other connectors described above.

The electronic control system 5200 is configured to control the actuation and output of the drive assembly 5150 and is operable to control delivery characteristics of the delivery device 5100 in the same manner as other delivery devices and methods described above. The electronic control system 5200 includes one or more buttons 5230. In some embodiments, the one or more buttons 5230 include a first button 5231, a second button 5232, a third button 5233, and a fourth button 5234. The first, second, and third buttons 5231, 5232, 5233 are positioned above the handle portion 5120 and permit a user to access the first, second, and third buttons 5231, 5232, 5233 via their thumb while gripping the handle portion 5120. The fourth button 5234 is positioned behind the handle portion 5120 and permits a user to access the fourth button 5234 via their index finger while gripping the handle portion 5120, for example. The electronic control system 5200 further includes an indicator 5220 to provide visual feedback to a user. For example, the indicator 5220 may include one or more lights 5221, 5222. The lights 5221, 5222 may illuminate to display different colors of light and/or different solid or flashing patterns to provide visual feedback or operating status of the delivery device 5100 to a user. In some embodiments, the indicator 5220 may further include a display (not shown) to show text, numbers, or symbols to provide additional visual feedback to a user.

The first button 5231 is configured as a power button to turn on and off the delivery device 5100. The second button 5232 is configured as a prime button for performing a priming operation (e.g., actuating the drive assembly 5150 to convey the first component and the second component into the connector 5400). For example, the delivery device 5100 is operable to perform any of the priming operations described herein. The third button 5233 is configured as an injection button for performing an injection operation (e.g., mixing the two components to form a biomaterial and dispensing the biomaterial from the connector and into a body lumen). For example, the delivery device 5100 is operable to perform any of the injection or controlled delivery operations described herein. The fourth button 5234 is configured as a trigger button. For example, depressing either the second button 5232 or the third button 5233 may initiate the delivery device 5100 for the priming operation or the injection operation, respectively. The delivery device 5100 may confirm the selected operation by blinking one or more of the lights 5221, 5222, and/or illuminating a green color, for example. To confirm and proceed with the selected operation, a user depresses the fourth button 5234. After the fourth button 5234 is depressed, the delivery device 5100 executes the selected operation.

In some embodiments, the electronic control system 5200 is coupled to a power source 5240 via a charge port or connector 5241 to supply electrical power to the delivery device 5100. The delivery device 5100 may be fully powered by the power source 5240, partially powered by the power source 5240, and/or recharged via the power source 5240. Digital and analog signals may also be transmitted to and from the delivery device 5100 via the connector 5241.

Figure 45:
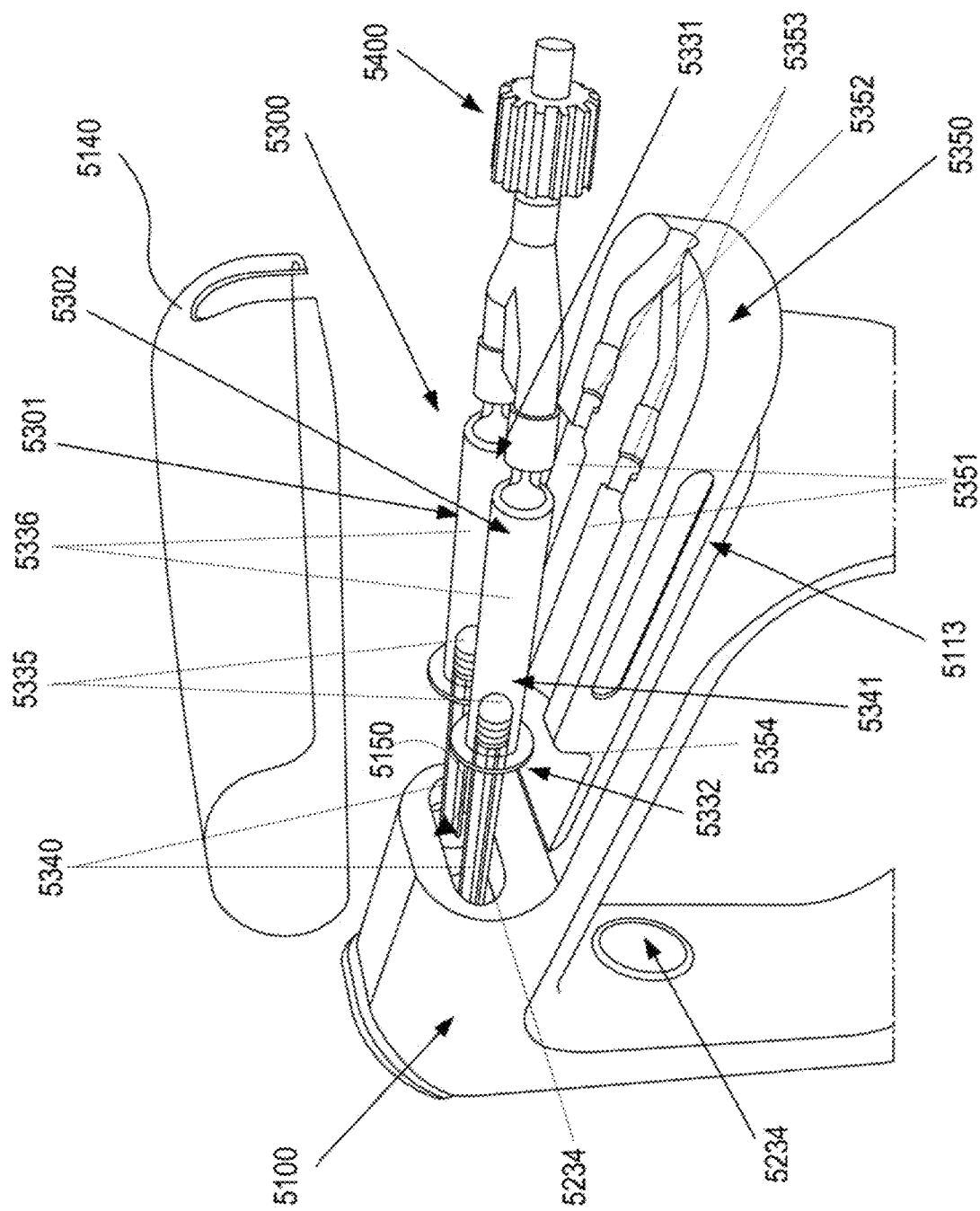
FIG. 45 is a front perspective view of the delivery system of FIG. 43 illustrating a cover in an open position.
Figure 46:
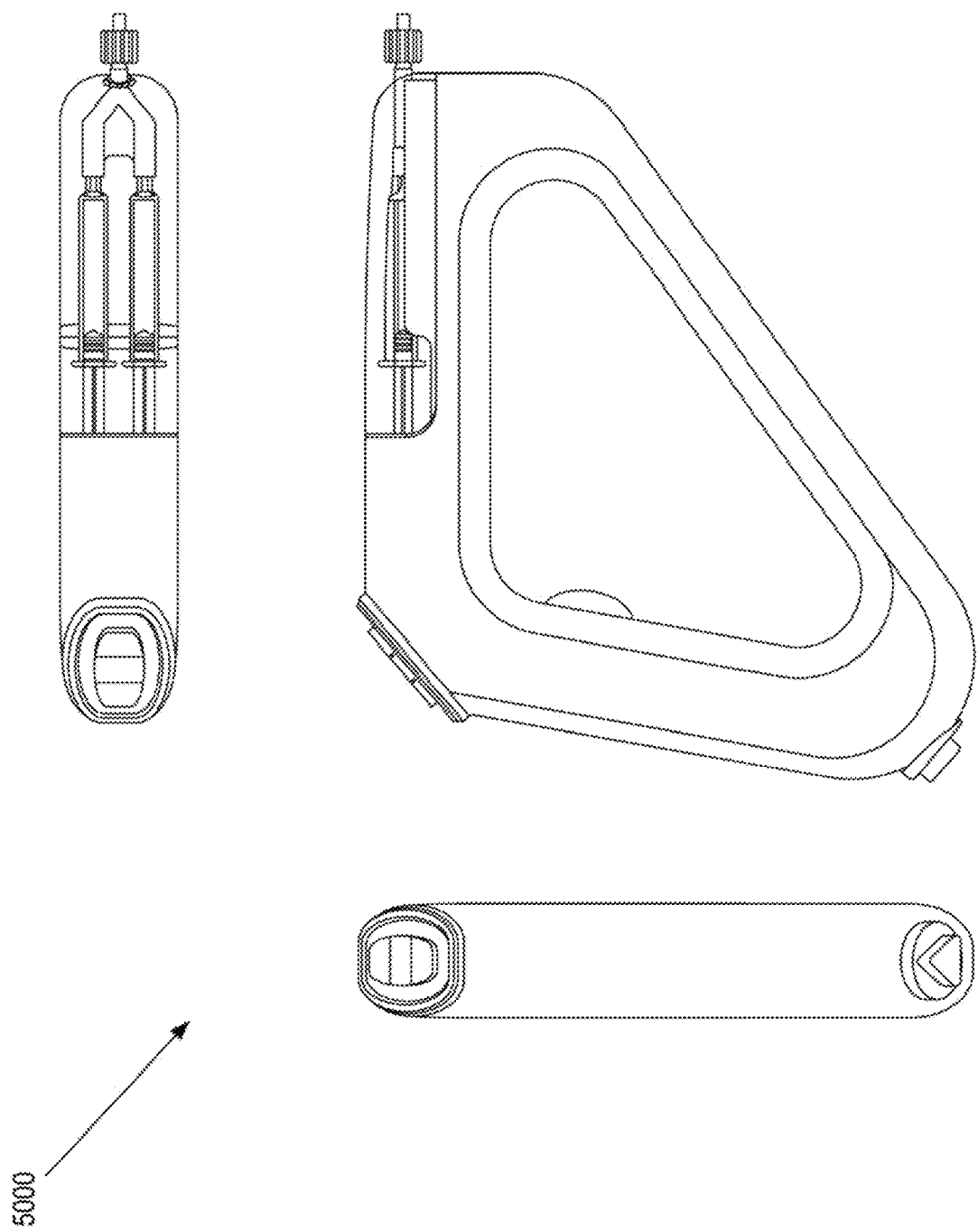
FIG. 46 is an orthographic view of the delivery system of FIG. 43.
Figure 47:
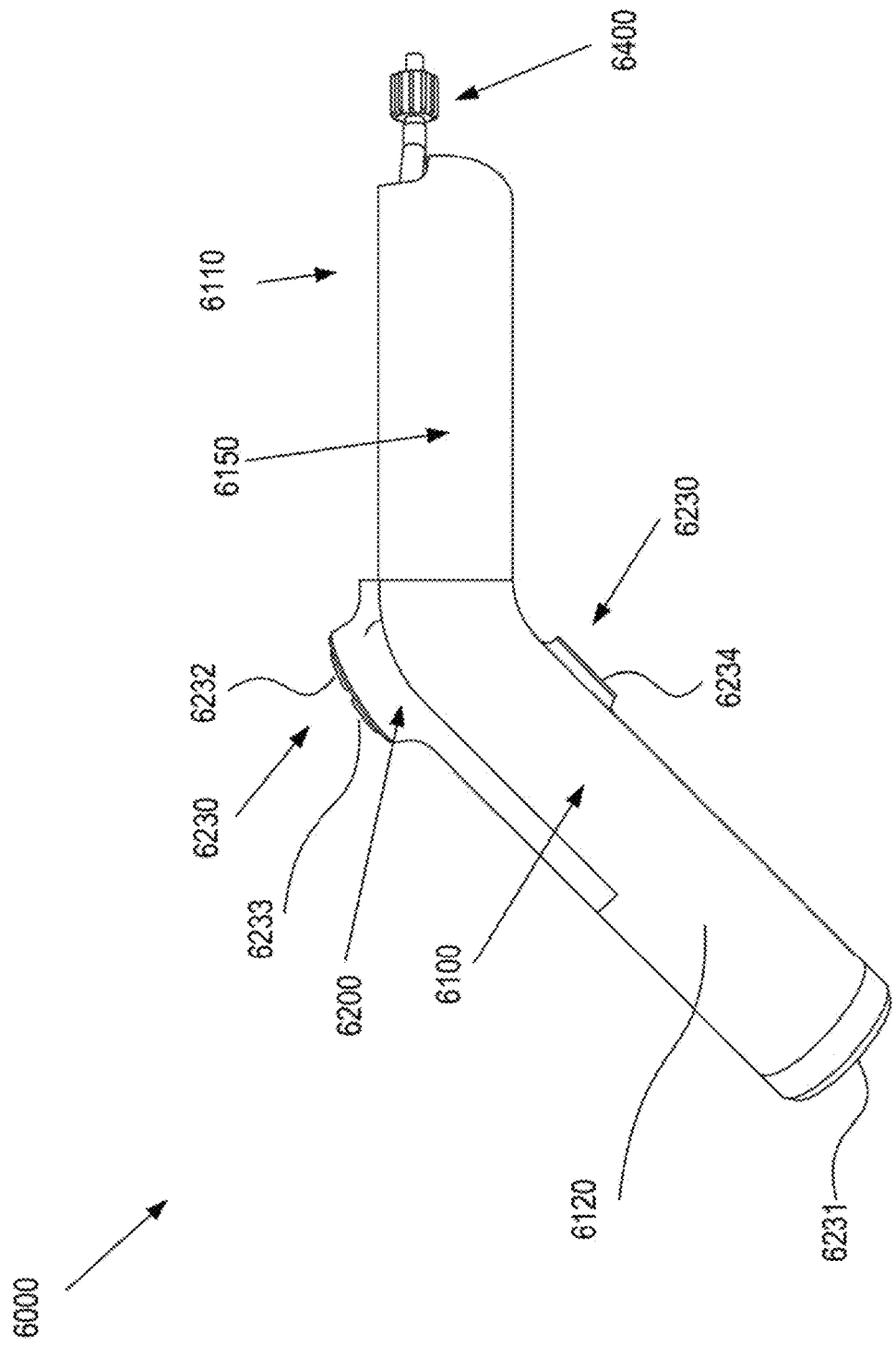
FIG. 47 is a side view of a delivery system according to an embodiment.
Figure 48:
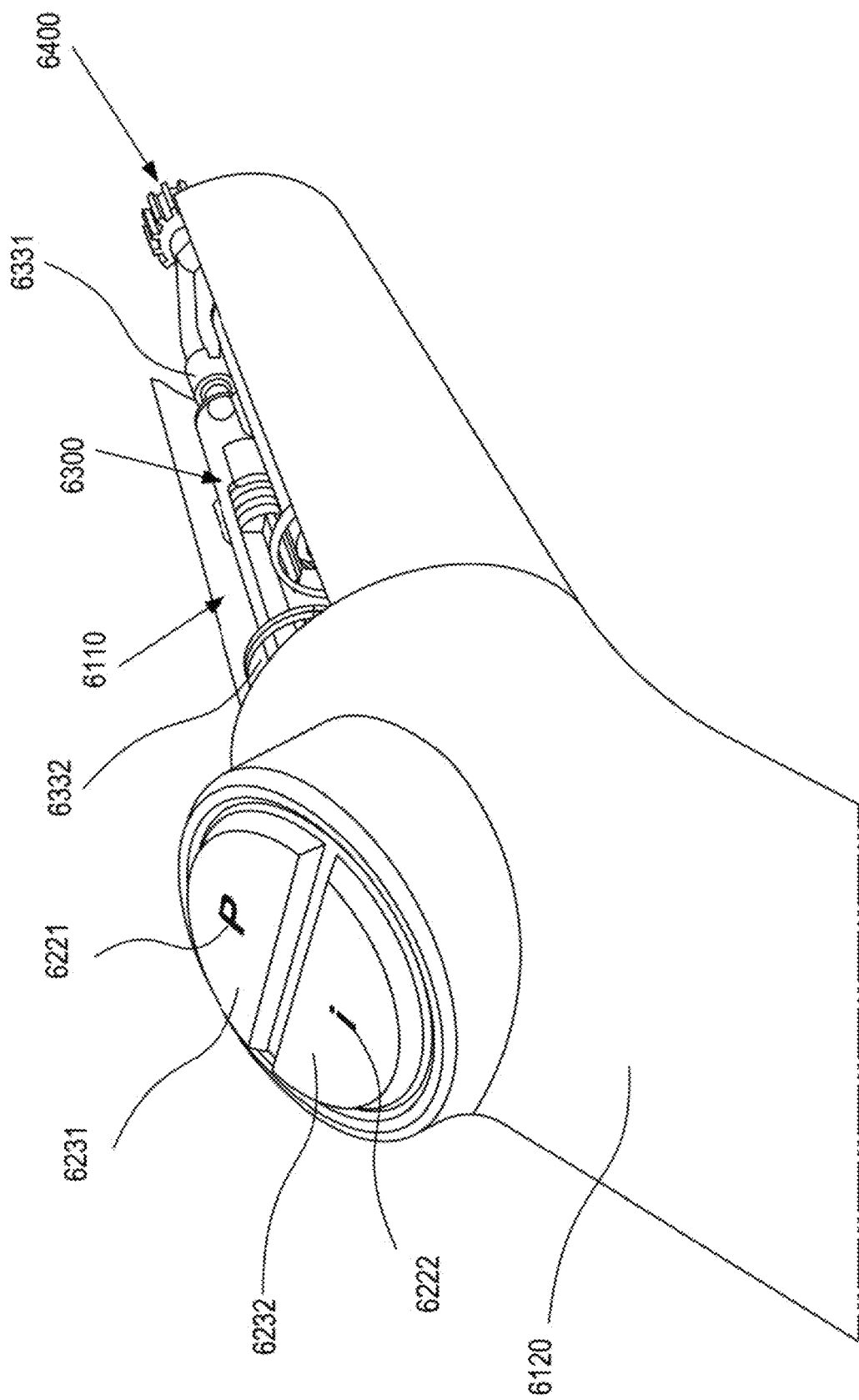
FIG. 48 is a rear perspective view of the delivery system of FIG. 47 illustrating user operated buttons.

As shown generally in FIG. 45, the housing 5110 includes a movable lid 5140 to surround and/or secure the container assembly 5300 to the housing 5110. The movable lid 5140 can be opened by a hinge mechanism, sliding the cover, and/or removed from the delivery device 5100 in order to access, install, and/or remove the container assembly 5300 from an internal area of the housing 5110. When the movable lid 5140 is lifted off of the delivery device 5100 in an open position, the container assembly 5300 is accessible. In the open position, an internal area of the housing 5110 is exposed for the container assembly 5300 to be inserted into, mounted onto or removed from the housing 5110 of the delivery device 5100. For example, a new container assembly may be installed into the housing 5110 prior to a new procedure and removed from the housing 5110 once the procedure has been completed. In some embodiments, the container assembly 5300 is a consumable component and the delivery device 5100 is a reusable component.

The movable lid 5140 and the delivery device 5100 may include hinges or complementary mounting tabs (not shown) to removably secure the movable lid 5140 to the delivery device 5100 in a closed position. Additionally, or alternatively, the movable lid 5140 and the delivery device 5100 may include complementary tracks, detents, and/or magnetic features (not shown) to removably secure the movable lid 5140 in a closed position.

As shown in FIG. 45, the container assembly 5300 includes a cartridge 5350. The cartridge 5350 includes a first recessed portion 5351 for receiving the first container 5301 and the second container 5302 of the container assembly 5300. The cartridge 5350 further includes a second recessed portion 5352 for receiving and securing the connector 5400 to the cartridge 5350. The cartridge 5350 includes one or more ribs 5353 or bumpers 5354 to prevent the first and second containers 5301, 5302 and the connector 5400 from moving in an axial direction when installed onto the cartridge 5350. The first recessed portion 5351 and the second recessed portion 5352 can be dimensioned and shaped to provide a frictional fit to prevent the container assembly 5300 and the connector 5400 from moving in a lateral direction.

On a side opposite of the first recessed portion 5351 and/or the second recessed portion 5352 (e.g., bottom side of the cartridge 5350 in FIG. 45), the cartridge 5350 includes a mounting portion to secure and align the cartridge 5350 to the housing 5110 of the delivery device 5100. In some embodiments, a kit including the cartridge 5350 with the container assembly 5300 and the connector 5400 is preinstalled and assembled onto the cartridge 5350 such that a user can install the cartridge 5350 directly onto the housing 5110 for ease of use and efficiency. Additionally, because the locations of the container assembly 5300 relative to the cartridge 5350 is known, and the cartridge 5350 is coupled to the housing 5110 at a predefined location on the housing 5110, along an axis of travel of the plungers 5340, separate alignment and calibration steps are not required. Furthermore, alignment of the cartridge 5350 on the housing 5110 via the mounting portion enables the drive assembly 5150 to engage the plungers 5340 at a predetermined home position inadvertently actuating the plungers 5340. As such, the mounting portion automatically aligns and predictably orients the container assembly 5300 onto the housing 5110 such that the drive assembly 5150 engages the plungers 5340 consistently at a predetermined home position without inadvertently actuating the plungers 5340. For example, the drive assembly 5150 may be placed in a retracted position (e.g., a home position described herein) such that the cartridge 5350 and container assembly 5300 do not engage the drive assembly 5150 during installation onto the housing 5110. This prevents the plungers 5340 from actuating inadvertently. Once the cartridge 5350 and container assembly 5300 have been installed on the housing 5110, the drive assembly 5150 can perform the priming operation and/or injection operation using known locations based on the home position, described herein, thereby eliminating the need for a separate alignment or calibration procedure.

In some embodiments, the cartridge 5350 and the container assembly 5300 are provided as consumable components that can be quickly installed into and aligned with the housing 5110 of the delivery device 5100.

FIGS. 47-52 show a delivery system 6000 according to an embodiment. As described herein, the delivery system 6000 is configured to convey and combine multiple biomaterial components to form a biomaterial product that is delivered to a target location.

The system 6000 includes a delivery device 6100, a drive assembly 6150, an electronic control system 6200, a container assembly 6300, and a connector 6400. The delivery device 6100 includes a housing 6110, a drive assembly 6150, and a handle portion 6120. Similar to the other container assemblies described above, the container assembly 6300 includes a first container 6301 and a second container 6302. The container assembly 6300 further includes a first end 6331 configured to couple to the connector 6400, and a second end 6332 that includes a flange portion 6343 configured to receive an input force from the drive assembly 5150. The drive system 6150 is configured to drive the flange portion 6343, which in turn actuates the plungers 6340 to expel a first component from the first container 6301 and a second component from the second container 6302. As the first and second components are expelled from the first container 6301 and the second container 6302, respectively, the first and second components are conveyed to the connector 6400. The components can be mixed, crosslinked, and dispensed from the connector 6400 in the same manner as other connectors described above.

The electronic control system 6200 is configured to control the actuation and output of the drive assembly 6150 and is operable to control delivery characteristics of the delivery device 6100 in the same manner as the other delivery devices and methods described above. The electronic control system 6200 includes one or more buttons 6230. The first button 6231 is positioned at a base of the handle portion 6120. The second and third buttons 6232, 6233 are positioned above the handle portion 6120 and permits a user to access the second and third buttons 6232, 6233 via their thumb while gripping the handle portion 6120. The fourth button 6234 is positioned behind the handle portion 6120 and permits a user to access the fourth button 6234 via their index finger while gripping the handle portion 6120, for example. The electronic control system 6200 further includes a first indicator 6221 and a second indicator 6222 to provide visual feedback to a user. For example, the first indicator 6221 and the second indicator 6222 may include a backlight to illuminate a symbol or logo associated with the second button 6232 and the third button 6233, respectively.

The first button 6231 is configured as a power button to turn on and off the delivery device 6100. The second button 6232 is configured as a prime button for performing a priming operation (e.g., actuating the drive assembly 6150 to convey the first component and the second component into the connector 6400). The delivery device 6100 is operable to perform any of the priming operations described herein. The third button 6233 is configured as an injection button for initiating an injection operation (e.g., mixing the two components to form a biomaterial and dispensing the biomaterial into a body lumen). The delivery device 6100 is operable to perform any of the injection or controlled delivery operations described herein. The fourth button 6234 can be programmed or assigned as a trigger button. For example, depressing either the second button 6232 or the third button 6233 may prepare the delivery device 6100 for the priming operation or the injection operation, respectively. The delivery device 6100 may confirm the selected operation by illuminating or blinking the backlit indicator 6221, 6222 associated with the second button 6232 or the third button 6233. To confirm and proceed with the selected operation, a user depresses the fourth button 6234. After the fourth button 6234 is depressed, the delivery device 6100 executes the selected operation. In an alternative embodiment, depressing the second button 6232 initiates the priming operation, depressing the third button 6233 imitates a mixing of the two components, and depressing the fourth button 6234 initiates the injection operation, after the third button 6233 has been depressed and the two components have begun mixing. In some embodiments, the first button 6231 (or any of the power buttons described herein) can initiate a start-up procedure to cycle the drive assembly 6150 through its entire range of motion, or range of motion required for a desired operation, to verify that the drive components of the drive assembly 6150 are functioning properly. If a fault is detected during the start-up procedure, the electronic control system 6200 (or any other electronic control systems described here) can prevent the priming operation or the injection operation from executing.

Figure 49:
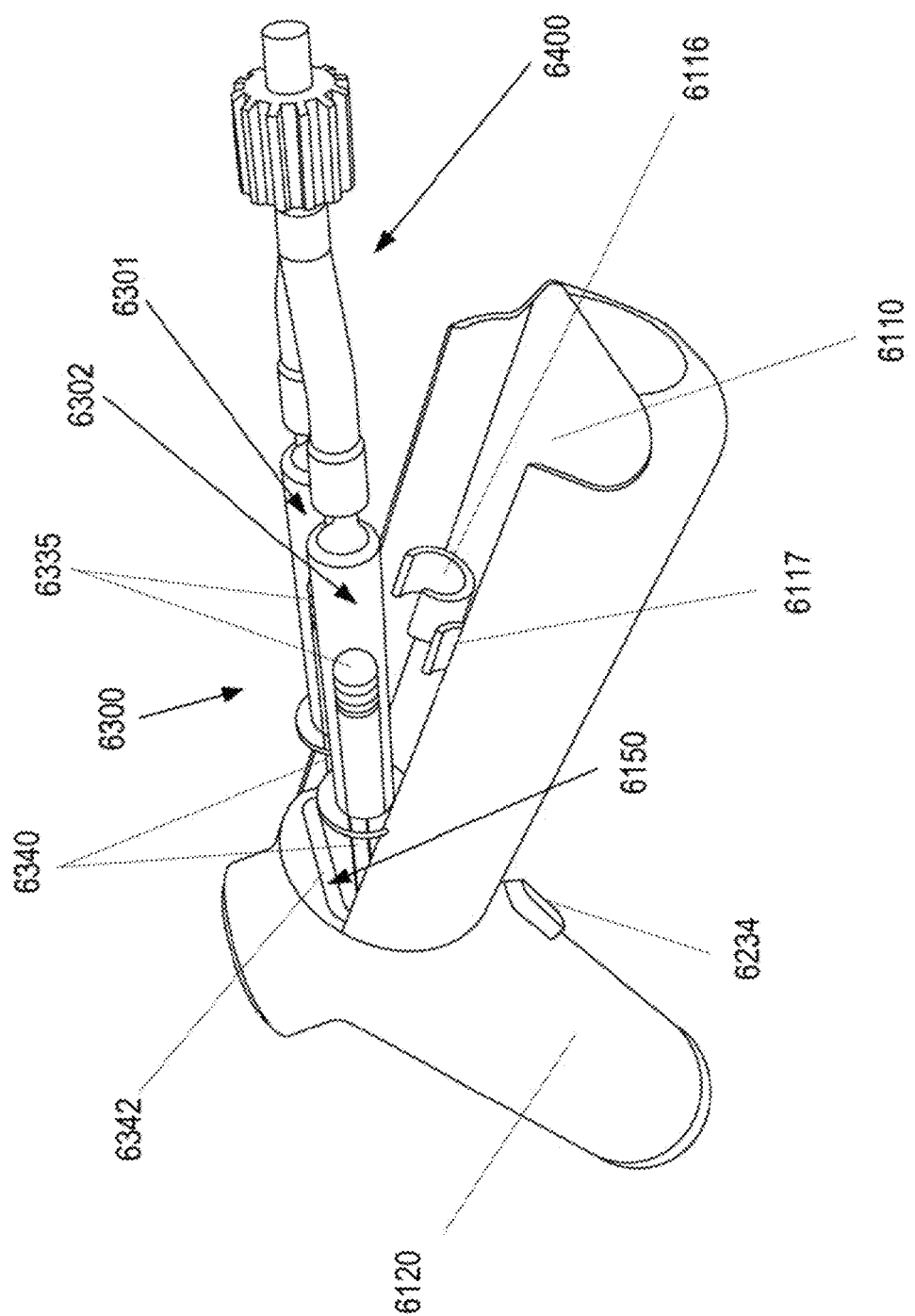
FIG. 49 is a front perspective view of the delivery system of FIG. 47 illustrating a container assembly detached from a housing.
Figure 50B:
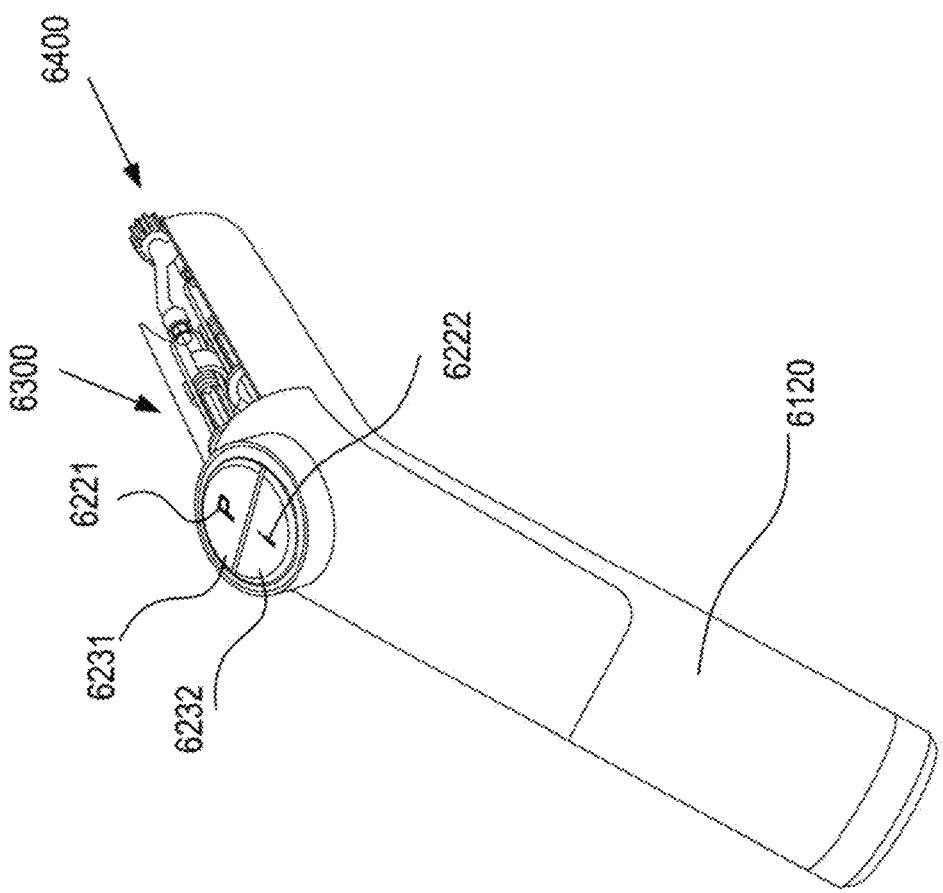
FIG. 50B is a rear perspective view of the delivery system of FIG. 47 illustrating a container assembly secured to a housing.
Figure 50A:
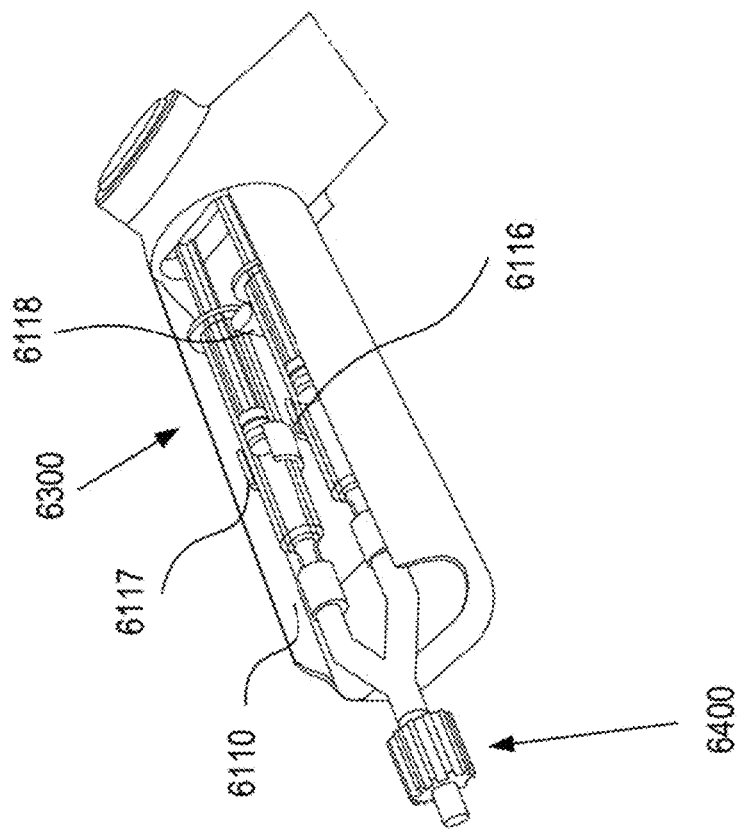
FIG. 50A is a front perspective view of the delivery system of FIG. 47 illustrating a container assembly secured to a housing.
Figure 51B:
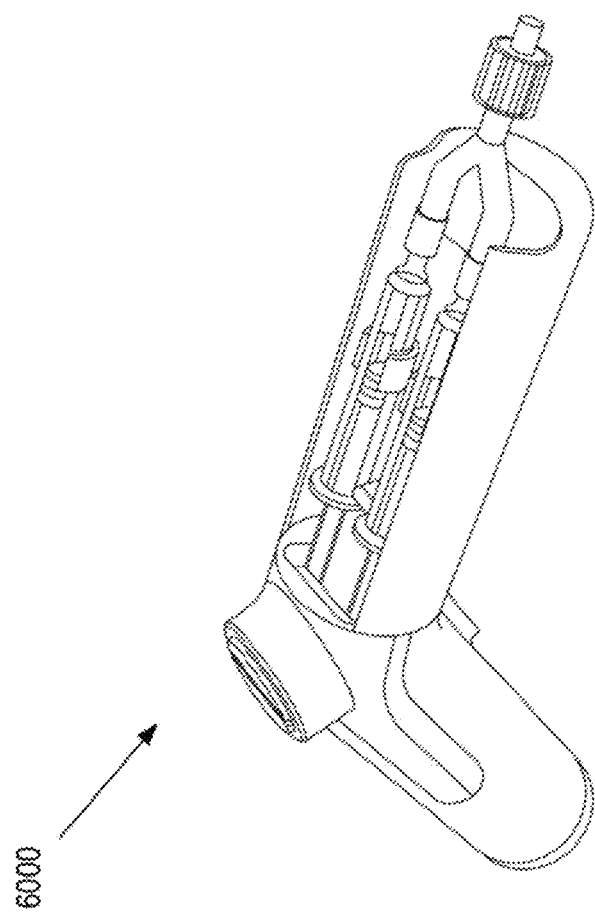
FIG. 51B is a rear perspective view of the delivery system of FIG. 47.
Figure 51A:
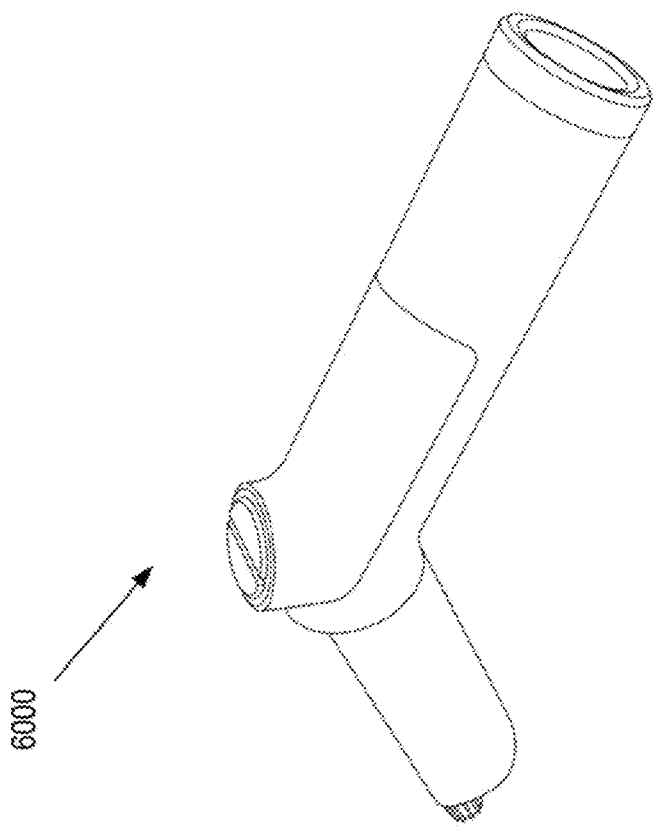
FIG. 51A is a front perspective view of the delivery system of FIG. 47 illustrating a container assembly secured to a housing.
Figure 52:
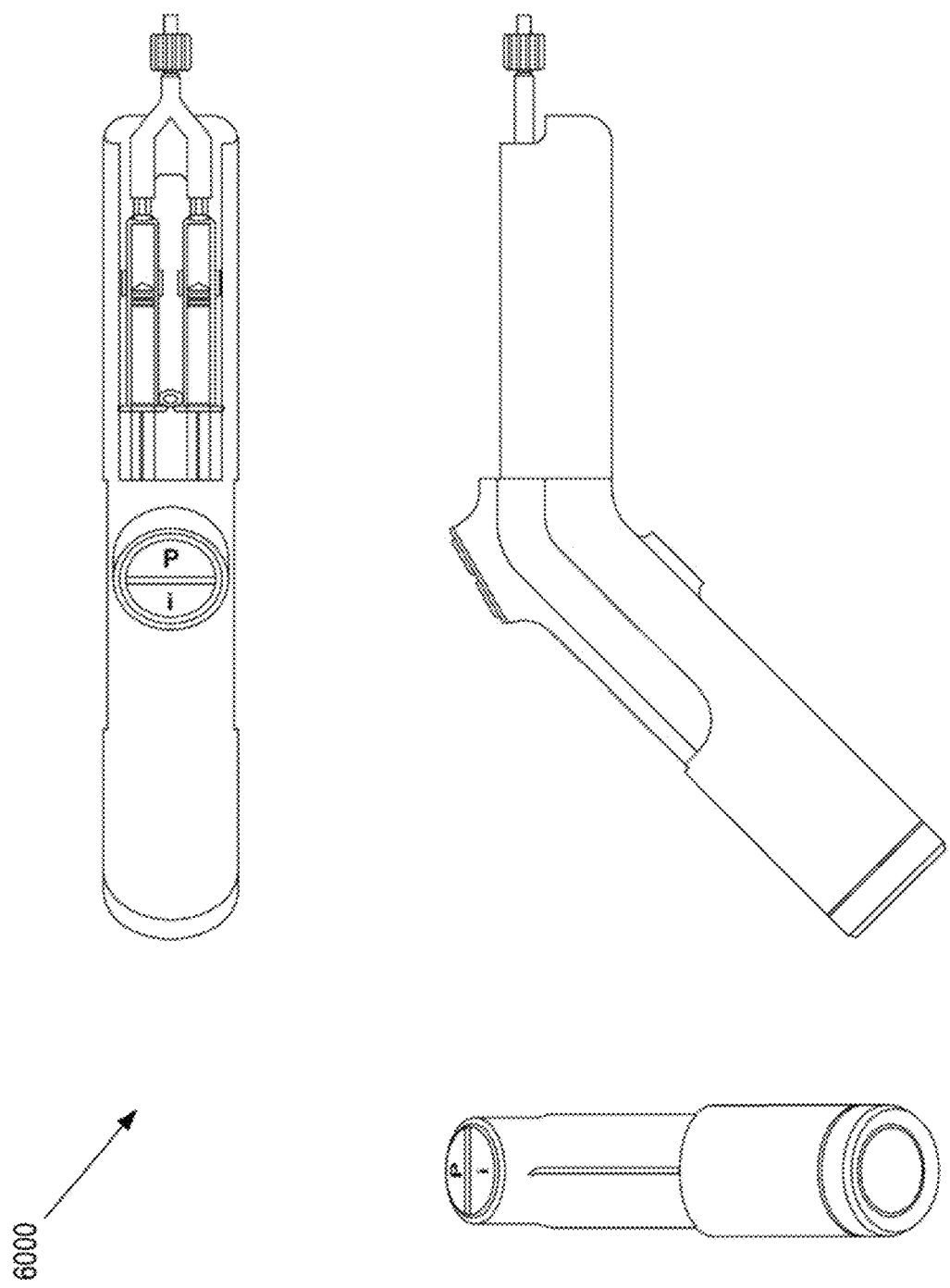
FIG. 52 is an orthographic view of the delivery system of FIG. 47.

As shown in FIGS. 49 and 51, the housing 6110 includes a first retainer portion 6116, a second retainer portion 6117, and a third retainer portion 6118. At least one of the first retainer portion 6116, the second retainer portion 6117, or the third retainer portion 6118 is configured to secure the container assembly 6300 to the housing 6110. In one embodiment, the first retainer portion 6116 and the second retainer portion 6117 include a C-shaped or U-shaped cross-section configured to grip an outer surface of the first container 6301 and the second container 6302. The third retainer portion 6118 extends from a base surface of the housing 6110 and abuts a second end 6332 of the container assembly 6300. The third retainer portion 6118 prevents the container assembly 6300 from moving in the axial direction. The location of the retainer portion 6118 enables the container assembly 6300 to be installed onto the housing 6110 at a predefined location along an axis of travel of the plungers 6340. The first and second retainer portions 6116, 6117 further prevent lateral movement of the container assembly 6300 relative to the axis of travel of the plungers 6340. As such, the container assembly 6300 can be predictably installed onto the housing 6110 such that the drive assembly 6150 engages the plungers 6340 consistently at a predetermined home position without inadvertently actuating the plungers 6340. For example, the drive assembly 6150 may be placed in a retracted position (e.g., a home position described herein) such that the container assembly 6300 does not engage the drive assembly 6150 during installation onto the housing 6110. This prevents the plungers 6340 from actuating inadvertently. Once the container assembly 6300 has been installed on the housing 6110, the drive assembly 6150 can perform the priming operation and/or injection operation using known locations based on the home position, described herein, thereby eliminating the need for a separate alignment or calibration procedure.

FIGS. 53-56 show a delivery system 7000 according to an embodiment. As described herein, the delivery system 7000 is configured to convey and combine multiple biomaterial components to form a biomaterial product that is delivered to a target location.

Figure 53:
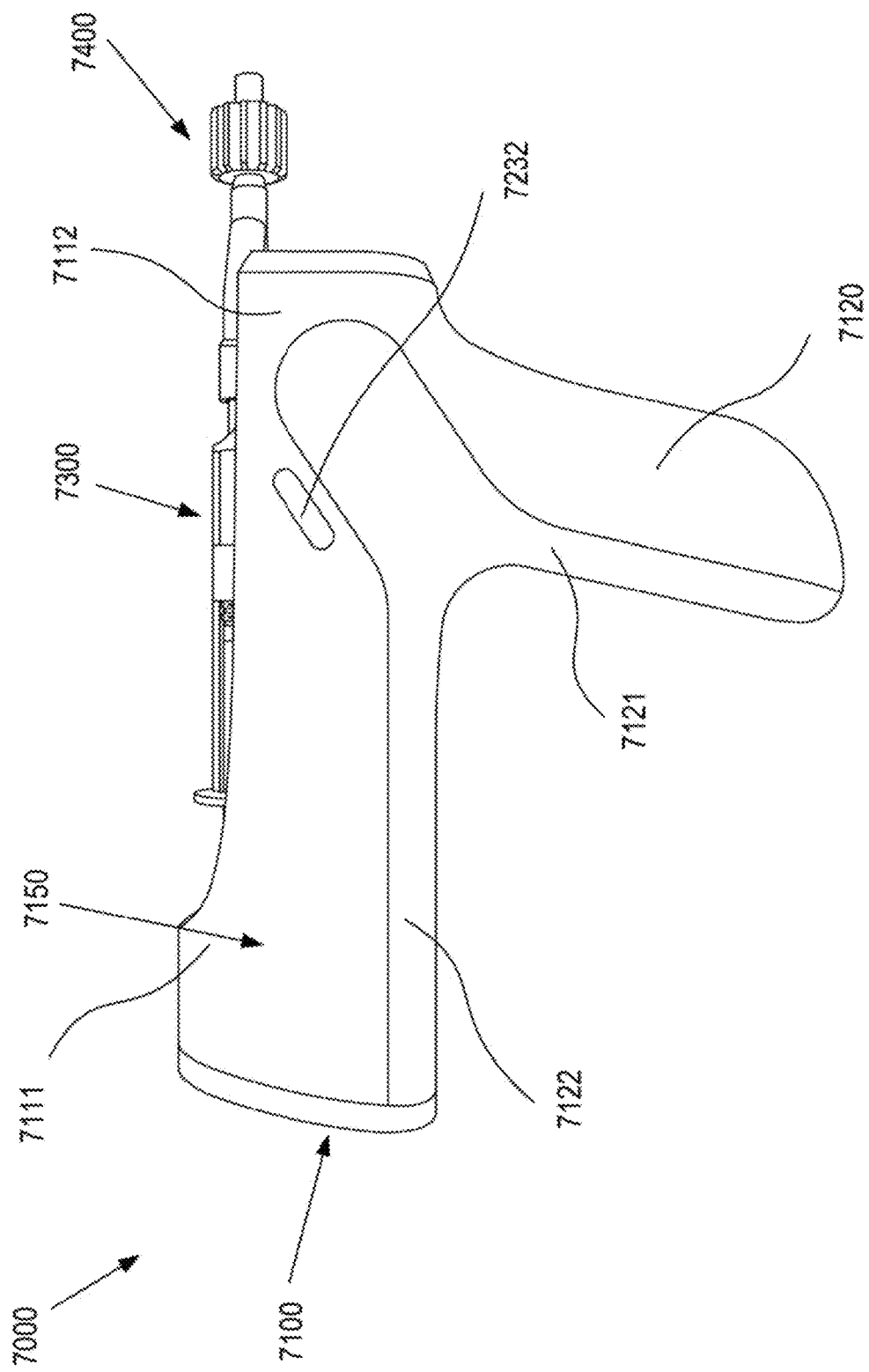
FIG. 53 is a side view of a delivery system according to an embodiment.
Figure 54:
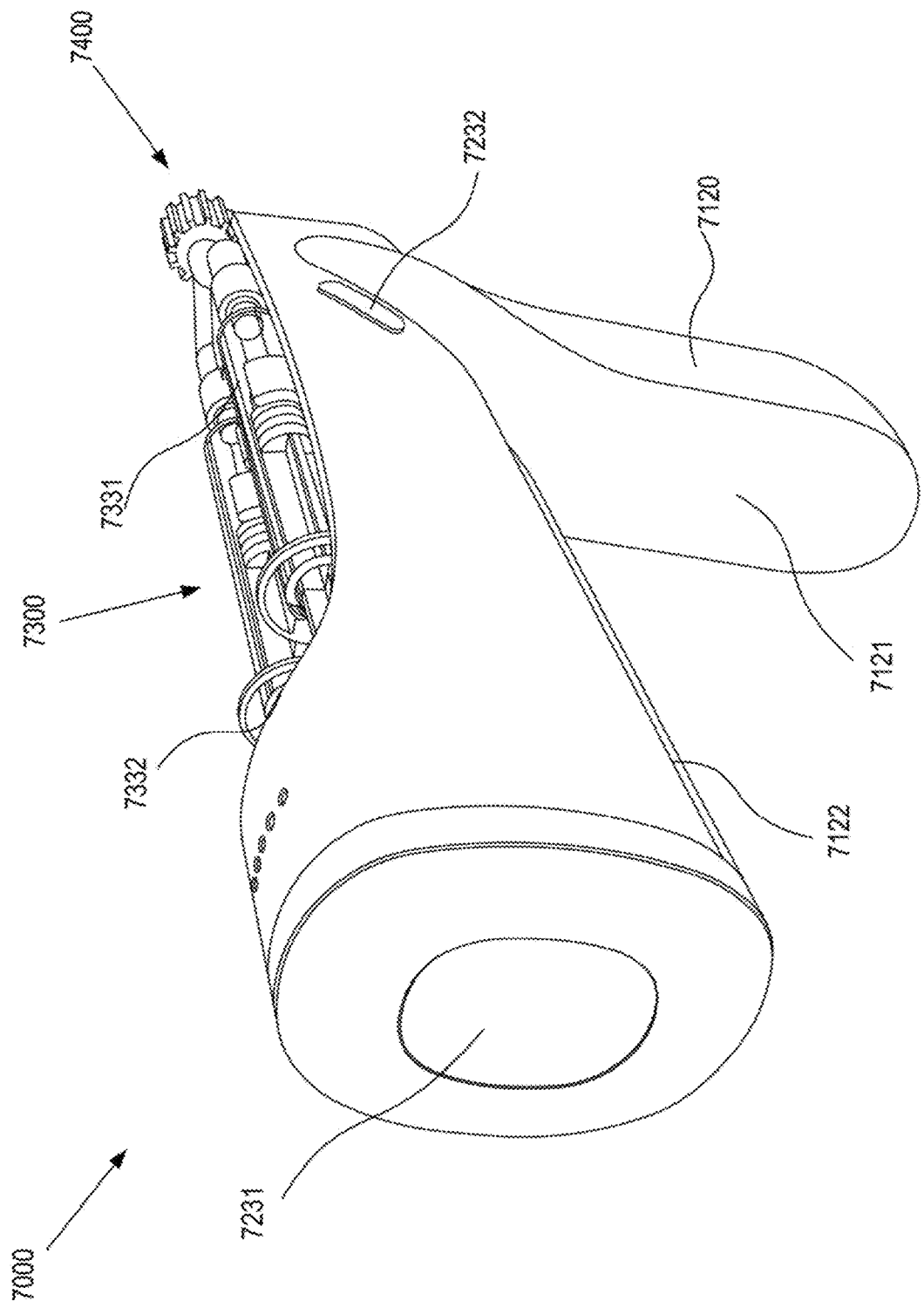
FIG. 54 is a rear perspective view of the delivery system of FIG. 53 illustrating a power button and status indicators.

The system 7000 includes a delivery device 7100, an electronic control system 7200, a container assembly 7300, and a connector 7400. The delivery device 7100 includes a housing 7110, a drive assembly 7150, and a handle portion 7120. As shown in FIGS. 53 and 54, the housing 7110 extends from a proximal end portion 7111 to a distal end portion 7112. The handle portion 7120 extends from the distal end portion 7112. The handle portion 7120 can include a textured or perforated surface 7121 to improve grip. The handle portion 7120 can further include a wrist support portion 7122 to further improve stability of the delivery device 7100 in the hand of a user during operation.

Similar to the other container assemblies described above, the container assembly 7300 includes a first container 7301 and a second container 7302. The container assembly 7300 further includes a first end 7331 configured to couple to the connector 7400, and a second end 7332 that includes a flange portion 7343 configured to receive an input force from the drive assembly 7150. The drive system 7150 is configured to drive the flange portion 7343 and in turn actuate the plungers 7340 to expel a first component from the first container 7301 and a second component from the second container 7302. As the first and second components are expelled from the first container 7301 and the second container 7302, respectively, the first and second components are conveyed to the connector 7400. The components can be mixed, crosslinked, and dispensed from the connector 7400 in the same manner as other connectors described above.

The electronic control system 7200 is configured to control the actuation and output of the drive assembly 7150 and is operable to control delivery characteristics of the delivery device 7100 in the same manner as the other delivery devices and methods described above. The electronic control system 7200 includes one or more buttons 7230. A first button 7321 is positioned on the proximal end portion 7111 of the housing 7110.

Figure 56:
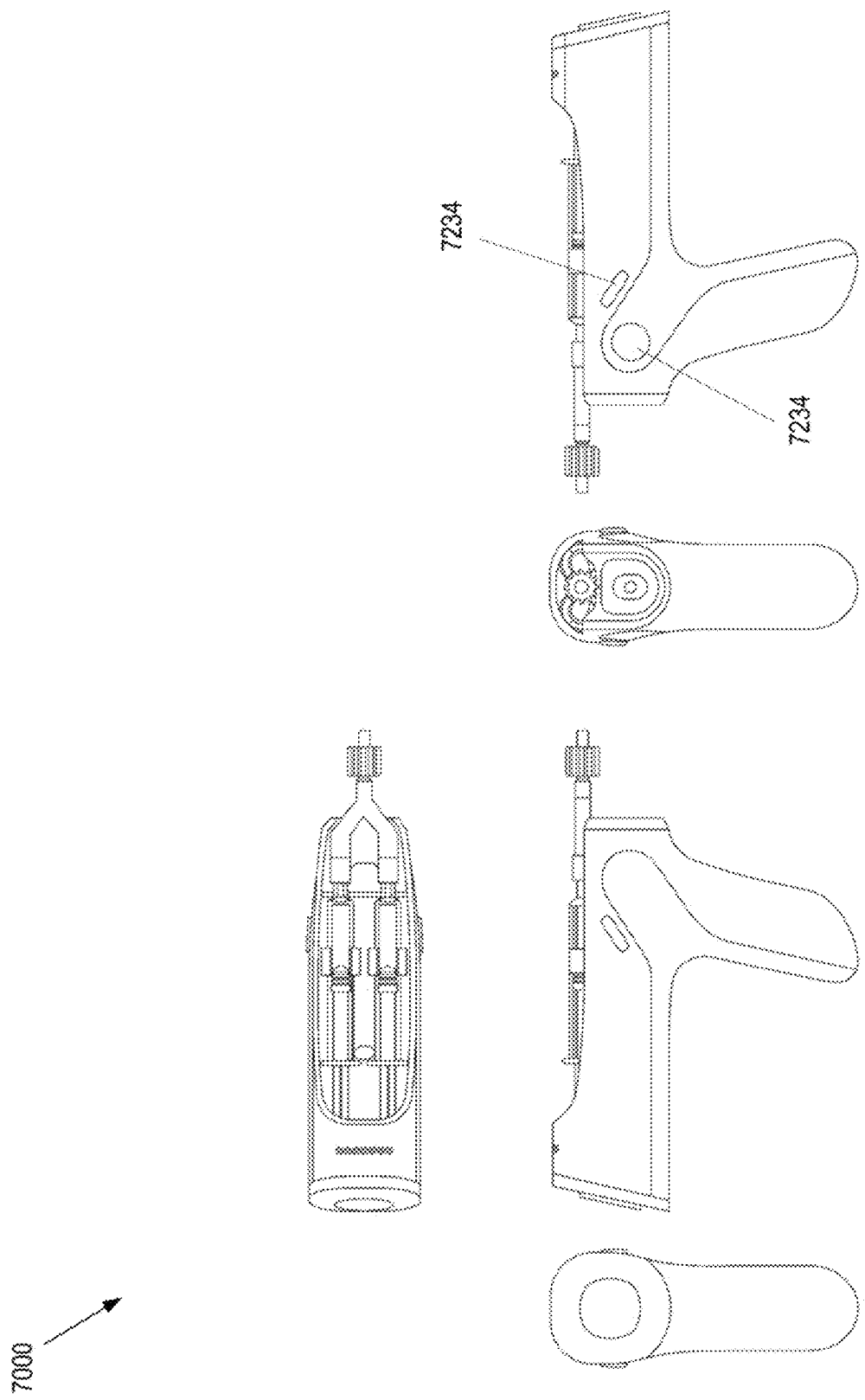
FIG. 56 is an orthographic view of the delivery system of FIG. 53.

As shown in FIGS. 53 and 56, the second and third buttons 7232, 7233 are positioned above the handle portion 7120 on either side of the housing 7110. The fourth button 7234 is positioned on the handle portion 7120 and permits a user to access the fourth button 7234 via their thumb while gripping the handle portion 7120, for example. The electronic control system 7200 further includes one or more visual indicators 7221, 7222, 7223. For example, the one or more visual indicators 7221, 7222, 7223 can be LED indicators to provide visual feedback or operating status of the delivery device 7100 to a user. In some embodiments, an operation or work light 7224 is provided at the distal end portion 7112 of the housing 7110 to provide additional illumination on an operating area of a patient. In some embodiments, the work light 7224 can be illuminated when the first button 7231 is pressed, or can be illuminated via a separate light button (not shown).

The first button 7231 is configured as a power button to turn on and off the delivery device 7100. The second button 7232 is configured as a prime button for initiating a priming operation (e.g., actuating the drive assembly 7150 to convey the first component and the second component into the connector 7400). The delivery device 7100 is operable to perform any of the priming operations described herein. The third button 7233 is configured as an injection button for initiating an injection operation (e.g., mixing the two components to form a biomaterial and dispensing the biomaterial into a body lumen). The delivery device 7100 is operable to perform any of the injection or controlled delivery operations described herein. The fourth button 7234 can be programmed or assigned as a trigger button. For example, depressing either the second button 7232 or the third button 7233 may prepare the delivery device 7100 for the priming operation or the injection operation, respectively. The delivery device 7100 may confirm the selected operation by illuminating or blinking one or more of the LED indicators 7221, 7222, 7223. To confirm and proceed with the selected operation, a user depresses the fourth button 7234. After the fourth button 7234 is depressed, the delivery device 7100 executes the selected operation.

Figure 55:
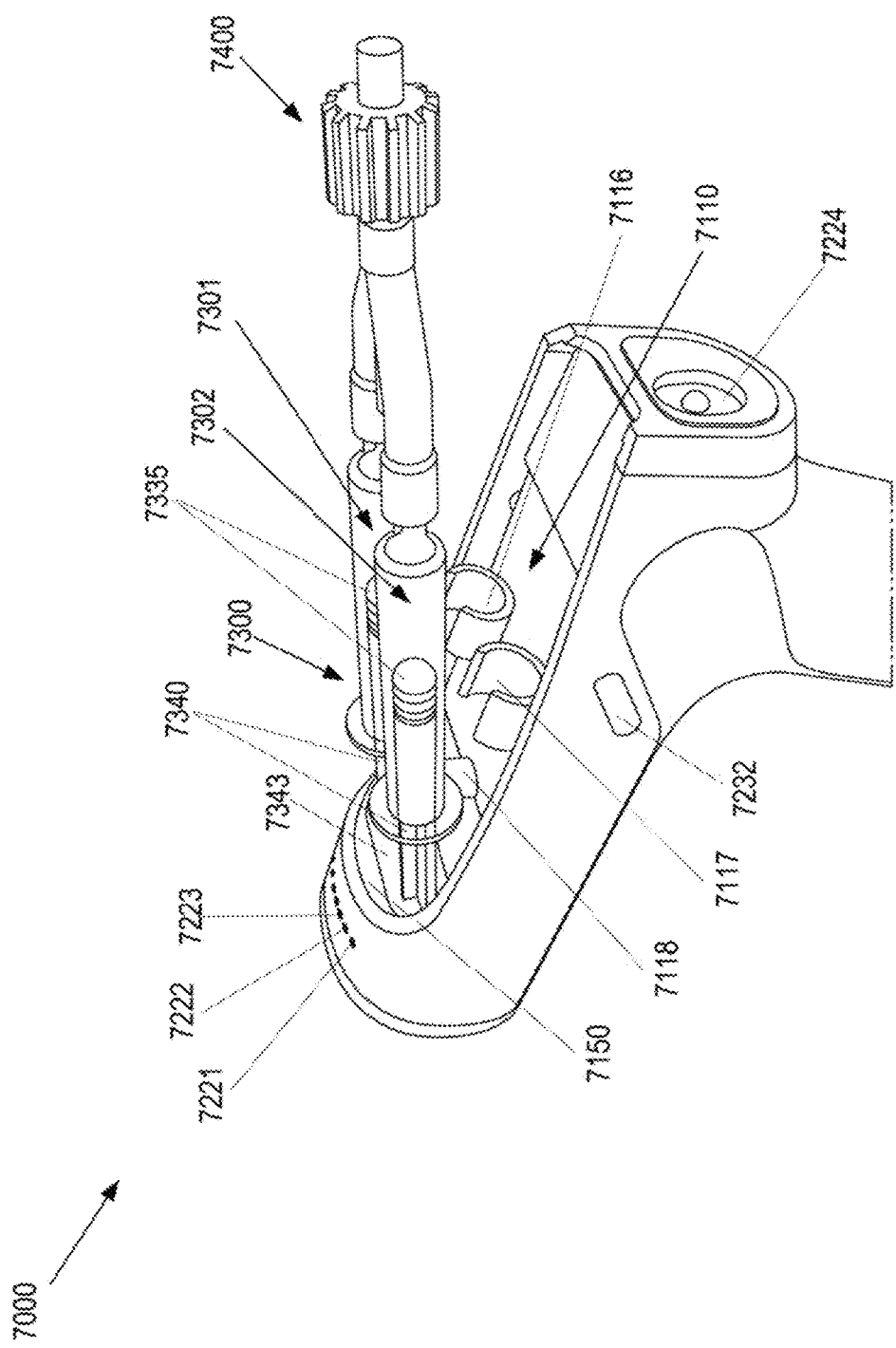
FIG. 55 is a front perspective view of the delivery system of FIG. 53 illustrating a container assembly detached from a housing.

As shown in FIG. 55, the housing 7110 includes a first retainer portion 7116, a second retainer portion 7117, and a third retainer portion 7118. At least one of the first retainer portion 7116, the second retainer portion 7117, or the third retainer portion 7118 is configured to secure the container assembly 7300 to the housing 7110. In one embodiment, the first retainer portion 7116 and the second retainer portion 7117 include a C-shaped or U-shaped cross-section configured to grip an outer surface of the first container 7301 and the second container 7302. The third retainer portion 7118 extends from a base surface of the housing 7110 and abuts a second end 7332 of the container assembly 7300. The third retainer portion 7118 prevents the container assembly 7300 from moving in the axial direction. The location of the retainer portion 7118 enables the container assembly 7300 to be installed onto the housing 7110 at a predefined location along an axis of travel of the plungers 7340. The first and second retainer portions 7116, 7117 further prevent lateral movement of the container assembly 7300 relative to the axis of travel of the plungers 7340. As such, the container assembly 7300 can be predictably installed onto the housing 7110 such that positions of the drive assembly 7150 is known relative to the plungers 7340. For example, the drive assembly 7150 may be placed in a retracted position (e.g., a home position described herein) such that the container assembly 7300 does not engage the drive assembly 7150 during installation onto the housing 7110. This prevents the plungers 7340 from actuating inadvertently. Once the container assembly 7300 has been installed on the housing 7110, the drive assembly 7150 can perform the priming operation and/or injection operation using known locations based on the home position, described herein, thereby eliminating the need for a separate alignment or calibration procedure. As described herein, the system 7000 may include sensors to detect whether the container assembly 7300 and/or the connector 7400 are properly mounted and coupled prior to initiating the priming operation or injection operation.

With reference to FIGS. 57-60, experimental test results on canine and rabbit vas deferens will now be discussed. As would be appreciated by one skilled in the art, the vas deferens of a human and a canine are similar in many ways including anatomical similarity as well wall thickness, and overall vessel length. By contrast, the vas deferens of a rabbit have thinner vessel walls, different anatomical structures, and are shorter than the vas deferens of a human. As described herein, controlled formation and delivery of biomaterials to a target site is critical for preventing damage to the target site or surrounding areas. Controlled formation and delivery of the biomaterials to the target site is also important to ensure that the delivered biomaterials are efficacious for the intended application. For example, biomaterials such as a hydrogel can be conveyed into a vas deferens to form an occlusion to block sperm as a form of contraception.

Figure 57:
FIG. 57 is a cross-sectional view of a normal canine vas deferens.

As shown in FIG. 57, a cross-section of a normal canine vas deferens 8000 is shown. The canine vas deferens 8000 includes a lumen 8100 and smooth muscles 8200 surrounding the lumen 8010. In one test case, the system 4000 was configured to mix components within the cartridge 4350 and deliver a formed hydrogel to a canine vas deferens (not shown) via the catheter 4510 at a rate of 400 µL/min and with a total delivered volume of 200 µL. In this test case, no vessel damage or leakage of the hydrogel was observed and the delivery and implant of the formed hydrogel into the canine vas deferens was efficacious (azoospermia on subsequent semen collections post-implantation).

Figure 58:
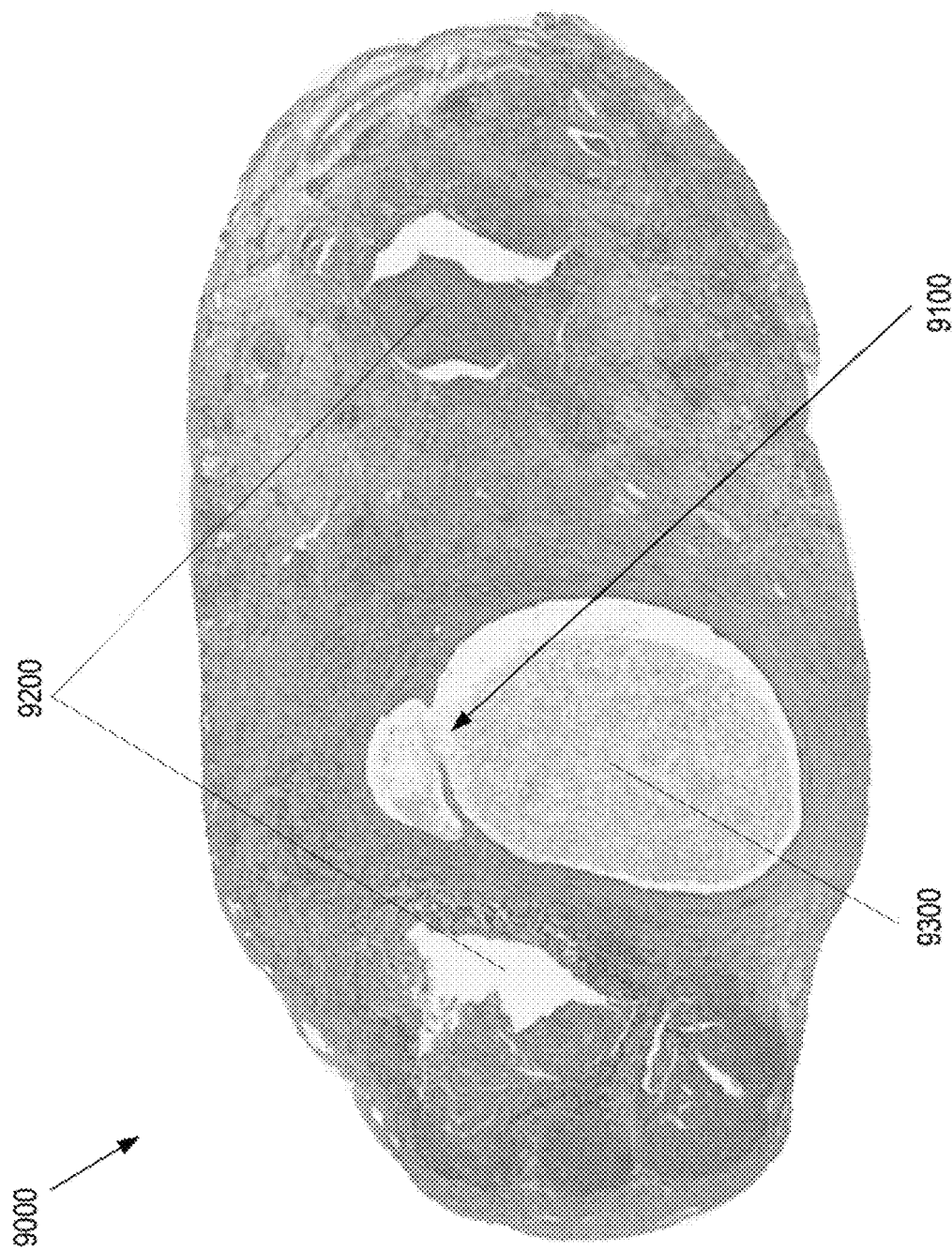
FIG. 58 is a cross-sectional view of a canine vas deferens after an injection event.
Figure 59:
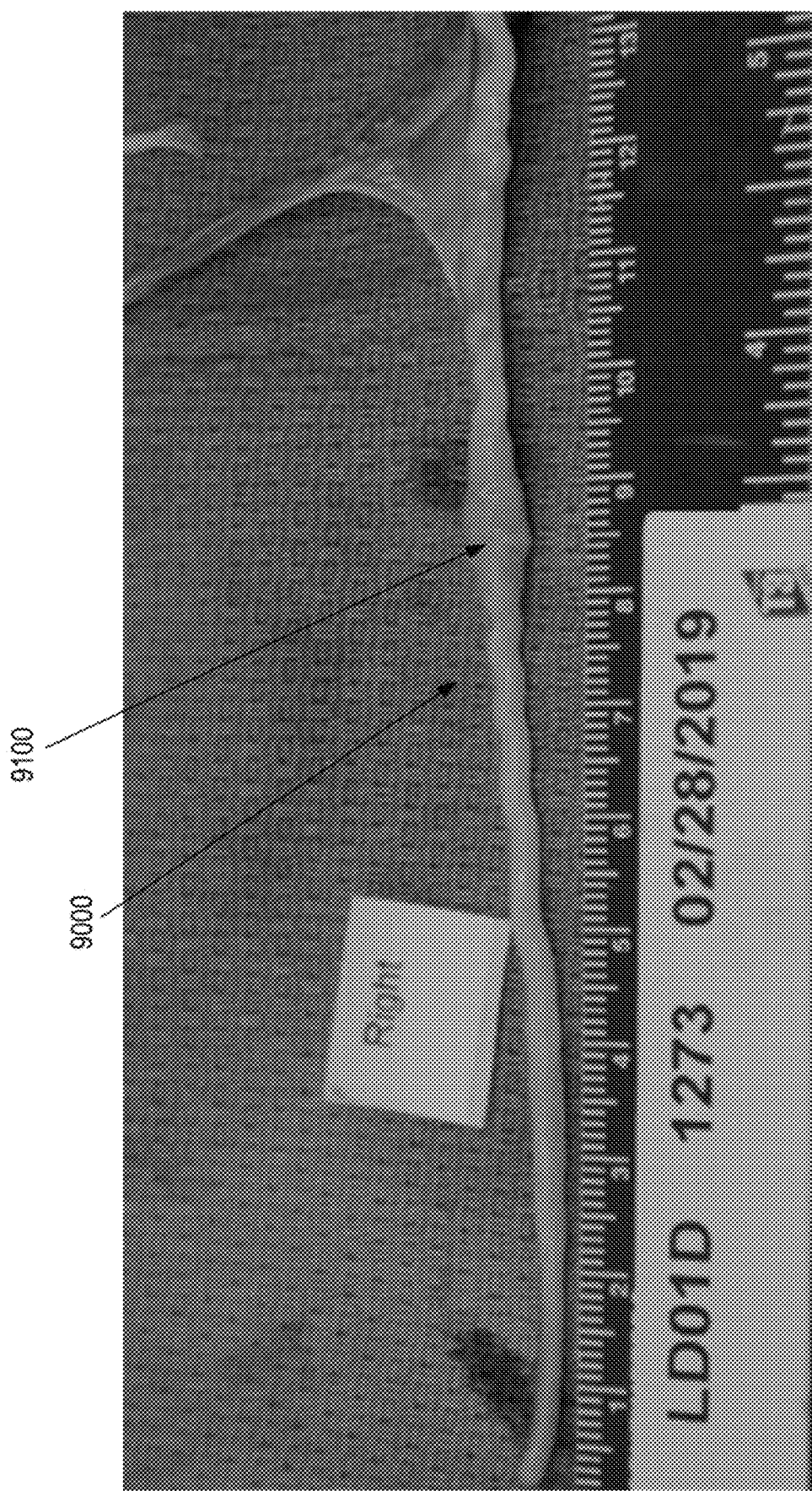
FIG. 59 is an external image of a canine vas deferens after an injection event.
Figure 60:
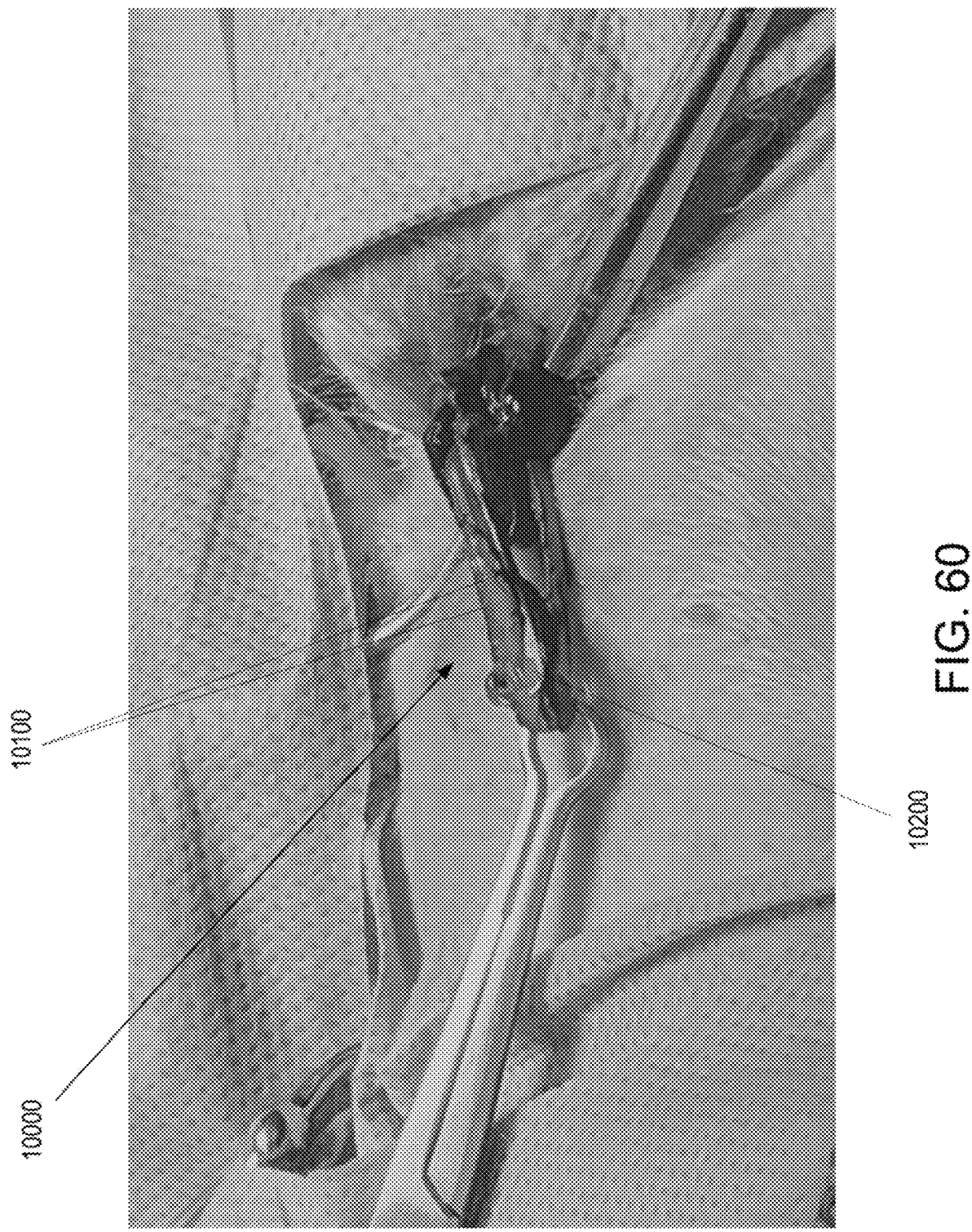
FIG. 60 is an external image of a rabbit vas deferens after an injection event.

By comparison, in another test case, the system 4000 was configured to mix components within the cartridge 4350 and deliver a formed hydrogel 9300 to a canine vas deferens 9000 via the catheter 4510 at a rate of 3200 µL/min and with a total delivered volume of 75 µL. As shown in FIGS. 58 and 59, the canine vas deferens 9000 had observable histological damage to the lumen 9100 and the surrounding muscles 9200 after delivery of the hydrogel 9300. By way of another comparison, in one test case, the system 4000 was configured to mix components within the cartridge 4350 and deliver a formed hydrogel to a rabbit vas deferens 10000 via the catheter 4510 at a rate of 400 µL/min and with a total delivered volume of 200 µL. As shown in FIG. 60, the rabbit vas deferens 10000 was damaged with burst outer vessel walls 10100 and formed hydrogel 10200 was leaking out. In view of the above, the same injection parameters applied may result in an efficacious implant in a canine vas deferens while causing damage in a rabbit vas deferens. Changing the rate of delivery and/or input injection forces for the same type of target site (e.g., two different canine vas deferens) could result in drastically different outcomes—an efficacious implant under one scenario and damage to the vas deferens in the other scenario.

As demonstrated in the above experimental test results, precise control of at least the injection forces applied and delivery speed of the formed biomaterial to a target site, which can be achieved with the systems and methods described herein, is critical for successfully delivering the biomaterial to a target site without damaging the site or surrounding areas.

While the machine-readable storage medium (e.g., within the electronic control system 2200) is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

The present disclosure also relates to an apparatus for performing the operations herein. This apparatus may be specially constructed for the intended purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, Universal Serial Bus (USB) flash drives, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general-purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape;

optical storage media such as Compact Disc/Digital Video Discs (CD/DVDs), Compact Disc-Read Only Memories (CD-ROMs), Universal Serial Bus (USB) flash drives, and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Any of the components and sub-components described herein can be included in any of the embodiments unless mutually exclusive. For example, in some embodiments, the apparatus may be able to perform one or more injections, such as delivering two biomaterials into the same patient from the same apparatus. In some embodiments, the apparatus performs a single priming step and single injection; performs a single priming step and multiple injections; performs multiple priming steps and a single injection; and performs multiple priming steps and multiple injections. The priming and injection steps is performed in a pre-defined sequence or performed in any order. The priming steps may include the same or different volumes. If multiple injections are done, the injections may have the same or different volumes each time.

In some embodiments, the apparatus is used to inject a biomaterial that is formed from one or more precursors. For example, two macromer solutions are injected that cross-link with each other to form a hydrogel material. The apparatus injects solutions into the body, such that the solutions form a hydrogel in situ. In some embodiments, the apparatus is used to inject the formed biomaterial into the body, e.g. cross-linked hydrogel. The hydrogel may continue to gel and/or cross-link in situ once injected or can be completely gelled or cross-linked by the time it exits the apparatus. In this regard, the apparatus facilitates the merging or mixing of the two or more different solutions into a single stream.

In some embodiments, the apparatus is a handheld device with a screen similar to a cystoscope. The housing for the apparatus is designed such that it includes a grip for the user to hold the apparatus, a trigger, and buttons including on and off buttons, priming buttons, and inject buttons. For example, the apparatus is configured for a user to push a button to perform the injection. In some embodiments, the trigger controls the syringe plunger actuation (piston) and therefore, control the dispensing volume. In some embodiments, the volume is dependent upon the force that is pressed on the trigger. In some embodiments, the actuation of the syringe plunger is pre-set, regardless of the force applied by the user on the trigger, such that a consistent amount of volume is extruded from the apparatus.

In some embodiments, the apparatus includes one or more springs to apply the correct amount of pressure. The one or more springs are reusable by tensioning. The one or more springs controls movement of a piston, actuator rod, or similar device, for imparting pressure on the syringes. The precise force or pressure can be adjusted by setting the specific tension level on the one or more springs.

In some embodiments, the type and size of syringe selected for the apparatus impacts the injection parameters and biomaterial extruded. In some embodiments, a material of the syringe is glass, plastic, or a combination of both. The syringe can be lubricated or non-lubricated. In some embodiments, the syringe contains from about 0.1 mL to 100 mL in volume. For example, the syringes can be 0.5 cc, 1 cc, 2 cc, 5 cc, 10 cc, 20 cc, 50 cc, and/or 100 cc syringes. An inner diameter of the syringes can range from about 0.2 mm to 50 mm. For example, 1 cc plastic BD syringes may be 4.64 mm in diameter. The cylindrical cross-sectional area may range from 0.000026 to 1.5 in$^2$. In some embodiments, the plunger can be selected for a particular application based on different attributes including, for example, manufacturer, volume, length, inner diameter and lubrication chosen. The plunger may be lubricated or non-lubricated, and be made of synthetic rubber, natural rubber, thermoplastic, and/or an elastomer. In some embodiments, the syringes may be locked into a holder, also referred to as a chassis. In one aspect, the syringes can be loaded or included within a cassette-style syringe holder, which may be disposed after use.

In one embodiment, the apparatus contains a Y-connector (also known as blending connector) which contains channels for solutions to flow through. For example, manufacturers of Y-connectors include, but are not limited to, Nordson Medical (Micromedics), Medmix, and Sulzer. In one embodiment, the channels of the Y-connector do not facilitate mixing of the precursor solutions. Therefore, the solutions may merge or mix in the needle and/or catheter hub. In some embodiments, the dual lumen catheter or needle is attached to the Y-connector to prevent any mixing or merging of the solutions within the apparatus. In some embodiments, the Y-connector is attached to the syringe(s) on one end.

In some embodiments, the apparatus includes tubing to extend the distance from the syringes within the apparatus to the Y-connector and/or angiocath/needle. For example, manufacturers of such tubing include, but are not limited to, Zeus, Medline and Cook Medical. In some embodiments, mixing of the two solutions occurs in the extension tubing. In some embodiments, mixing does not occur in the tubing. In some embodiments, a mixing chamber is attached to the Y-connector, such that the solutions merge or mix within the mixing chamber after exiting the Y-connector. In some embodiments, the mixing chamber includes a number of mixing elements, which determine the degree of mixing, such as 1 to 20 mixing elements. In some embodiments, a needle and/or catheter is attached to the mixing chamber.

In some embodiments, the apparatus includes a catheter or needle or combination of both, by which the biomaterial can be extruded from. The catheter or needle or combination is chosen based on a desired application, location of implantation, chemical properties of the biomaterial (e.g. viscosity), and desired injection volume, speed, and force. The needle and/or catheter is configured to deliver the biomaterial subdermally, percutaneously, or intraluminally. In some embodiments, the apparatus includes a needle-sheathed catheter or a catheter-sheathed needle. The maximum needle size/gauge is determined by the lumen of the vessel, duct, or organ which will receive the external stimulus and as a result the exact size of catheter, needle, or instrument is not critical so long as it is shaped and sized appropriately for a particular application. The gauged needle and/or catheter can have a diameter ranging for example between about 100 um and 5 mm, including 0.1 mm, 0.2 mm, 0.3 mm, 0.4 mm, 0.5 mm, 0.6 mm, 0.7 mm, 0.8 mm, 0.9 mm, 1.0 mm, 1 mm, 2 mm, 3 mm, 4 mm, or 5 mm. In some embodiments, the needle diameter is preferably between 0.3 mm to 1 mm. In some embodiments, the size of the needle and/or catheter is from about 6 gauge to 34 gauge, such as from about 10 gauge to 34 gauge, or about from 15 gauge to 32 gauge, or about from 20 gauge to 26 gauge, or about from 22 gauge to 26 gauge, and so on. In some embodiments, the size of the needle is between about 21 gauge and 31 gauge. In some embodiments, the needle can be extra thin walled (XXTW), extra thin walled (XTW), thin walled (TW), or regular walled (RW). For example, standard needle sizes are readily available such as at http://www.sigmaaldrich.com/chemistry/stockroom-reagents/learning-center/technical-library/needle-gauge-chart.html. In some embodiments, the needle is used to introduce a secondary catheter within the lumen of the vessel. In one aspect, the needle or catheter can have a length between about 0.1 inch and 15 inches, preferably from about 0.5 inch to 10 inches, such as from about 0.8 to 5 inches, or from about 0.4 to 1 or 2 or 3 inches. In some embodiments, the needle is echogenic, or visible on ultrasound.

In some embodiments, the apparatus is configured to operate with a dead volume, depending on the components used in the apparatus. For example, the needle, catheter, and/or Y-connector is configured to contribute about 10-1,000 µL of dead volume. In some embodiments, the apparatus is configured to operate with one or more start-stop cycles, one or more priming steps, and one or more implantations. For example, the apparatus may have 1, 2, 3, 4, 5, etc. start-stop cycles. In some embodiments, one step is used to prime the Y-connector, needle/catheter, and/or extension tubing with the precursor solution(s) to eliminate the dead volume prior to injecting the biomaterial.

In some embodiments, the apparatus is configured to inject three or more solutions or combinations of materials. The apparatus is configured to mix any of the components, for example, two components may mix within the apparatus, while a third does not. In some embodiments, all three components can merge at the same location, such as in the Y-connector or needle/catheter hub or extension tubing. In some embodiments, the apparatus includes a subsystem that allows for the introduction of a fluid through a catheter system. In some embodiments, the apparatus includes a fluid reservoir, or a separate fluid reservoir is fluidly coupled to the apparatus.

In some embodiments, the device is configured to deliver one or more combinations of matter in different states such as solid, liquid, and gas, in any required combination or order based. In some embodiments, the device delivers air through the needle/catheter/tubing followed by injection of multiple solutions. In another aspect, the device can deliver a liquid such as saline or water-for-injection, followed by injection of the biomaterial. In one embodiment, the biomaterial that is extruded from the device is a hydrogel.

In some embodiments, operating parameters of the apparatus is optimized to perform consistent and/or controlled injection. These parameters include, but are not limited to, the injection rate, volume injected, peak extrusion force, peak pressure in syringes, distance plungers move, plunger speed, and plunger acceleration. As operating parameters are altered for particular applications, the resulting injection and delivery of the biomaterial is altered. For example, the chemical, mechanical, and/or biological properties of the biomaterial (e.g. hydrogel or implant), including, but not limited to, the length, width, and volume of the implant, the gelation rate of the implant, the shape of the implant, and how the implant interacts with the surrounding tissue can be altered based on the operating parameters. The length of the implant may directly impact the efficacy of the device, such as for occlusion of the vas deferens for male contraception.

In some embodiments, the injection rate ranges from about pL/min to 150 mL/min, more preferably 1-10,000 µL/min.

In some embodiments, the injection rate is constant (cannot be adjusted by the user) or non-constant (can be adjusted). In some embodiments, the time period of is constant (non-adjustable) or non-constant (adjustable). Thus, the rate and/or length of time or both can be manipulated or set by a user to precisely control the injection volume. In one embodiment, the volume that is injected may range from 1 µL to 100 mL. For applications where the biomaterial is being implanted into a duct, vessel, or tissue that is restricted in size and/or diameter, a smaller volume ranging from about 1 µL to 1,000 µL may be more preferred. The injection volume may be optimized to prevent burst of the tissue or vessel. For occluding the vas deferens (which ranges in ID from about 0.5 to 0.8 mm), the preferred injection volume is from about 1 µL to 200 µL.

In some embodiments, the peak extrusion force that the apparatus is required to exert on the syringe plungers ranges from about 0.1 to 20 lbF. The force required depends on factors including, but not limited to, viscosity of the solution, the type of syringes (e.g., manufacturer, length, inner diameter), plunger, lubrication of syringe and/or plunger, and needle inner diameter. In some embodiments, the peak extrusion force is below 10 lbF. In some embodiments, the peak pressure in the syringe(s) ranges from about 0.1 to 20 mmHg. In some embodiments, a distance that the plungers move ranges from about 0.1 to 20 cm. In some embodiment, the plunger moves at a speed ranging from 0.1 to 10 mm/sec.

In some embodiments, the apparatus is configured to add a solvent (e.g. dissolving solution) to a powder (e.g. polymer) within the device prior to performing a priming or injection step. For example, a container such as syringe, vial, or ampule containing the polymer powder is loaded into a slot within the apparatus, where upon pressing a button and/or trigger, the apparatus fills the container with a solution to dissolve the powder. In some embodiments, a carrier solution is added to solids or dehydrated materials prior to delivery. In some embodiments, the dissolution or hydration of the dehydrated materials with the carrier solution is initiated via the user pressing a button, switch, or trigger, after which the user will be able to perform priming and injection steps. In some embodiments, after mixing of solids and the carrier solvent, the apparatus is configured to de-gas or remove air generated from the mixing of the liquids and the solids, prior to performing priming and/or injection steps.

In some embodiments, the biomaterial includes one or more of natural or synthetic monomers, polymers or copolymers, biocompatible monomers, polymers or copolymers, such as polystyrene, neoprene, polyetherether 10 ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers such as polytetrafluoroethylene (PTFE or TEFLON®), TEFLON® TFE (tetrafluoroethylene), polyethylene terephthalate (PET or PETE), TEFLON® FEP (fluorinated ethylene propylene), TEFLON® PFA (perfluoroalkoxy alkane), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly(DTH-iminocarbonate), poly (bisphenol A iminocarbonate), poly(orthoester) (POE), polycyanoacrylate (PCA), polyphosphazene, polyethyleneoxide (PEO), polyethylene glycol (PEG) or any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), polyoxazoline (POx), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, ethylene vinyl alcohol (EVOH), polyethylene oxide, PLLA or PlLA (poly(L-lactide) or poly(L-lactic acid)), poly(D,L-lactic acid), poly(D, L-lactide), polydimethylsiloxane or dimethicone (PDMS), poly(isopropyl acrylate) (PIPA), polyethylene vinyl acetate (PEVA), PEG styrene, polytetrafluoroethylene RFE such as TEFLON® RFE or KRYTOX® RFE, fluorinated polyethylene (FLPE or NALGENE®), methyl palmitate, temperature responsive polymers such as poly(N-isopropylacrylamide) (NIPA), polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly (lactide-co-caprolactone (PLCL), and/or chitosan.

In some embodiments, the dissolving solution for the polymer component(s) may be aqueous buffers (pH range 1-14): phosphate, citrate, acetate, histidine, lactate, tromethamine, gluconate, aspartate, glutamate, tartrate, succinate, malic acid, fumaric acid, alpha-ketoglutaric, and/or carbonate. Non-aqueous solvents include: dimethyl isosorbide, glycofurol 75, PEG 200, diglyme, tetrhydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene, acetonitrile. In some embodiments, when the polymer component is dissolved, the viscosity of the solution(s) that make up the biomaterial may range from 0.1 to 250,000 cP. The density of the solution may range from 0.1 to 20,000 kg/m$^3$. The temperature during extrusion may range from 2 to 45° C. The pH of the solution(s) may range from 1-14. The ionic strength of the solution(s) may range from 1 nM to 70 M.

In some embodiments, if two components are injected to form the biomaterial, then the ratio of the components may be varied such as 1:1, :1, 1:2, 3:1, 1:3, 4:1, 1:4, and up to 10:1 or 1:10. The gelation rate of the biomaterial may range from about 0.001 seconds to 60 minutes. The length of the formed biomaterial may range from about 0.1 to 60 cm. The volume of the formed biomaterial may range from about 0.001 to 100 mL.

In some embodiments, the biomaterial swells within the implantation space to lock or secure its placement. For example, a biomaterial in the form of a hydrogel may swell from about 1.5×-10× its initial volume. In some embodiments, the extruded biomaterial conforms to the space it is injected into. In some embodiments, the swelling of the biomaterial does not change volume within the implantation space, or shrinks to conform to a volume of the implantation space. In some embodiments, the apparatus injects a preformed biomaterial (does not cross-link, form, or gel in situ). Once injected, the biomaterial may or may not react with the implantation space. If a reaction does occur, it may be covalent or non-covalent. In some embodiments, the biomaterial adhesively interacts within the implantation space.

Although the electronic control system 2200 is shown as including specific modules, in other embodiments, the electronic control system 2200 (or any of the electronic control systems described herein) can include different modules or components than those shown in FIGS. 8 and 9. For example, in some embodiments, any of the electronic control systems described herein can include any other suitable modules, such as for example, a network module. The network module can facilitate communication between the electronic control system and other remote computing devices via a network (e.g., the Internet).

Although various embodiments have been described as having particular features and/or combinations of components, other embodiments are possible having a combination of any features and/or components from any of embodiments where appropriate. For example, any of the devices shown and described herein can include an electronic control system similar to the electronic control system 2200 as described herein.

What is claimed is:
1. An apparatus, comprising:
   a housing configured to receive at least a portion of a container assembly, the container assembly containing a first component and a second component, the first component being separate from the second component within the container assembly, the first component formulated to be crosslinked with the second component to form a hydrogel, the container assembly configured to be coupled to a connector; and
   a drive assembly including a driver, a drive member, and an electronic control system, the driver configured to produce a drive force to move the drive member, the drive member configured to be operatively coupled to the container assembly such that movement of the drive member causes a portion of the first component and a portion of the second component to be conveyed from the container assembly to the connector, the electronic control system is configured to control a drive member velocity of the drive member to maintain an exit velocity of the portion of the first component and the portion of the second component within a predetermined velocity range during a time period.

2. The apparatus of claim 1, wherein the predetermined velocity range is bounded by an upper velocity threshold and a lower velocity threshold.

3. The apparatus of claim 2, wherein the upper velocity threshold and the lower velocity threshold are such that a delivered volume of the portion of the first component and the portion of the second component is within a delivered volume range.

4. The apparatus of claim 3, wherein the delivered volume range is between about 5 microliters and about 1000 microliters.

5. The apparatus of claim 2, wherein the lower velocity threshold is above zero.

6. The apparatus of claim 1, wherein:
the container assembly includes a first container and a second container, the first container containing the first component and a first plunger, the second container containing the second component and a second plunger;
the driver is an electromechanical driver; and
the drive member is configured to be engaged with the first plunger and the second plunger such that movement of the drive member moves the first plunger within the first container and the second plunger within the second container.

7. The apparatus of claim 6, further comprising:
the container assembly including a cartridge configured to be coupled to the first container and the second container, the cartridge including an engagement portion; and
the housing includes a container portion configured to receive the cartridge, the container portion having retainer configured to engage the engagement portion of the cartridge to removably retain the container assembly within the container portion of the housing in a fixed position relative to a home position associated with the drive assembly.

8. The apparatus of claim 7, wherein:
the engagement portion of the cartridge is a first engagement portion, the cartridge including a second engagement portion; and
the retainer of the container portion is a first retainer, the container portion including a second retainer configured to engage the second engagement portion of the cartridge to inhibit movement of the container assembly relative to the housing in at least two directions.

9. An apparatus, comprising:
a housing configured to receive at least a portion of a container assembly, the container assembly including a first container containing a first component and a second container containing a second component, the first container and the second container configured to be coupled to a connector, the container assembly including a first plunger and a second plunger;
a delivery member configured to be coupled to the connector, the delivery member defining a mixing volume containing a bolus of air, the delivery member including an outlet portion configured to be in fluid communication with a body lumen; and
a drive assembly configured to be operatively coupled to the container assembly, the drive assembly configured to move the first plunger within the first container to convey a portion of the first component from the first container and the second plunger within the second container to convey a portion of the second component from the second container, the drive assembly configured to move the first plunger and the second plunger simultaneously for a time period to dispense the portion of the first component and the portion of the second component into the mixing volume to form a hydrogel and to cause the bolus of air to be delivered into the body lumen via the outlet portion of the delivery member.

10. The apparatus of claim 9, wherein the bolus of air has a selected volume sufficient to dilate the body lumen before the hydrogel is conveyed into the body lumen.

11. The apparatus of claim 10, wherein the selected volume is between 0.1 mL and 10 mL.

12. The apparatus of claim 9, wherein the body lumen is one of an artery, vein, capillary, vessel, tissue, lymphatic vessel, vas deferens, epididymis, fallopian tube, duct, bile duct, hepatic duct, cystic duct, pancreatic duct, parotid duct, uterus, or organ of a gastrointestinal tract or circulatory system or respiratory system or nervous system.

13. The apparatus of claim 9, wherein:
the drive assembly includes an electromechanical driver, a drive member, and an electronic control system;
the drive member is configured to be engaged with a plunger assembly, movement of the drive member configured to move the first plunger and the second plunger; and
the electromechanical driver is configured to produce a drive force to move the drive member.

14. The apparatus of claim 9, wherein the delivery member is a catheter.

15. A method of delivering a composition, comprising:
coupling an inlet of a connector to a container assembly, the container assembly including a first component and a second component separate from the first component;
priming the connector by conveying a first portion of the first component from the container assembly to a first outlet of the connector and conveying a first portion of the second component from the container assembly to a second outlet of the connector;
coupling, after the priming, a delivery member to the connector to place the first outlet of the connector and the second outlet of the connector in fluid communication with a mixing volume defined by the delivery member, the coupling of the delivery member is performed such that a bolus of air is within the mixing volume, the delivery member including an outlet portion in fluid communication with a body lumen;
conveying, after the coupling the delivery member, a second portion of the first component and a second portion of the second component into the mixing volume, the second portion of the first component cross-linking with the second portion of the second component to form a hydrogel within the delivery member, the conveying of the second portion of the first component and the second portion of the second component into the mixing volume causing the bolus of air to be delivered into the body lumen; and conveying the hydrogel out of the delivery member via the outlet portion after the delivery of the bolus of air into the body lumen.

16. The method of claim 15, wherein the bolus of air has a selected volume sufficient to dilate the body lumen before the hydrogel is conveyed into the body lumen.

17. The method of claim 16, wherein the selected volume is between 0.1 mL and 10 mL.

18. The method of claim 15, wherein the hydrogel is echogenic, the method further comprising:
identifying the bolus of air via an image of the body lumen.

19. The method of claim 15, wherein the body lumen is one of an artery, vein, capillary, vessel, tissue, lymphatic vessel, vas deferens, epididymis, fallopian tube, duct, bile duct, hepatic duct, cystic duct, pancreatic duct, parotid duct, uterus, or organ of a gastrointestinal tract or circulatory system or respiratory system or nervous system.

20. The method of claim 15, wherein the delivery member is a catheter.

* * * * *